US011627952B2

(12) United States Patent
Eckhof et al.

(10) Patent No.: US 11,627,952 B2
(45) Date of Patent: Apr. 18, 2023

(54) SURGICAL RETRACTOR

(71) Applicant: Surgalign Spine Technologies, Inc., Deerfield, IL (US)

(72) Inventors: Stephan Eckhof, Rietheim-Weilheim (DE); Matthew P. Gephart, Marquette, MI (US); Kale Reid, Marquette, MI (US); Markus Salvermoser, Tuttlingen-Möhringen (DE); Matthew Allan Stilwell, Negaunee, MI (US); Daniel Wefers, Wurmlingen (DE); Marc Mundhenke, Rielasingen-Worblingen (DE)

(73) Assignee: Surgalign Spine Technologies, Inc., Deerfield, IL (US)

( * ) Notice: Subject to any disclaimer, the term of this patent is extended or adjusted under 35 U.S.C. 154(b) by 0 days.

(21) Appl. No.: 17/360,933

(22) Filed: Jun. 28, 2021

(65) Prior Publication Data

US 2021/0401423 A1    Dec. 30, 2021

Related U.S. Application Data

(60) Provisional application No. 63/045,543, filed on Jun. 29, 2020.

(51) Int. Cl.
*A61B 17/02* (2006.01)
*A61B 17/86* (2006.01)
*A61B 17/00* (2006.01)

(52) U.S. Cl.
CPC .......... *A61B 17/0206* (2013.01); *A61B 17/86* (2013.01); *A61B 2017/00473* (2013.01); *A61B 2017/0256* (2013.01)

(58) Field of Classification Search
CPC ... A61B 17/02; A61B 17/0206; A61B 17/025; A61B 2017/0256–0262
See application file for complete search history.

(56) References Cited

U.S. PATENT DOCUMENTS 2,473,266 A    6/1949  Wexler
2,623,517 A   12/1952  Owen et al.
(Continued)

FOREIGN PATENT DOCUMENTS

DE   102016110706   12/2017
WO     2003086202   10/2003
(Continued)

OTHER PUBLICATIONS

Clarity Lateral, Retractor System, Surgical Technique, Pioneer Surgical Technology, 2008, Marquette, Michigan (12 pages).
(Continued)

*Primary Examiner* — Eduardo C Robert
*Assistant Examiner* — Michelle C Eckman
(74) *Attorney, Agent, or Firm* — Fitch, Even, Tabin & Flannery LLP

(57) ABSTRACT

In one aspect, a surgical retractor having sliders configured to have tissue engaging members connected thereto and slider drives including operating members. The operating members are rotatable to cause the slider drives to shift the sliders relative to one another. The surgical retractor includes a coupler having a coupling configuration wherein the coupler connects the slider drives and rotation of one of the operating members causes movement of the sliders. The coupler also has a decoupling configuration wherein the coupler disconnects the slider drives and rotation of the one operating member causes movement of fewer sliders than the sliders that are moved with the coupler in the coupling configuration. The retractor has an actuator connected to the coupler and movable between a dependent slider movement position and an independent slider movement position to shift the coupler between the coupling configuration and the decoupling configuration.

30 Claims, 41 Drawing Sheets

(56) References Cited

U.S. PATENT DOCUMENTS

| | | | |
|---|---|---|---|
| 3,038,468 A | 6/1962 | Raeuchle | |
| 3,724,449 A | 4/1973 | Gauthier | |
| 3,948,259 A | 4/1976 | Bolduc et al. | |
| 3,998,217 A | 12/1976 | Trumbull et al. | |
| 4,010,741 A | 3/1977 | Gauthier | |
| 4,434,791 A | 3/1984 | Darnell | |
| 5,616,117 A | 4/1997 | Dinkler et al. | |
| 5,667,481 A | 9/1997 | Villalta et al. | |
| 5,688,223 A | 11/1997 | Rosendahl | |
| 5,728,046 A | 3/1998 | Mayer et al. | |
| 5,813,978 A | 9/1998 | Jako | |
| 5,928,139 A | 7/1999 | Koros et al. | |
| 5,944,658 A | 8/1999 | Koros et al. | |
| 5,954,635 A | 9/1999 | Foley et al. | |
| 5,957,927 A | 9/1999 | Magee et al. | |
| 5,967,973 A | 10/1999 | Sherts et al. | |
| 6,083,154 A | 7/2000 | Liu et al. | |
| 6,139,493 A | 10/2000 | Koros et al. | |
| 6,206,826 B1 | 3/2001 | Mathews et al. | |
| 6,213,940 B1 | 4/2001 | Sherts et al. | |
| 6,224,545 B1 | 5/2001 | Cocchia et al. | |
| 6,322,500 B1 | 11/2001 | Sikora et al. | |
| 6,416,467 B1 | 7/2002 | McMillin et al. | |
| 6,431,025 B1 | 8/2002 | Koros et al. | |
| 6,464,634 B1 | 10/2002 | Fraser | |
| 6,616,605 B2 | 9/2003 | Wright et al. | |
| 6,800,084 B2 | 10/2004 | Davison et al. | |
| 6,849,064 B2 | 2/2005 | Hamada | |
| 6,869,398 B2 | 3/2005 | Obenchain et al. | |
| 6,896,654 B2 | 5/2005 | Paolitto et al. | |
| 6,932,764 B2 | 8/2005 | Kashyap | |
| 7,195,592 B2 | 3/2007 | Ravikumar et al. | |
| 7,780,594 B2 | 8/2010 | Hutton | |
| 7,931,589 B2 | 4/2011 | Cohen et al. | |
| 7,985,179 B2 | 7/2011 | Gephart et al. | |
| 8,435,269 B2 | 5/2013 | Woolley | |
| 8,550,995 B2 | 10/2013 | Frasier et al. | |
| 8,636,655 B1* | 1/2014 | Childs | A61B 17/0206 600/219 |
| 8,702,600 B2 | 4/2014 | Perrow | |
| 8,882,661 B2 | 11/2014 | Hutton et al. | |
| 8,956,285 B2 | 2/2015 | Gephart et al. | |
| 9,113,852 B2 | 8/2015 | Perrow | |
| 9,498,200 B2 | 11/2016 | Pfabe et al. | |
| 9,579,095 B2 | 2/2017 | Perrow | |
| 9,980,714 B2 | 5/2018 | Perrow et al. | |
| 10,149,671 B2* | 12/2018 | Predick | A61B 17/0206 |
| 10,285,680 B2 | 5/2019 | Friedrich et al. | |
| 10,357,239 B2 | 7/2019 | Perrow et al. | |
| 2002/0111538 A1 | 8/2002 | Wright et al. | |
| 2002/0193666 A1 | 12/2002 | Sherts et al. | |
| 2003/0191371 A1 | 10/2003 | Smith et al. | |
| 2004/0002629 A1 | 1/2004 | Branch et al. | |
| 2004/0059193 A1 | 3/2004 | Fanous | |
| 2004/0087833 A1 | 5/2004 | Bauer et al. | |
| 2004/0133077 A1 | 7/2004 | Obenchain et al. | |
| 2004/0133201 A1 | 7/2004 | Shluzas et al. | |
| 2004/0176665 A1 | 9/2004 | Branch et al. | |
| 2004/0193018 A1 | 9/2004 | Thalgott et al. | |
| 2004/0230100 A1 | 11/2004 | Shluzas | |
| 2004/0242969 A1 | 12/2004 | Sherts et al. | |
| 2005/0080320 A1 | 4/2005 | Lee et al. | |
| 2005/0137461 A1 | 6/2005 | Marchek et al. | |
| 2005/0149035 A1 | 7/2005 | Pimenta et al. | |
| 2005/0159650 A1 | 7/2005 | Raymond et al. | |
| 2005/0159651 A1 | 7/2005 | Raymond et al. | |
| 2005/0192485 A1 | 9/2005 | Branch et al. | |
| 2005/0215862 A1 | 9/2005 | Larson et al. | |
| 2005/0215866 A1 | 9/2005 | Kim | |
| 2005/0234304 A1 | 10/2005 | Dewey et al. | |
| 2005/0261694 A1 | 11/2005 | Orton et al. | |
| 2005/0277812 A1 | 12/2005 | Myles | |
| 2006/0004261 A1 | 1/2006 | Douglas | |
| 2006/0030858 A1 | 2/2006 | Simonson et al. | |
| 2006/0052672 A1 | 3/2006 | Landry et al. | |
| 2006/0074445 A1 | 4/2006 | Gerber et al. | |
| 2006/0224044 A1 | 10/2006 | Marchek et al. | |
| 2007/0010716 A1 | 1/2007 | Malandain et al. | |
| 2007/0118022 A1 | 5/2007 | Hutton | |
| 2007/0156025 A1 | 7/2007 | Marchek et al. | |
| 2007/0161867 A1 | 7/2007 | Fowler et al. | |
| 2007/0203399 A1 | 8/2007 | Gephart et al. | |
| 2007/0238932 A1 | 10/2007 | Jones et al. | |
| 2007/0282171 A1 | 12/2007 | Karpowicz et al. | |
| 2008/0033251 A1 | 2/2008 | Araghi | |
| 2008/0188718 A1 | 8/2008 | Spitler et al. | |
| 2008/0214898 A1 | 9/2008 | Warren | |
| 2009/0069635 A1 | 3/2009 | Gephart et al. | |
| 2011/0130793 A1* | 6/2011 | Woolley | A61B 17/7076 606/279 |
| 2015/0209022 A1 | 7/2015 | Ruppert et al. | |
| 2015/0313585 A1* | 11/2015 | Abidin | A61B 17/025 600/219 |
| 2016/0074029 A1* | 3/2016 | O'Connell | A61B 17/025 600/215 |
| 2016/0174997 A1 | 6/2016 | Spitznagel | |
| 2016/0331431 A1 | 11/2016 | Gephart | |
| 2017/0049428 A1* | 2/2017 | Cryder | A61B 17/0206 |
| 2018/0029824 A1 | 2/2018 | Gephart et al. | |
| 2019/0216453 A1 | 7/2019 | Predick | |
| 2020/0038009 A1 | 2/2020 | Perrow | |
| 2021/0007727 A1 | 1/2021 | Riemhofer | |

FOREIGN PATENT DOCUMENTS

| | | |
|---|---|---|
| WO | 2004047650 | 6/2004 |
| WO | 2005092206 | 10/2005 |
| WO | 2005094695 | 10/2005 |
| WO | 2005096735 | 10/2005 |
| WO | 2007087536 | 8/2007 |
| WO | 2008039427 | 4/2008 |
| WO | 2014140100 | 9/2014 |
| WO | 2016025020 | 2/2016 |

OTHER PUBLICATIONS

Hynes, Richard A., et al., Oblique Lateral Interbody Fusion for L2 to L5 Surgical Technique, OLIF 25 Procedure, Medtronic Sofamor Danek USA, copyright 2012, Memphis, TN (32 pages).

Image of NuVasive MAS TLIF retractor publicly available before Jun. 29, 2020, NuVasive, Inc. (1 page).

Images of CENTRIC®—T Retractor Life Spine publicly available before Jun. 29, 2020 (2 pages).

Images of OLIF Procedures—OLIF 25 Medtronic publicly available before Jun. 29, 2020 (2 pages).

Interlagos Retractor System Surgical Technique, Altus Spine, copyright 2017, West Chester, PA (16 pages).

M.U.S.T. Mini Open Surgical Technique, Minimally Invasive Retractor System, Medacta International SA, Last updated Jul. 2017, pp. 1-20 (20 pages).

OLIF25™—OLIF Procedures, Medtronic, captured via Wayback Machine on Sep. 28, 2021, last updated Nov. 2019, <<https://www.medtronic.com/us-en/healthcare-professionals/therapies-procedures/spinal-orthopaedic/olif/procedural-solutions/olif25.html>> (4 pages).

Pedicle-Based Retractor System, Centric-T Retractor, Life Spine, Inc., copyright 2020, https://lifespine.com/centric-t/ (3 pages).

ProAccess Radiolucent Retractor Blades, Synthes Spine, product offerings guide provided by the manufacturer, 2004, Paoli, Pennsylvania (2 pages).

Stryker Spine's Less Invasive Transforaminal Lumbar Interbody Fusion, LITe® TLIF, Stryker, copyright 2015, Allendale, NJ (5 pages).

SynFrame Access and Retractor System Assembly Guide, SYNTHES Spine, assembly guide provided by the manufacturer, 1999, Paoli, Pennsylvania (12 pages).

TeDan Surgical Innovations, Phantom XL Series brochure, copyright date 2013 (2 pages).

Timberline® Lateral Fusion System, Zimmer Biomet Spine, Inc., copyright 2016 (6 pages).

(56) References Cited

OTHER PUBLICATIONS

Webb, J., Spine-the future, AO Foundation Webpage, available at: http://www.aofoundation.org/AOFileServer/PortaiFiles?FilesPath=/Extranet2007/active/_attlwor/act!Dialogue/1999_2/spine.pdf, accessed Apr. 10, 2009 (1 page).

YouTube Video entitled "MARS™3V," Screen Captures, Globus Medical, published Sep. 21, 2016, https://www.facebook.com/GlobusMedical/videos/mars3v/1250646118314065/ (6 pages).

YouTube Video entitled "MARS™3VL," Screen Captures, Globus Medical, published Feb. 15, 2016, https://www.youtube.com/watch?v=RW8zOQAg8SA (6 pages).

YouTube Video entitled "MAS® TLIF Patient Animation," Screen Captures and Audio Transcription, NuVasive Inc., https://www.youtube.com/watch?v=ggdKG0OvL90, published May 13, 2014 (12 pages).

\* cited by examiner

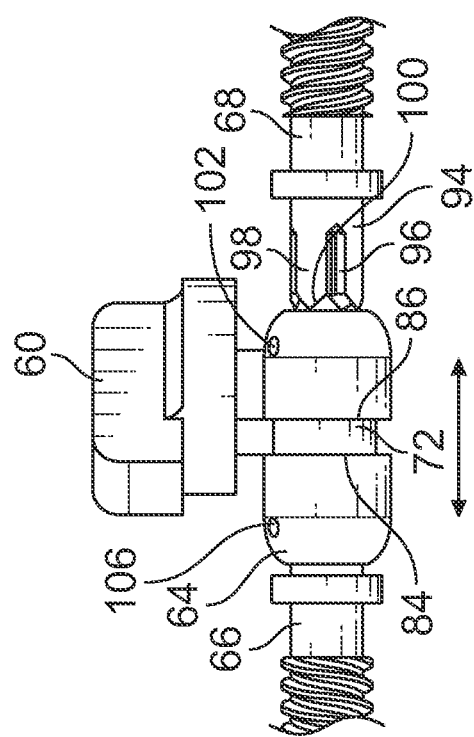
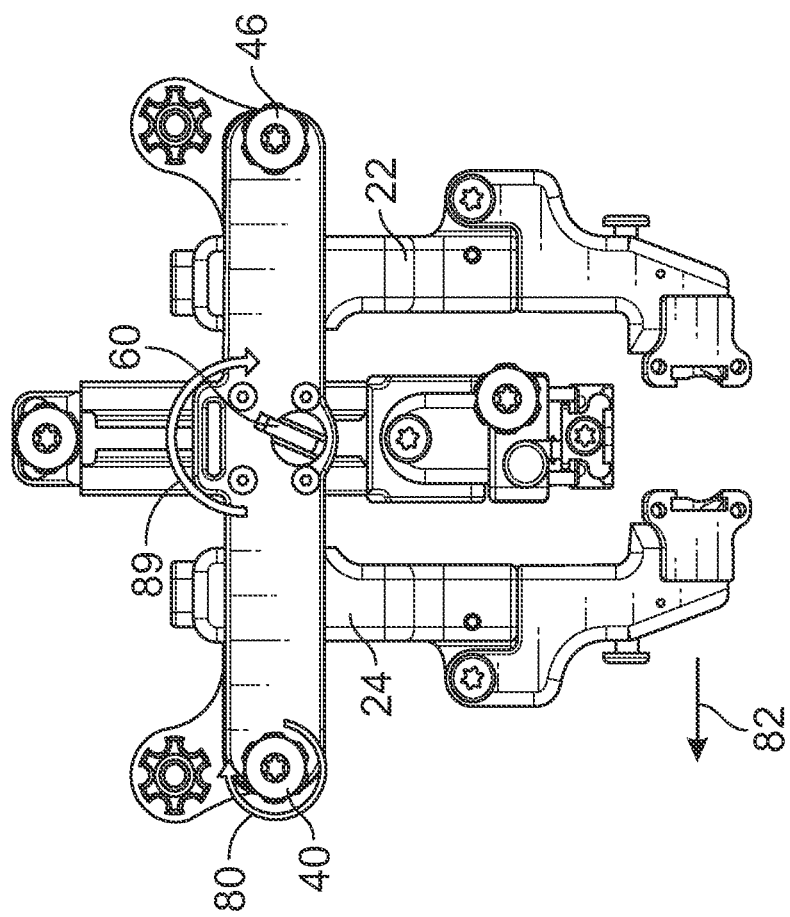
FIG. 5
FIG. 4

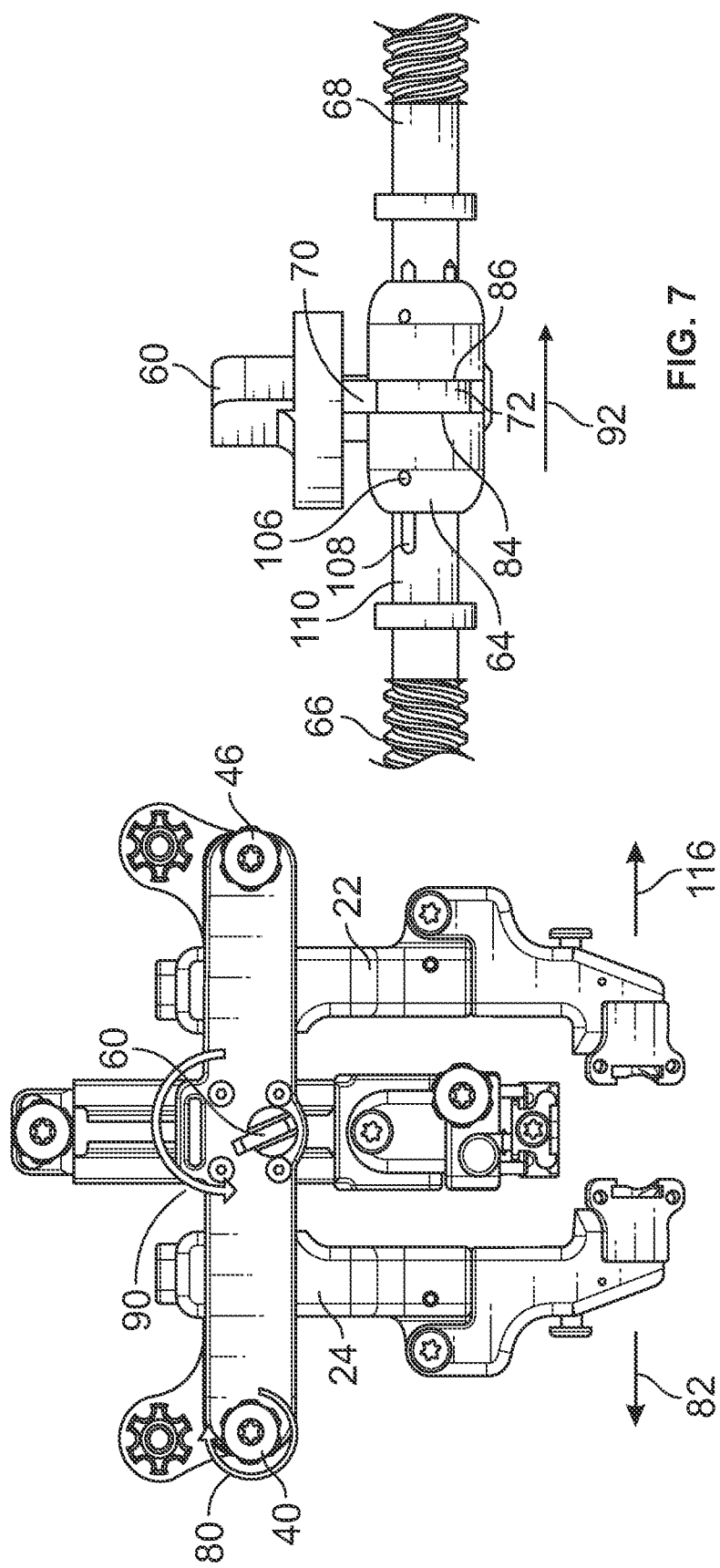

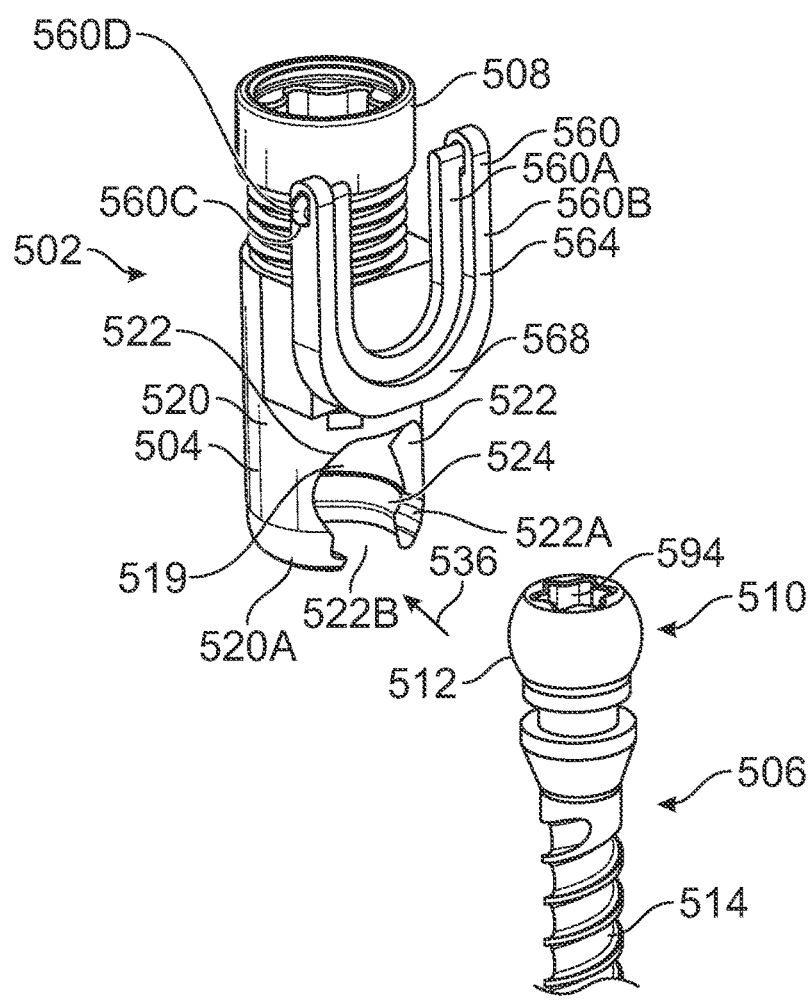
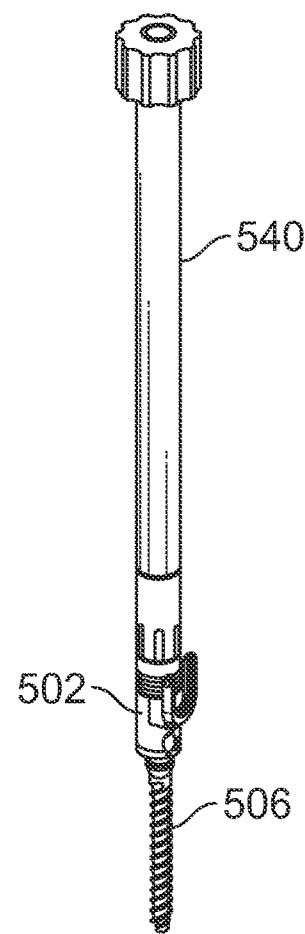
FIG. 21
FIG. 22

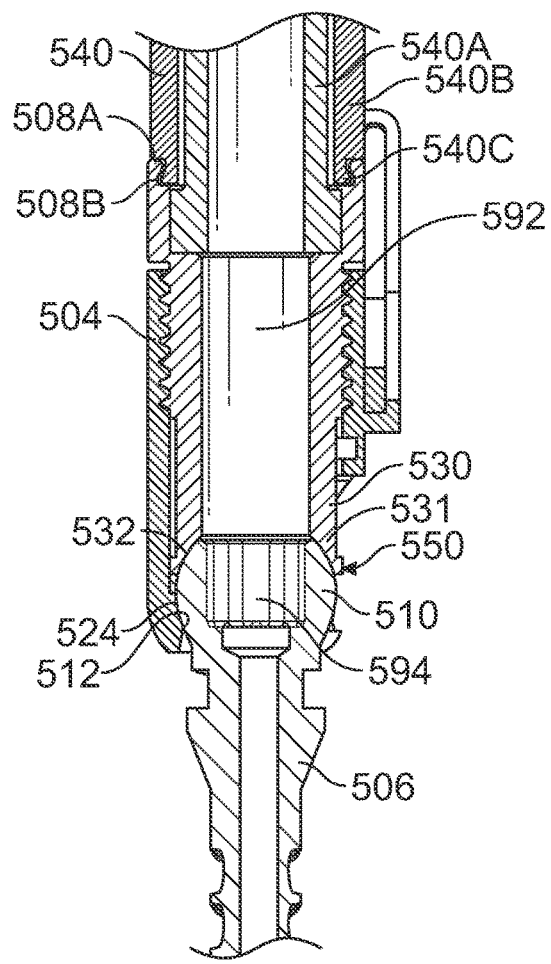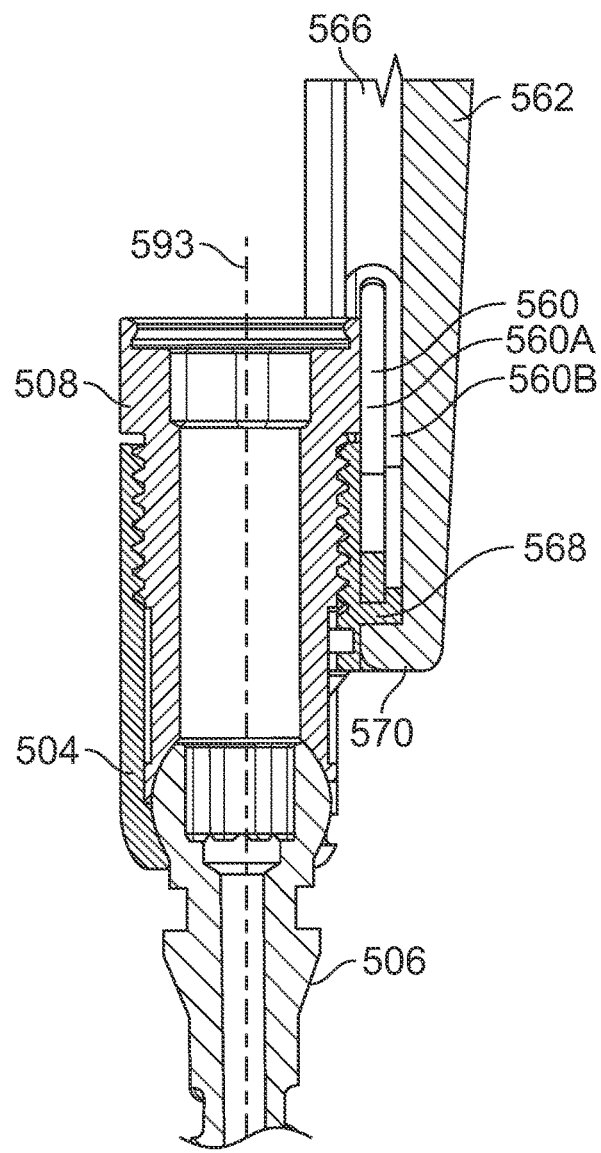
FIG. 23
FIG. 24

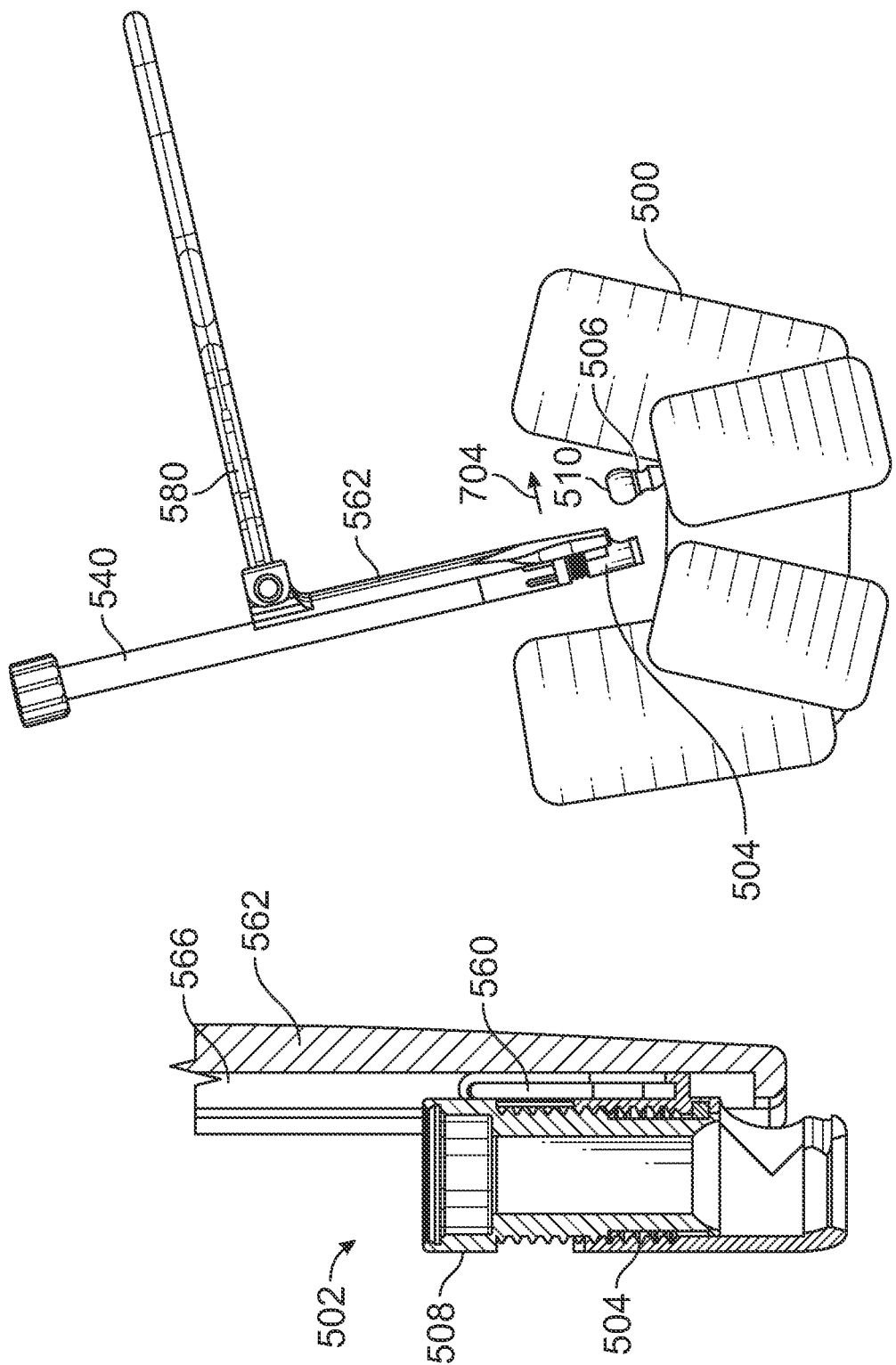

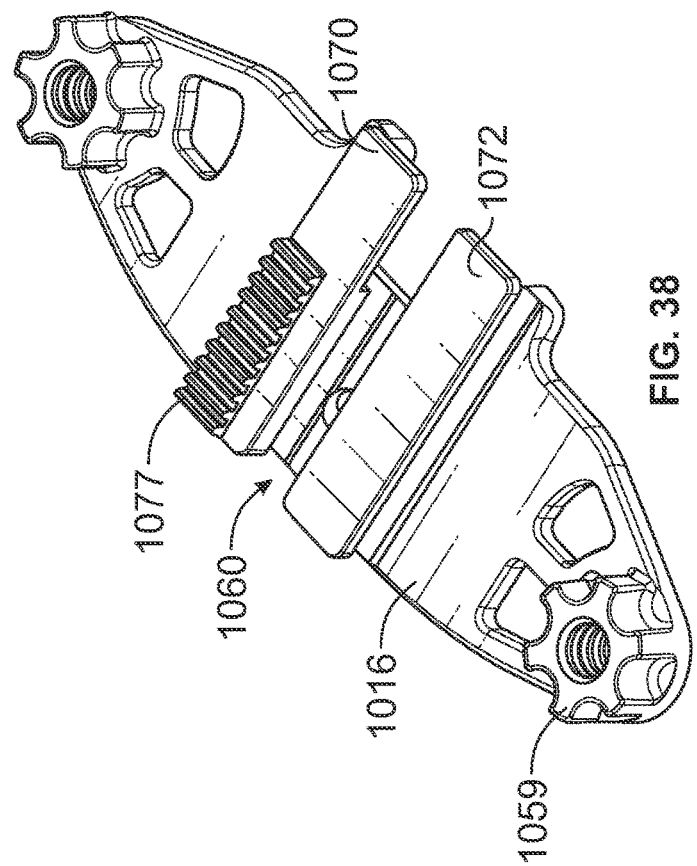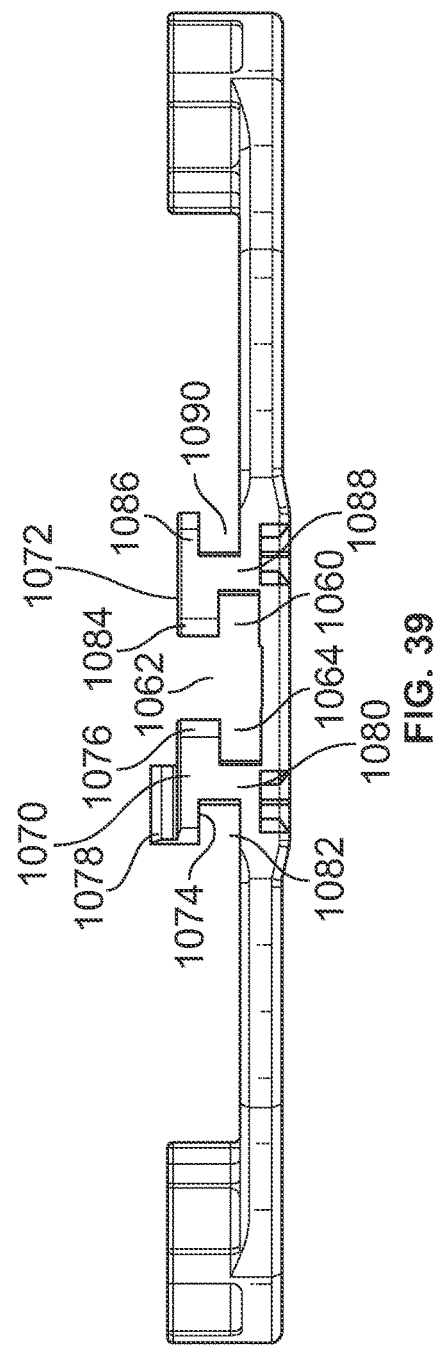

SURGICAL RETRACTOR

CROSS-REFERENCE TO RELATED APPLICATION

This application claims the benefit of U.S. Provisional Patent Application No. 63/045,543, filed Jun. 29, 2020, which is hereby incorporated by reference in its entirety.

FIELD

This disclosure relates to surgical retractors.

BACKGROUND

Surgical retractors are known that have two or more blades to retract an incision. Typically, each blade has an associated drive mechanism that permits the blade to be retracted as desired by a surgeon.

Surgical retractor systems are known that utilize an anchor to secure a blade of a retractor to a bone to locate and stabilize the retractor. The remaining blades of the retractor are retracted during a surgical procedure to enlarge an incision. Some surgical retractor systems include blades having apertures that are positioned against bones and bone screws are driven through the apertures and into bone. The bone screws secure the blades to the bone.

One type of surgical retractor has a frame with a first section that is connected to a support structure, such as an iron intern, and a retractor blade movably mounted to the first frame section. The surgical retractor has a second frame section movable relative to the first section, the second frame section supporting a pair of retractor blades that are movably mounted to the second frame section by elongate assemblies. The elongate assemblies are relatively long and increase the length of the surgical retractor along the patient such that the surgical retractor covers a large area of the patient. The long aspect ratio of the surgical retractor may make surgical site imaging difficult during some oblique procedures, such as oblique lateral interbody fusion (OLIF) procedures.

SUMMARY

In one aspect of the present disclosure, a surgical retractor is provided having sliders configured to have tissue engaging members connected thereto and slider drives including operating members. The operating members are rotatable to cause the slider drives to shift the sliders relative to one another. The surgical retractor includes a coupler having a coupling configuration wherein the coupler connects the slider drives and rotation of one of the operating members causes movement of the sliders. The coupler also has a decoupling configuration wherein the coupler disconnects the slider drives and rotation of the one operating member causes movement of fewer sliders than the sliders that are moved with the coupler in the coupling configuration. The retractor has an actuator connected to the coupler and movable between a dependent slider movement position and an independent slider movement position to shift the coupler between the coupling configuration and the decoupling configuration. The surgical retractor thereby permits a surgeon to retract a plurality of tissue engaging members by rotating the one operating member, or retract fewer tissue engaging members, depending on the position of the actuator set by the surgeon.

The present disclosure also provides a retractor system including a retractor, a tissue engaging member assembly, and a bone screw having a head portion with a rotary drive structure and a threaded shank portion for engaging a bone. The tissue engaging member assembly includes an adapter configured for being secured to the bone screw. The adapter includes a body having an interior to receive the head portion of the bone screw, the body having a central longitudinal axis. The body further includes an opening of the body sized to permit the body and the bone screw head to be shifted laterally relative to one another to advance the bone screw head portion through the opening of the body and into the interior of the body. In this manner, the adapter body may be connected to a bone screw previously secured to a bone by shifting the body laterally to advance the body onto the head portion of the bone screw. In another approach, the adapter body may be connected to a bone screw prior to the bone screw being driven into bone. The ability to connect the adapter to the bone screw before or after the bone screw is driven into bone provides different approaches for a surgeon to connect the tissue engaging member assembly to a bone.

In another aspect, a surgical retractor is provided that includes a base frame having a portion to be secured to a support structure, a first slider to receive a first tissue engaging member, and a first slider drive operable to shift the first slider between extended and retracted positions relative to the base frame. The surgical retractor has an intermediate frame and a frame slide connection between the base frame and intermediate frame. There are second and third sliders on opposite sides of the first slider to receive second and third tissue engaging members. The second and third sliders include bodies, arms, and pivot connections between the bodies and the arms. The pivot connections between the bodies and the arms are onboard the intermediate frame. Because the pivot connections are onboard the intermediate frame, the pivot connections and associated portions of the bodies and arms are above the intermediate frame rather than being above the surgical field which minimizes imaging obstruction by the retractor during some procedures such as oblique lateral interbody fusion (OLIF) procedures.

The surgical retractor further includes slide connections between the bodies of the second and third slider and the intermediate frame. Second and third slider drives are operable to shift the second and third sliders longitudinally between extended and retracted positions relative to the intermediate frame. The arms of the second and third sliders extend laterally outward from the intermediate frame to position the second and third tissue engaging members laterally offset and spaced from the intermediate frame. The arms thereby extend laterally outward far enough to position the second and third sliders in the patient while minimizing the surgical field occupied by the surgical retractor. The surgical retractor further includes an intermediate frame drive operable to shift the intermediate frame and the second and third sliders connected thereto relative to the base frame to facilitate positioning of the second and third sliders independent of the first slider.

BRIEF DESCRIPTION OF THE DRAWINGS

FIG. 4 is a top plan view of the retractor of FIG. 1 showing the switch in an independent slider movement position for independent lateral slider movement such that turning of a knob of one of the lateral sliders causes movement of the one lateral slider;

FIG. 5 is an elevational view of the switch and a coupler of the retractor in a decoupling configuration so that the drive shafts may turn independently of one another;

FIG. 6 is a view similar to FIG. 4 showing the switch in a dependent slider movement position wherein turning of one lateral slider knob of the retractor causes simultaneous movement of the lateral sliders;

FIG. 7 is an elevational view of the switch and the coupler in the configuration of FIG. 6 showing the coupler coupling the drive shafts of the slider so that the drive shafts turn together;

FIGS. 21-30 show a method of securing the retractor of FIG. 1 to a spinal bone;

FIGS. 31-36 show another method of connecting the retractor of FIG. 1 to a spinal bone.

FIG. 38 is a perspective view of the base frame of FIG. 37 showing structures of the base frame that form a slide connection with the intermediate frame and a medial slider of the retractor;

FIG. 39 is a side elevational view of the base frame of FIG. 38 showing a central recess that receives a projection of the medial slider and recesses laterally outward from the central recess that receive flange portions of the intermediate frame;

DETAILED DESCRIPTION

Figure 1:
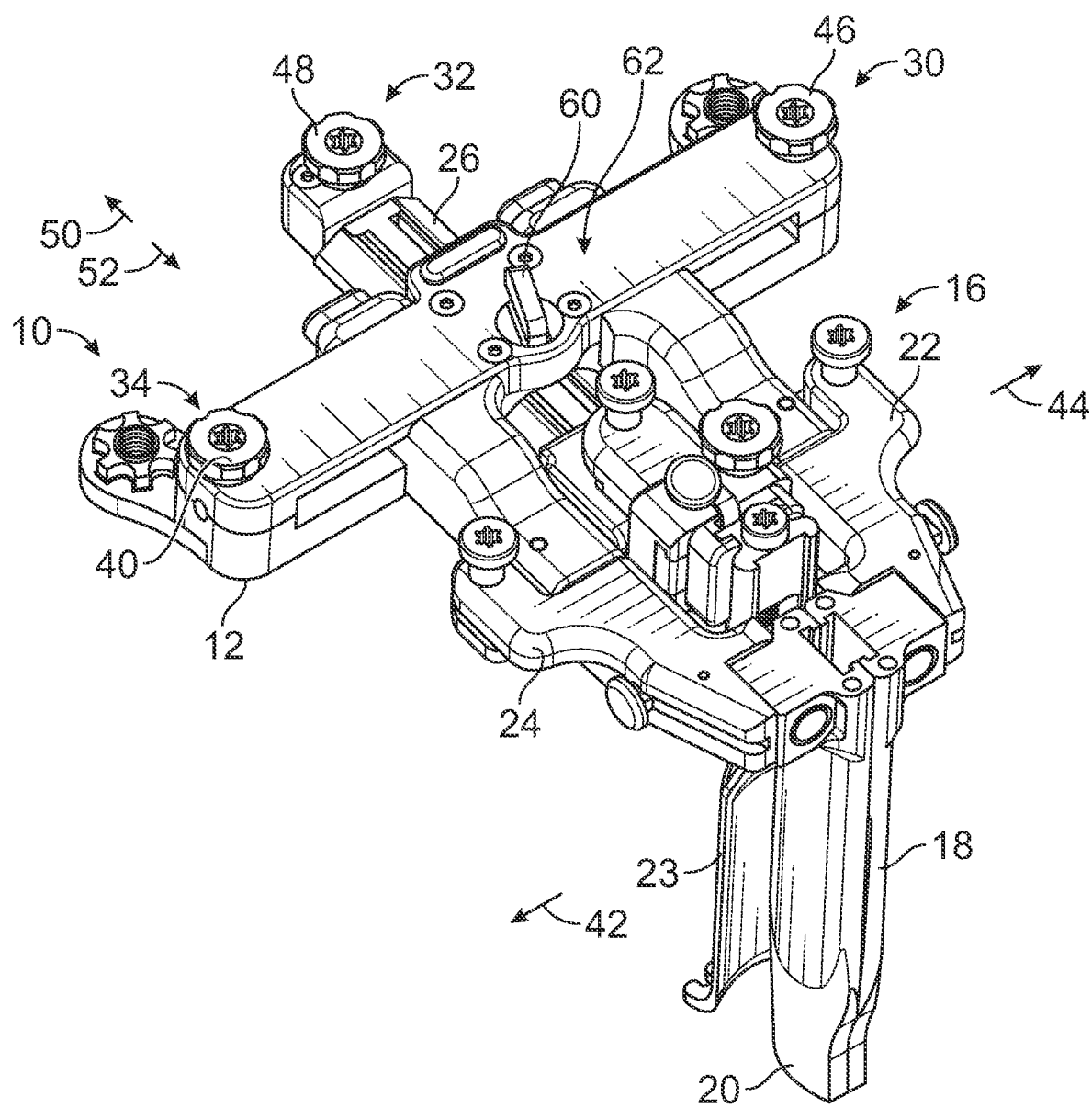
FIG. 1 is a perspective view of a retractor having a pair of lateral blades, a medial blade, and sliders connecting blades to the frame.
Figure 2:
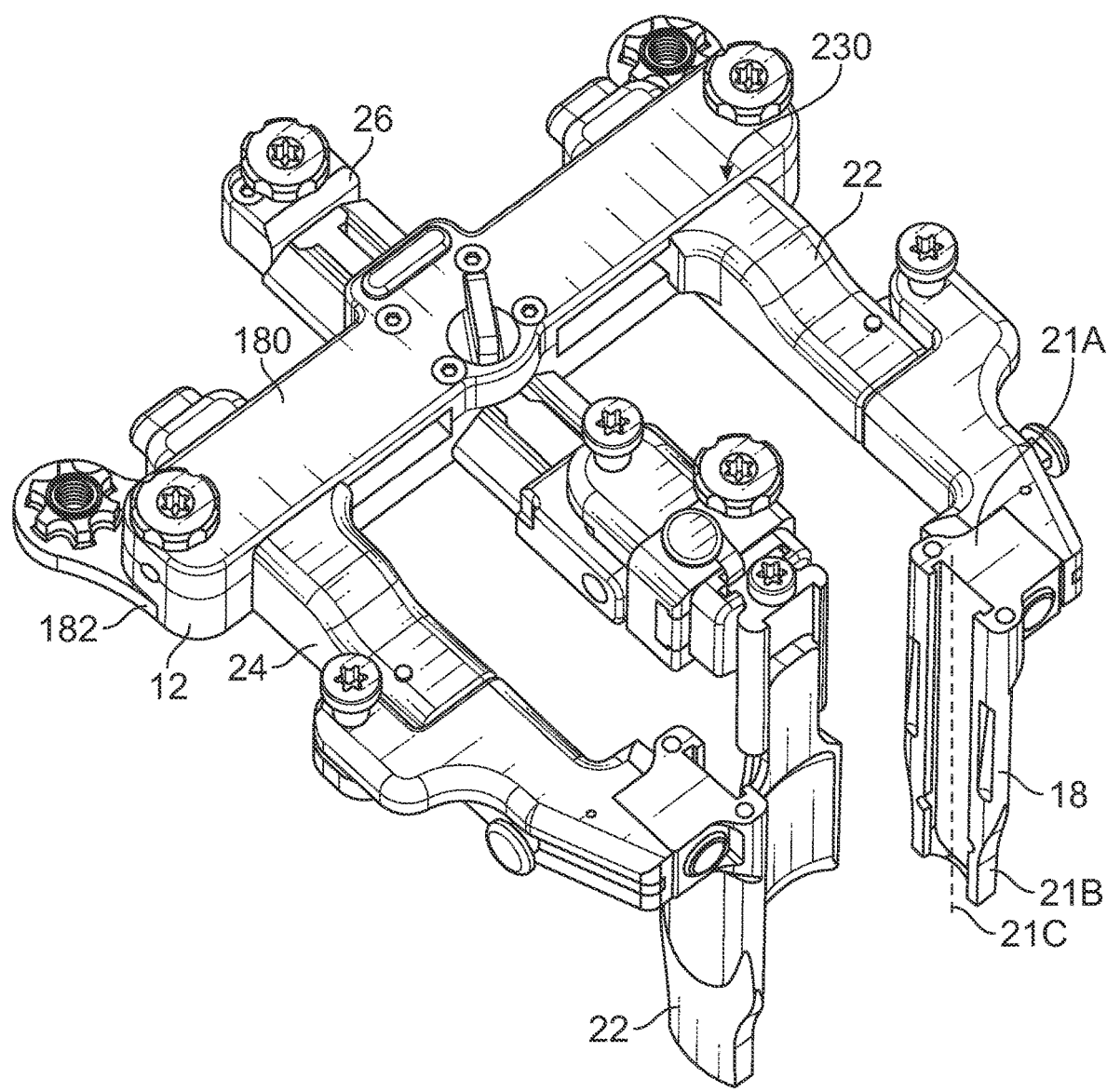
FIG. 2 is a perspective view of the retractor of FIG. 1 showing the retractor in an expanded configuration with the blades moved apart from one another.

Regarding FIG. 1, a retractor 10 is provided that may be utilized in, for example, a posterior spinal surgery. The retractor 10 includes a frame 12, one or more tissue engaging members such as blades 14, and one or more operating mechanisms 16 connecting the blades 14 to the frame 12. In one embodiment, the blades 14 include lateral blades 18, 20 and a medial blade 23. The one or more operating mechanisms 16 include lateral sliders 22, 24, 26 and drives 30, 34, 32 operable to move the sliders 22, 24, 26 relative to the frame 12. The lateral blades 18, 20 each include a proximal end portion 21A (see FIG. 2) configured to connect to the sliders 22, 24, a distal end portion 21B, and a longitudinal axis 21C. The drive 34 includes a drive member including knob 40 that may be turned to shift the slider 24 in directions 42, 44 and the drive 30 includes a drive member including a knob 46 that may be turned to shift the slider 22 in directions 42, 44. Likewise, the drive 32 includes a drive member including a knob 48 that may be turned to remove the slider 26 in directions 50, 52.

The retractor 10 includes a selector, such as a switch 60, that is operable to adjust a coupler 62 connecting the drives 30, 34. Regarding FIG. 3, the coupler 62 includes a sleeve 64 that selectively couples threaded drive shafts 66, 68 of the drives 30, 34. Regarding FIG. 4, the switch 60 has been turned in direction 89 to an independent slider movement position that causes the coupler 62 to be in an independent slider movement configuration. Specifically, with the switch 60 in the position shown in FIG. 4, the switch 60 has a portion, such as a pin 70, that rides in a channel 72 of the sleeve 64 and keeps the sleeve 64 spaced from the drive shaft 68 of the drive 34. In this configuration, turning the knob 40 in direction 80 as shown in FIG. 4 causes the slider 24 to retract in direction 82. However, because the sleeve 64 is not connected to the drive shaft 68, the sleeve 64 does not transfer rotation of the drive shaft 68 to the drive shaft 66. Thus, the slider 24 may move independently of the slider 22 when the knob 40 is turned in direction 80. Similarly, turning of the knob 46 with the switch 60 in a position shown in FIG. 4 produces movement of the slider 42 but not movement of the slider 24.

Regarding FIG. 5, the pin 70 of the switch 60 rides in the channel 72 of the sleeve 64 as the sleeve 64 turns with the drive shaft 66. The channel 72 is annular to provide clearance for the pin 70 as the sleeve 64 rotates with the drive shaft 66. The channel 72 includes walls 84, 86 that the pin 70 may contact to shift the sleeve 64 between a disengaged position (see FIG. 5) and an engaged position (see FIG. 7).

Regarding FIG. 6, the switch 60 may be turned to a dependent slider movement position which reconfigures the coupler 62 to a dependent slider movement configuration. Turning the switch 60 in direction 90 causes the pin 70 to contact the wall 86 of the channel 72 of the sleeve 64 and shifts the sleeve 64 axially in direction 92. Regarding FIGS. 5 and 7, the drive shaft 68 has a connecting portion 94 with openings, such as slots 96 and prongs 98 separating the slots 96. The prongs 98 have tapered surfaces 100 that may form a pointed end of the prongs 98. The tapered surfaces guide a pin 102 that extends diametrically across a through opening 104 (see FIG. 10) of the sleeve 64. When the pin 102 has been shifted into the slots 96, turning of the sleeve 64 is transferred into turning of the drive shaft 68 via lacing or engagement of the pin 102 and the prongs 98. In one embodiment, the sleeve 64 includes a pin 106 that extends diametrically across a similar opening at the opposite end of the sleeve 64. The pin 106 extends through an opening, such as a slot 108, of a connecting portion 110 of the drive shaft 66.

Regarding FIG. 6, with the switch 60 in the dependent slider movement position of FIG. 6, the sleeve 64 couples the drive shafts 66, 68 so that the turning of the knob 40 in direction 80 causes movement of both sliders 22, 24 in directions 82, 116. In this manner, rotation of the single knob 40 produces retractive movement of the sliders 22, 24 in directions 82, 116. Conversely, turning of the knob 46 would also produce concurrent movement of the sliders 22, 24 due to the coupling of the drive shafts 66, 68.

Figure 8:
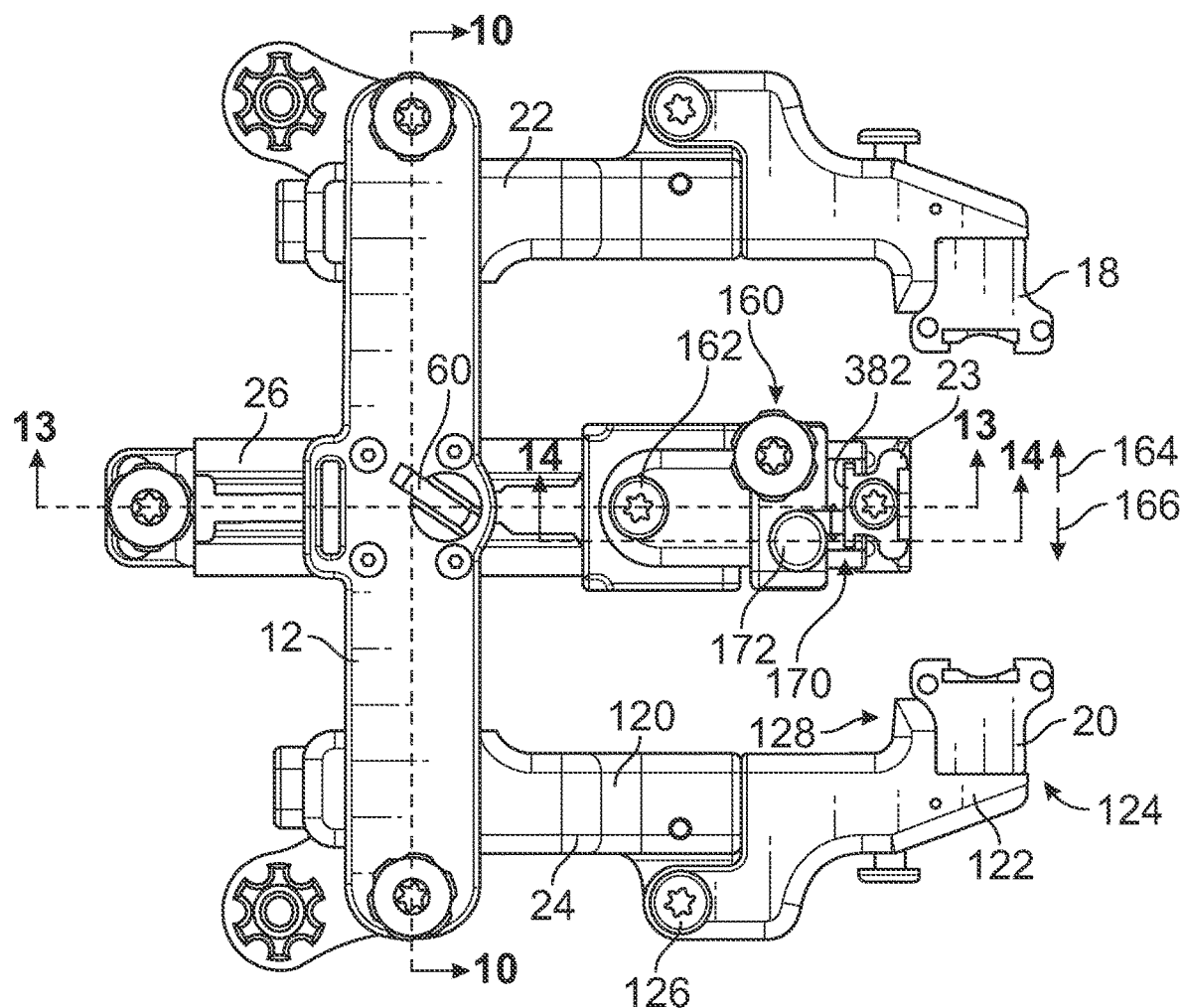
FIG. 8 is a top plan view of the retractor of FIG. 1 showing the sliders projecting from the frame of the retractor.
Figure 9:
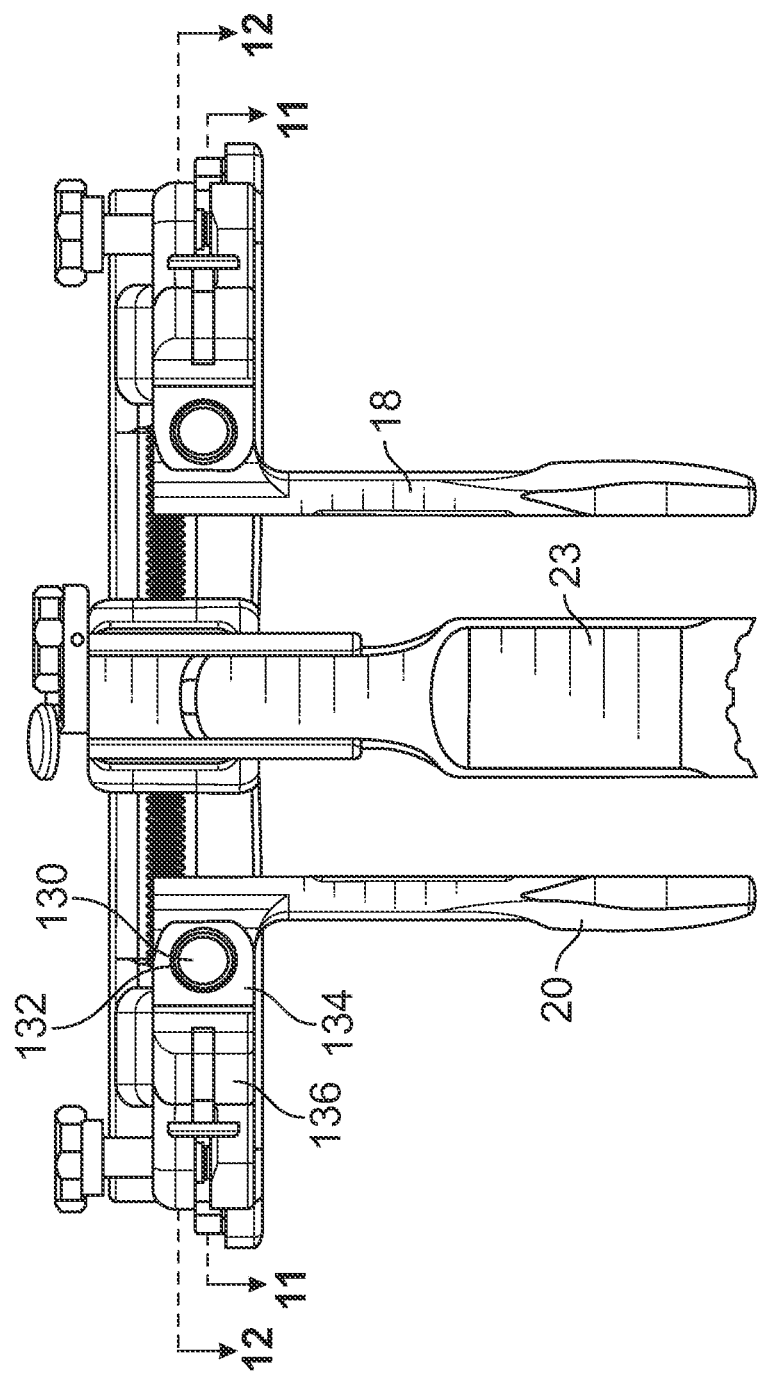
FIG. 9 is an elevational side view showing bosses of the sliders extending in openings of the sliders to connect the blades to the sliders.
Figure 11:
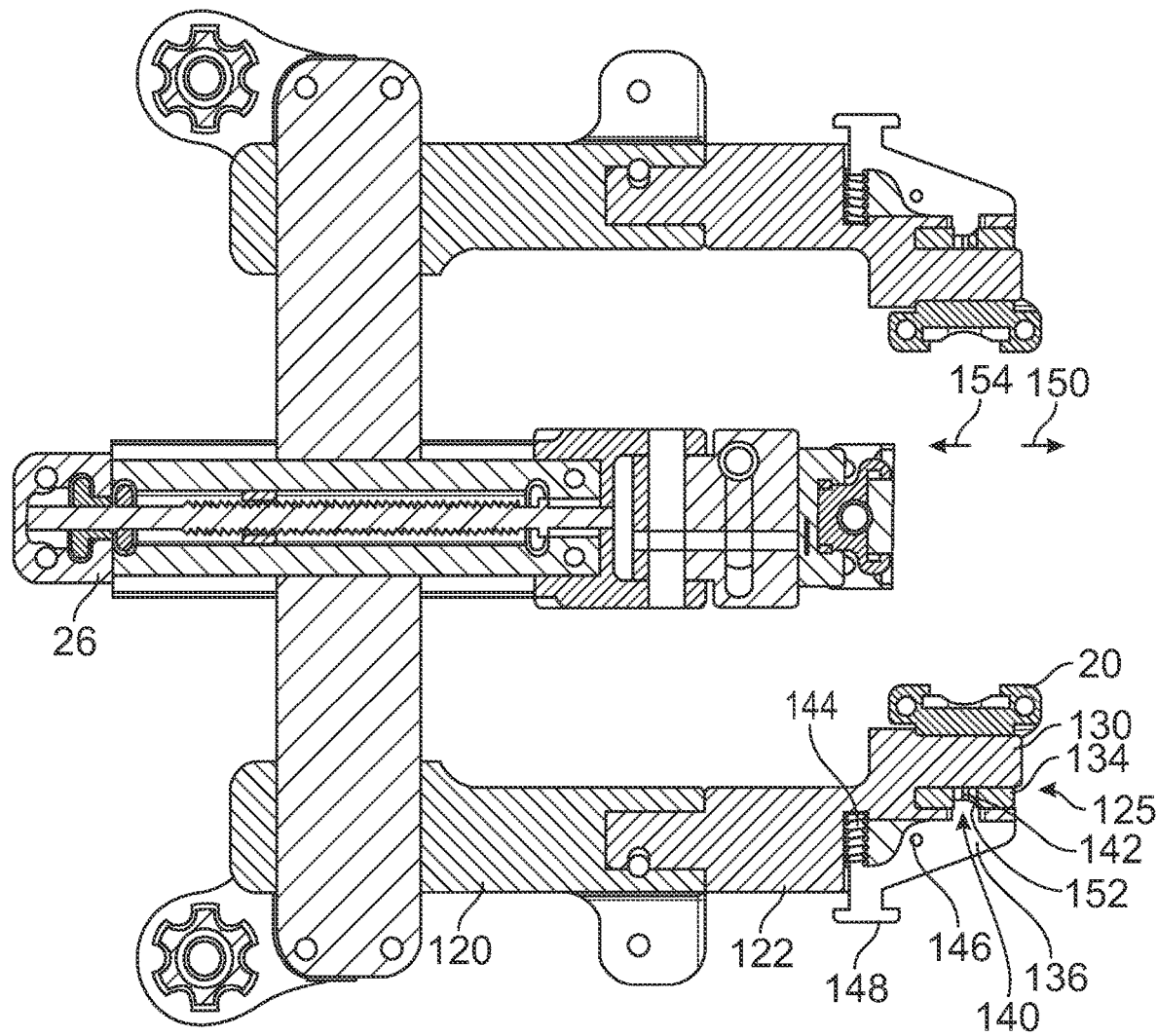
FIG. 11 is a cross-sectional view taken across line 11-11 in FIG. 9 showing latches of the lateral sliders that are spring-biased to releasably secure the blades to the lateral sliders.

Regarding FIG. 8, the lateral sliders 22, 24 each include a slider body 120, a slider arm 122, and a releasable connection 124 with the blades 18, 20. The lateral sliders 22, 24 each include a blade toeing member, such as a fastener 126, that may be turned to pivot the slider arm 122 relative to the slider body 120 to toe out the associated blade 18, 20. The slider arm 122 includes a blade support 128 which, in one embodiment, includes a boss 130 (see FIG. 9), that extends in an opening 132 of a mounting portion 134 of the blade 120. The releasable connection 124 includes a lock 125 such as a latch 136 having a tooth 140 (see FIG. 11) that extends into an opening 142 of the mounting portion 134 of the blade 20 to engage the blade 20. The lock 125 further includes a biasing member, such as a spring 144, that biases the latch 136 about a pin 146 to keep the tooth 140 extending in the opening 142 of the blade 20. The latch 136 includes a release button 148 that may be pressed to pivot the latch 136 about the pin 146 and disengage the tooth 140 from the opening 142 of the blade 20. Regarding FIG. 11, with the tooth 140 withdrawn from the opening 142, the blade 20 may be shifted in direction 150 and disconnected from the boss 130. The tooth 140 may include a tapered surface 152 that causes the tooth 140 to shift outward when the blade 20 is advanced in direction 154 onto the boss 130. This shifting of the tooth 140 outward permits the mounting portion 134 to be advanced onto the boss 130 until the opening 142 aligns with the tooth 140. At this point, the spring 144 urges the tooth 140 into the opening 142. In this manner, the blade 20 may be connected to the slider 24 by advancing the mounting portion 134 onto the boss 130 in direction 154 and the latch 136 automatically engages the blade 20 to keep the blade 20 on the slider 24 until the release button 148 is pressed.

Figure 17:
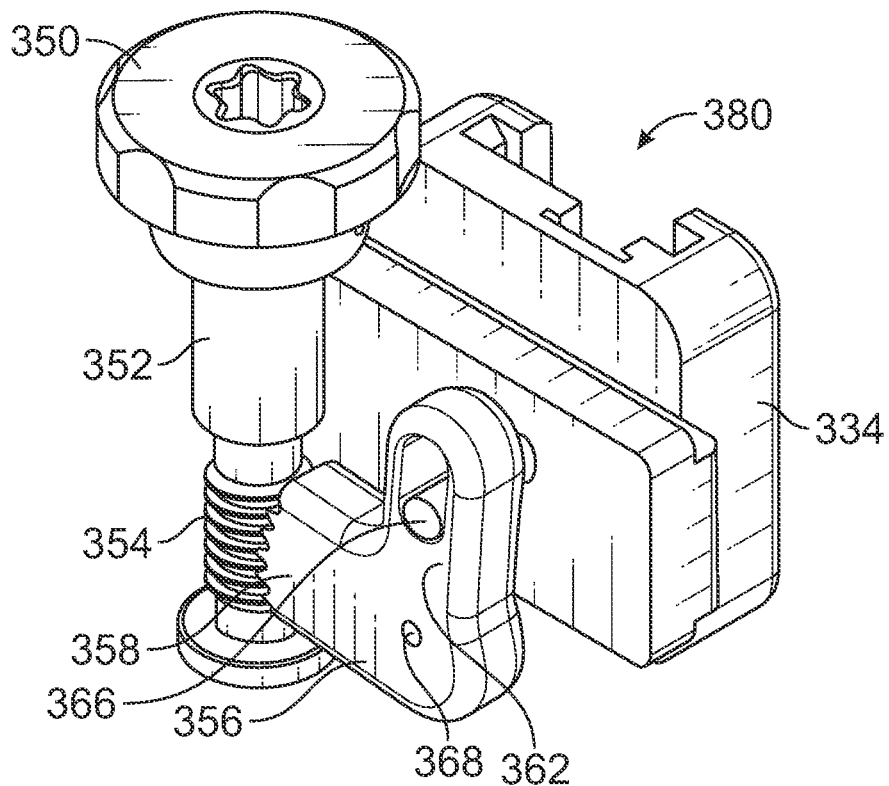
FIG. 17 is a perspective view of a blade translation mechanism of the medial slider.
Figure 18:
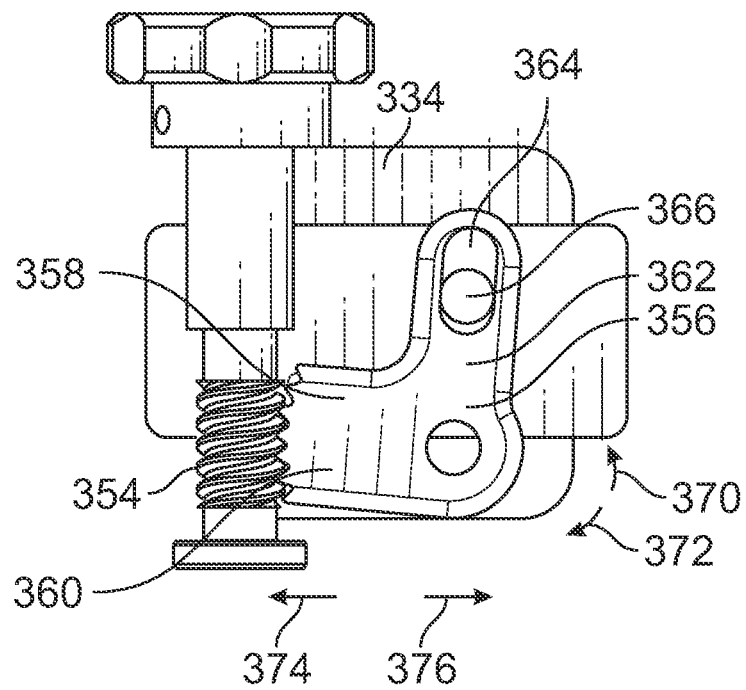
FIG. 18 is an elevational view of the blade translation mechanism of FIG. 17 showing a geared lever of the mechanism engaged with threads of a shaft and a pin of the mechanism.

Regarding FIG. 8, the slider 26 includes a medial blade translation mechanism 160 including a knob 162 that may be turned to shift the medial blade 23 in directions 164, 166, as discussed in greater detail below with respect to FIGS. 17 and 18. The slider 26 further includes a medial blade retainer 170 that keeps the blade 23 connected to the slider 26. The retainer 170 includes a blade release button 172 that may be pressed to permit the blade 23 to be disconnected from the slider 26.

Figure 3:
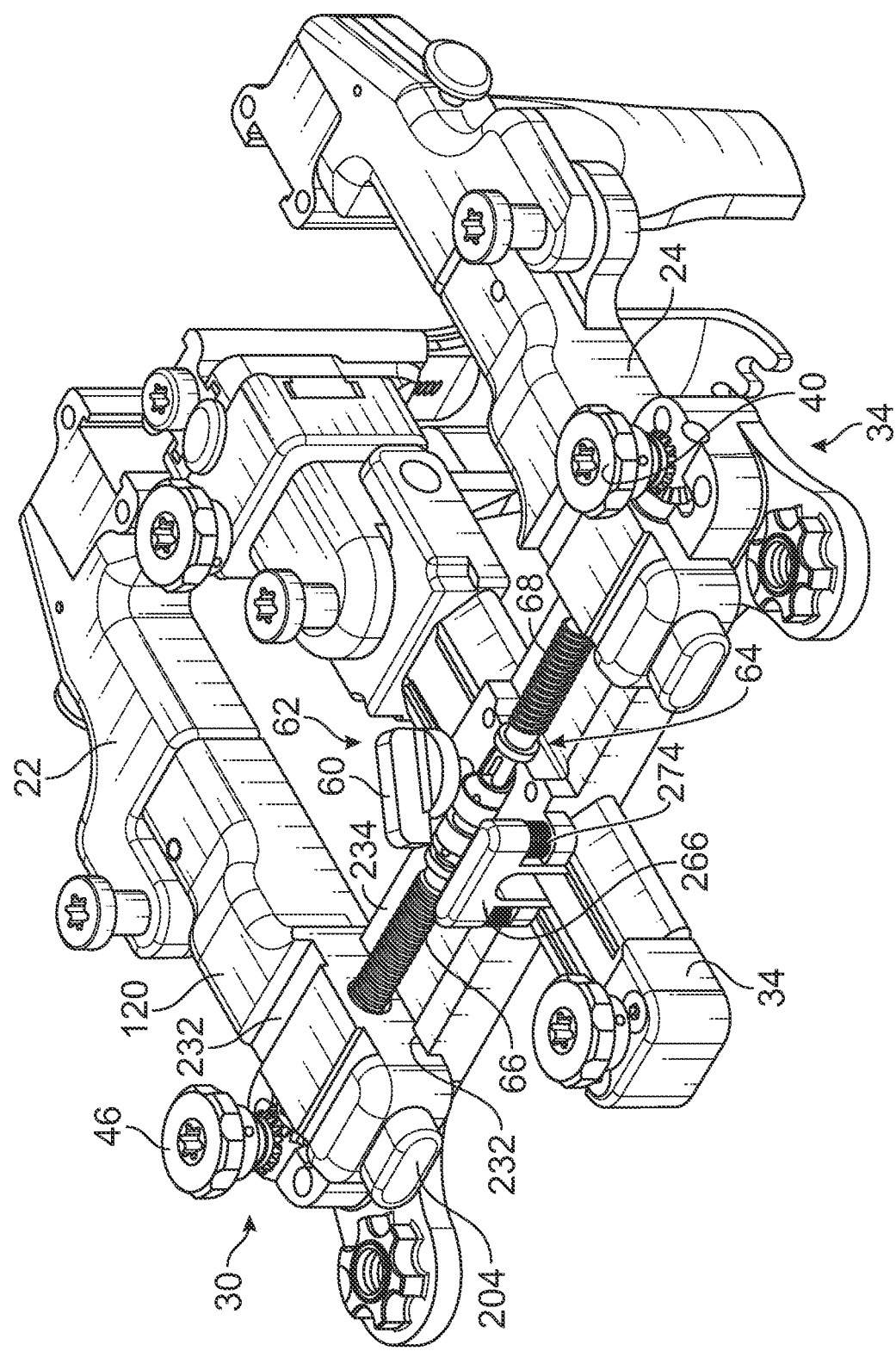
FIG. 3 is a rear perspective view of the retractor of FIG. 1 with a frame upper body removed to show a switch of the retractor that selectively couples drive shafts of the lateral sliders to permit independent or simultaneous movement of the lateral sliders with turning of associated knobs.
Figure 10:
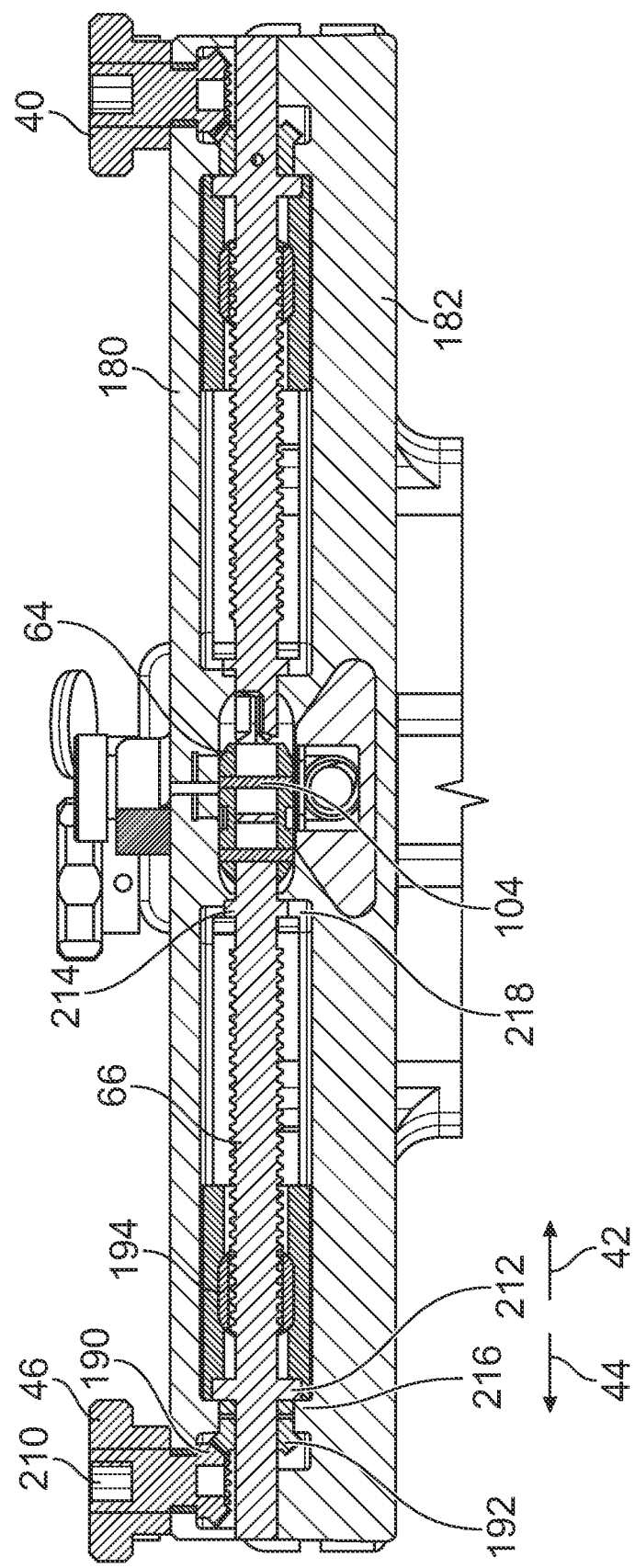
FIG. 10 is a cross-sectional view taken across 10-10 in FIG. 8 showing bevel gears of the knobs engaged with bevel gears of the drive shafts.

Regarding FIGS. 3 and 10, the frame 12 has a frame upper body 180 and a frame lower body 182. In FIG. 3, the frame upper body 180 is removed to show components of the drives 30, 32, 34. The drive 30 includes a drive member including a bevel gear 190 and the knob 46 such that turning of the knob 46 causes turning of the bevel gear 190. The drive 30 further includes a bevel gear 192 mounted on the drive shaft 66 and engaged with the bevel gear 190 such that turning of the knob 46 causes turning of the drive shaft 66. The drive 34 has a similar arrangement of engaged bevel gears as shown in FIG. 10. The drive 30 further includes a nut 194 of the lateral slider 22 that engages threads of the drive shaft 66. Regarding FIG. 12, the nut 194 has a threaded portion 196 engaged with threads 198 of the drive shaft 66. The nut 190 includes an unthreaded wall portion 200 that is on an opposite side of a nut opening 202 through which the shaft 66 extends. The nut 194 further includes a quick release button portion 204. The slider 22 includes a spring 206 that urges the nut 194 in direction 208 which engages the threaded portion 196 of the nut 194 with threads 198 of the drive shaft 66. With the threaded portion 196 and the threads 198 engaged, the slider 22 is inhibited from movement in directions 44, 42 without turning of the drive shaft 66. However, a surgeon may press the quick release button portion 204 in direction 210 which shifts the threaded portion 196 of the nut 194 away from the threads 198 to disengage the threaded portion 196 from the threads 198.

Figure 12:
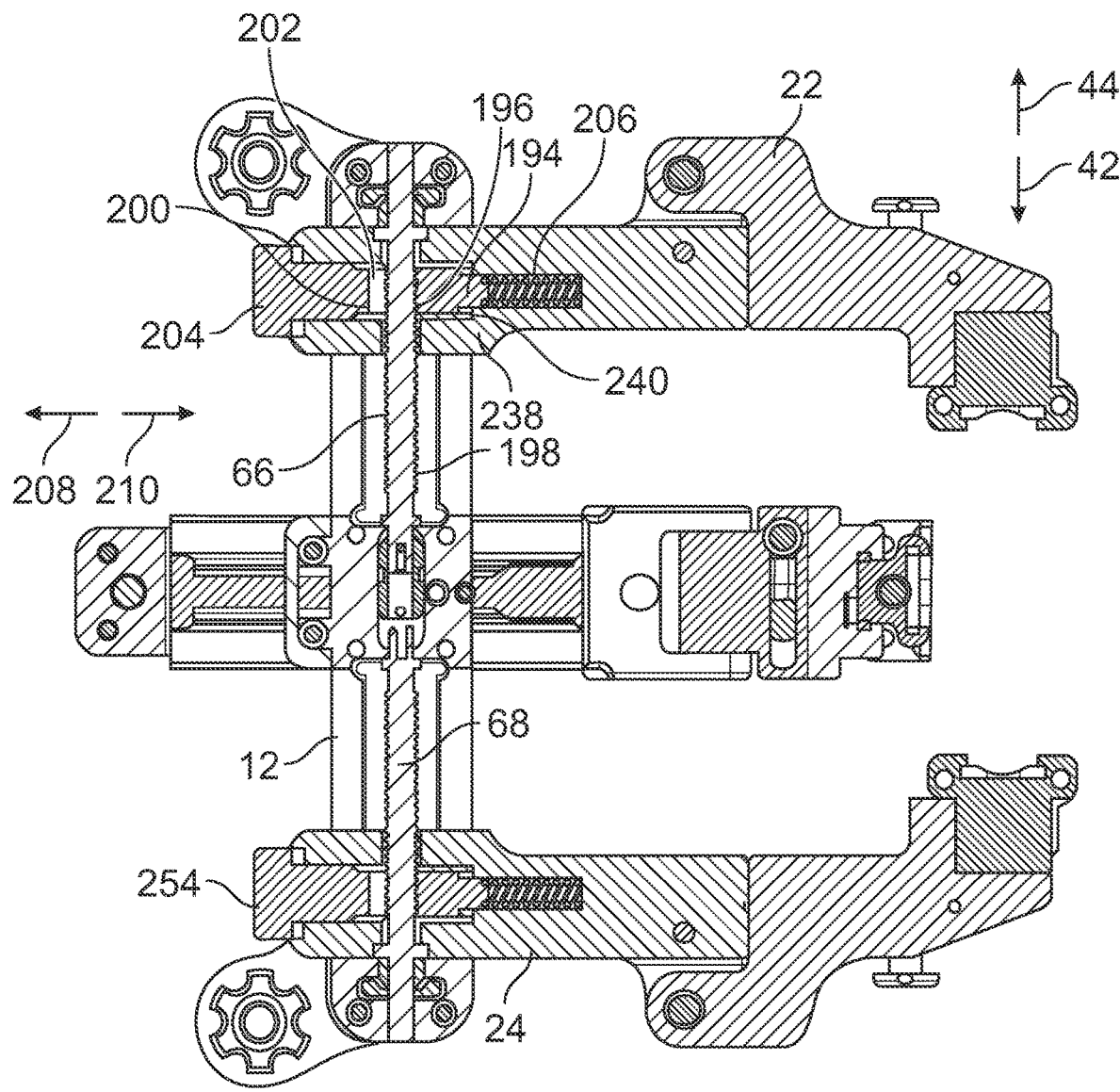
FIG. 12 is a cross-sectional view taken across line 12-12 in FIG. 9 showing threaded nuts of the sliders that are spring biased into engagement with the drive shafts.

With the quick release button portion 204 depressed, the lateral slider 22 may be freely shifted in direction 42 or 44. The lateral slider 24 has a similar nut 205 releasably engaged with the drive shaft 68 as shown in FIG. 12.

Regarding FIG. 10, to shift the slider 22 in directions 42, 44 relative to the frame 12 via the knob 46, a user turns the knob 46 such as by a driver tool connected to a drive structure 210 of the bevel gear 190. The drive shaft 66 has collars 212, 214 positioned against walls 216, 218 to constrain axial movement of the drive shaft 66. However, turning of the bevel gear 190 causes turning of the bevel gear 192 and shaft 66. The threaded engagement between the nut 194 and the shaft 66 causes the nut 194 to shift in direction 44 or 42 depending on the direction of rotation of the bevel gear 190. Regarding FIGS. 2 and 3, the slider body 120 of the slider 22 forms a slide connection 230 with the frame 12 to limit movement of the slider 22 to axial movement along the frame 12. In one embodiment, the slide connection 230 includes mating features of the frame upper and lower bodies 180, 182 and the slider body 120. For example, the slider body 120 may include channels 232 that receive rail portions 234 of the frame upper and lower bodies 180, 182. Regarding FIG. 12, shifting of the nut 194 in directions 42, 44 due to the turning of the drive shaft 66 presses the nut 194 against surfaces 238 of a pocket 240 of the slider body 120 and causes the slider body 120 to shift with the nut 194 in direction 42, 44.

Figure 15:
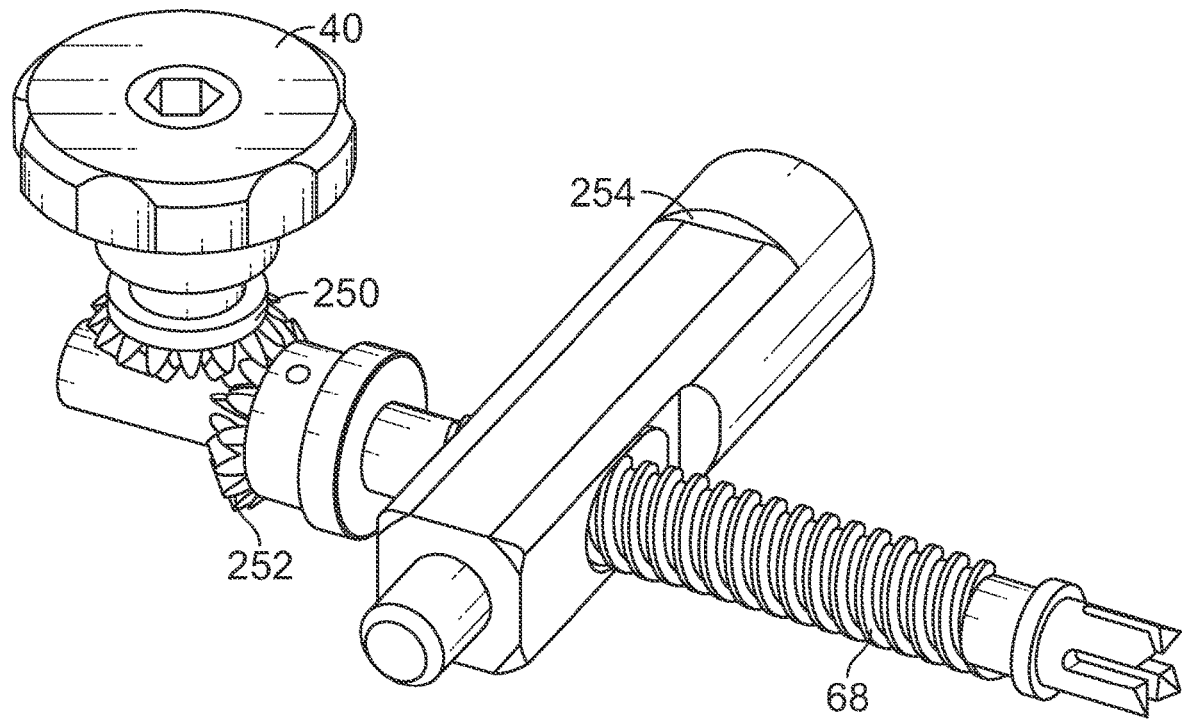
FIG. 15 is a perspective view of the threaded nut of one of the lateral sliders engaged with the associated drive shaft.

Regarding FIG. 15, the drive 34 is similar to the drive 30 discussed above. For example, the knob 40 is connected to the drive shaft 68 via bevel gears 250, 252. The slider 24 includes the nut 254 threadingly engaged with the shaft 68.

Figure 13:
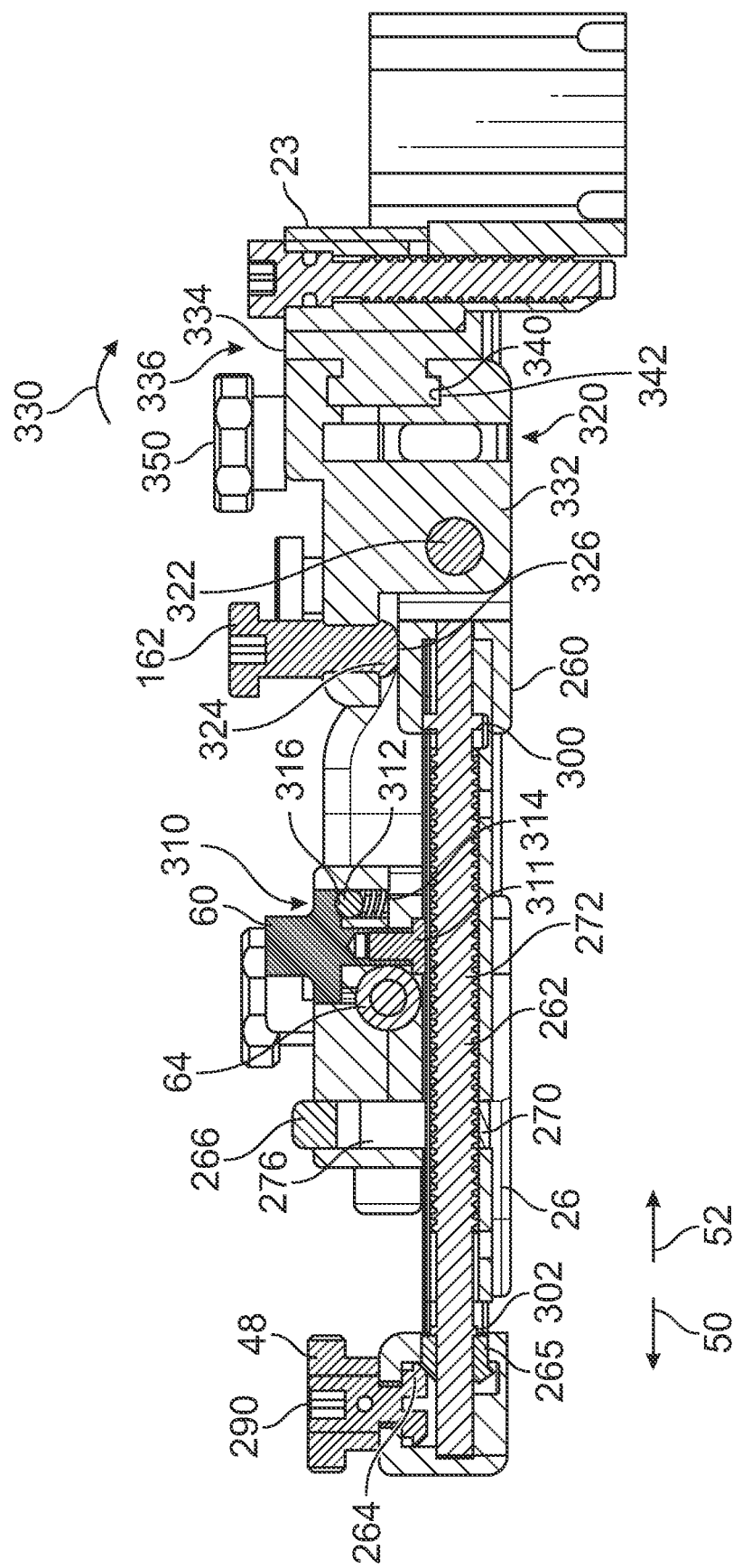
FIG. 13 is a cross-sectional view taken across line 13-13 in FIG. 8 showing a blade support of the medial slider that permits pivoting of the associated blade.
Figure 16:
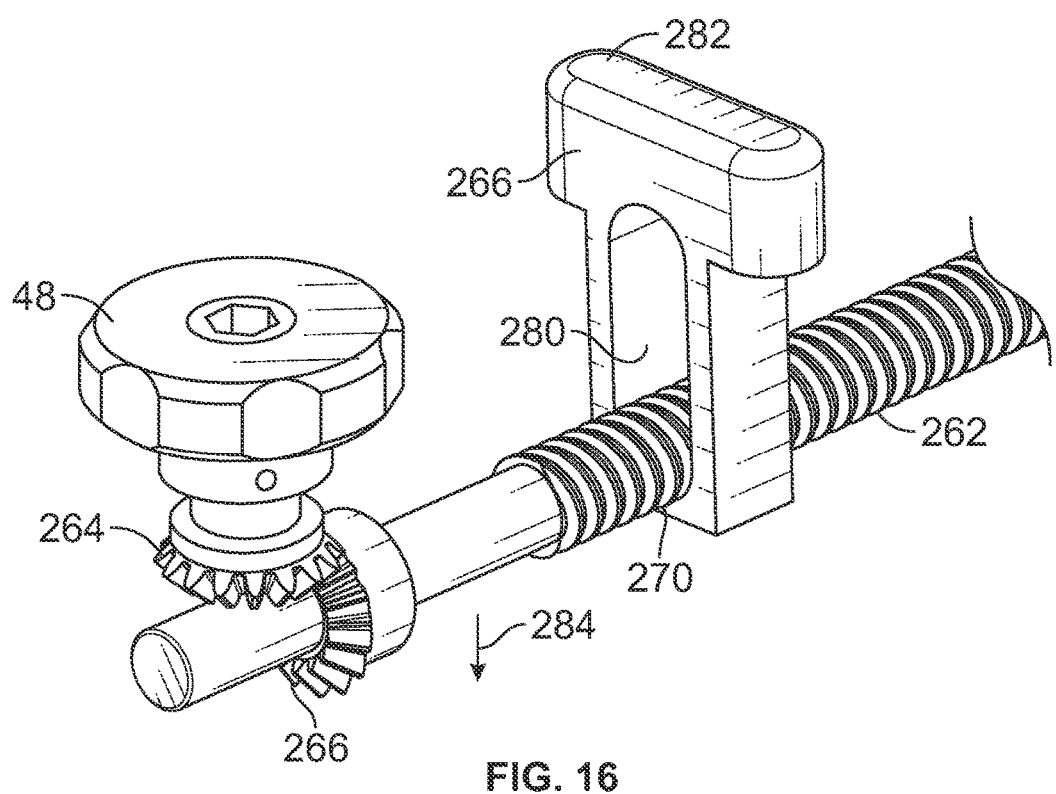
FIG. 16 is a perspective view of a nut of a medial slider having an elongated opening that permits the nut to be disengaged from the threads of the drive shaft of the medial slider by shifting the nut downwardly.

Regarding FIG. 13, the medial slider 26 has a slider body 260 supporting a drive shaft 262 of the drive 32. The drive 32 further includes bevel gears 264, 265 that operate to translate rotation of the knob 48 into rotation of the shaft 262. The frame 12 includes a nut 266 having a threaded portion 270 engaged with threads 272 of the drive shaft 262. Regarding FIG. 3, the nut 266 is biased upward by springs 274 to engage the threaded portion 272 with the drive shaft 262. The drive shaft 262 extends through a vertically elongated opening 276 of the nut 266 and the nut 266 has unthreaded surfaces 280 (see FIG. 16) on opposite sides of the drive shaft 262. Regarding FIG. 16, the nut 266 has a quick release button portion 282 that may be pressed to shift the nut 266 in direction 284 against the bias of the springs 274 and disengage the threaded portion 270 of the nut 266 from the drive shaft 266. With the threaded portion 270 disengaged from the drive shaft 266, the slider 26 may be shifted in directions 50, 52 without rotation of the drive shaft 262. The quick release button portion 282 may thereby operate a quick disconnect to permit positioning of the medial slider 26 relative to the frame 12.

To move the slider 26 in directions 50, 52 using knob 48, the user turns the knob 48 by grasping the knob 48 or connecting a tool to the drive structure 290 of the knob 48 to turn the bevel gears 264, 265 and the drive shaft 262. Due to the threaded engagement between the shaft 262 and the nut 266, and the nut 266 being supported in the frame 12, turning of the shaft 262 causes axial shifting of the shaft 262 in directions 50, 52. The shaft 262 has a collar 300 contacting the slider body 260 and a collar 302 contacts the bevel gear 266 to urge the slider body 260 to move axially in directions 50, 52. In this manner, the shaft 262 moving in axial direction 50, 52 is translated into shifting of the slider 26 in directions 50, 52.

Regarding FIG. 13, the frame 12 includes a detent mechanism 310 to resist unintended movement of the switch 60 from the positions of FIG. 4 and FIG. 6. In one embodiment, the detent mechanism 310 includes a ball 312 biased by a spring 314 into a recess 316 on the underside of the switch 60. There may be two recesses 316, one for each position of the switch 60. The frame 12 may further include a plug 311 that is connected to the switch 60 to rotatably capture the switch 60 in the frame 12.

Regarding FIG. 13, the slider 26 includes an arm portion 320 pivotally connected to the slider body 260 by a pin 322. Turning of the fastener 162 presses an end portion 324 of the fastener 162 against a surface 326 of the slider body 260 pivots the arm portion 320 in direction 330. The tension of the tissue retracted by the blade 22 urges the blade 22 and the arm portion 320 in a direction opposite direction 330 which keeps the end portion 324 of the fastener 162 firmly contacting the surface 326 during a retraction operation.

Regarding FIG. 13, the arm portion 320 includes a blade support body 332, a blade holder 334, and a slide connection 336 therebetween. In one embodiment, the slide connection 336 includes a dovetail projection 340 of the blade holder 334 received in a dovetail recess 342 of the blade support body 332. Regarding FIGS. 8, 13, 17, the medial blade translation mechanism 160 includes a knob 350 connected to a shaft 352 having threads 354 and a geared lever 356 engaged with the threads 354. The geared lever 356 includes a first arm portion 358 having threads 360 engaged with threads 354 of the shaft 352 and a second arm portion 362 having an elongated opening 364 that receives a pin 366 of the blade holder 334. The gear lever 356 is pivotally connected to the blade support body 332 by a pin 368. Turning of the knob 350 causes turning of the shaft 352 and pivoting of the geared lever 356 in directions 370, 372 and associated translation of the blade holder 334 in directions 374, 376. Regarding FIG. 17, the blade holder 334 may include a recess 380 that receives a projection 382 (see FIG. 8) of the blade 22.

Figure 14:
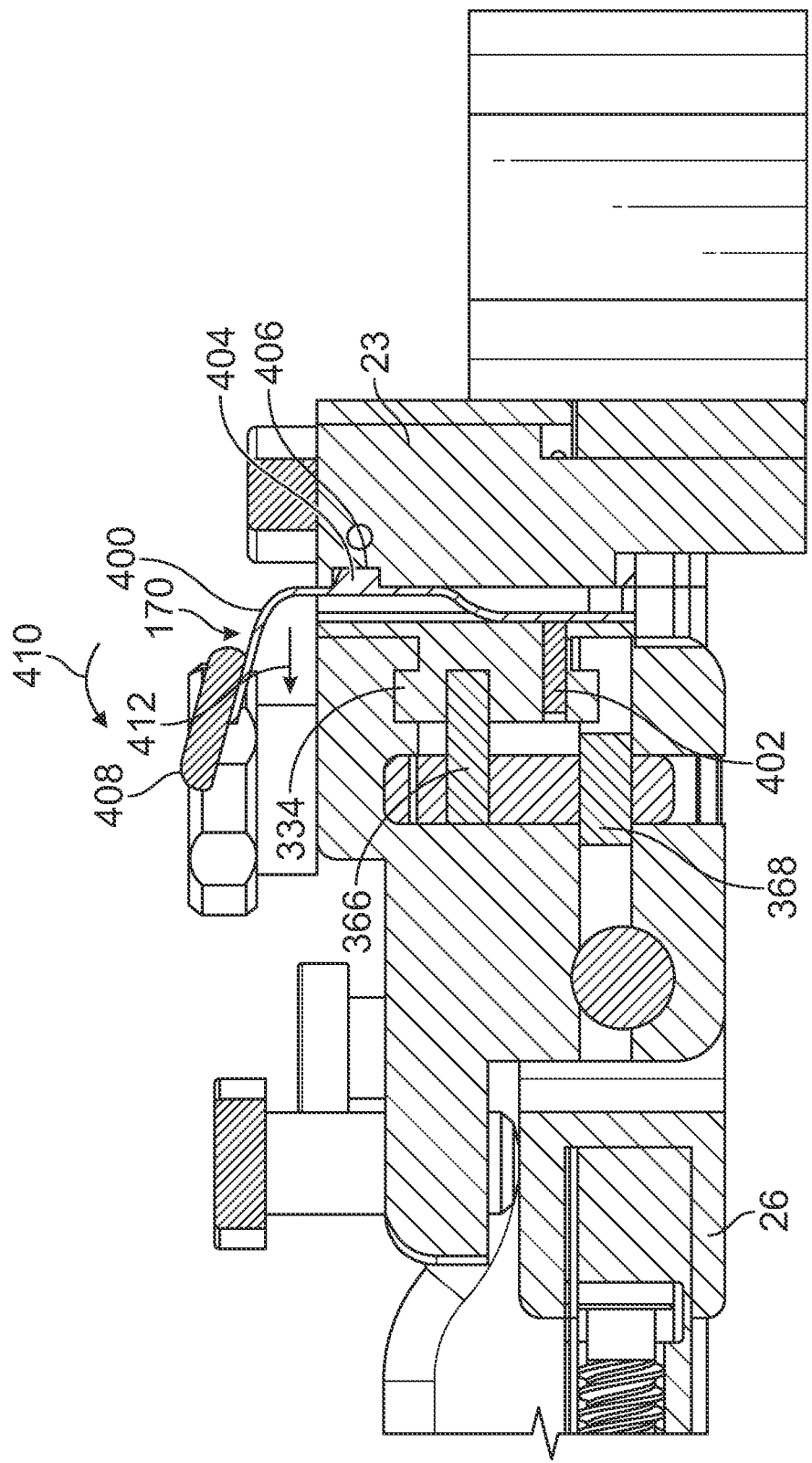
FIG. 14 is a cross-sectional view taken across line 14-14 in FIG. 8 showing a slide connection between a blade holder and a blade support body of the blade support of FIG. 13 that facilitates translational movement of the blade.

Regarding FIG. 14, to retain the blade 22 in the blade holder 334, the slider 26 includes the retainer 170. The retainer 170 has a spring 400 that is connected to the blade holder 334 by a pin 402. The spring 400 further includes an engagement portion, such as a barb 404, that engages a groove 406 of the blade 22. The spring 400 resiliently urges the barb 404 into the groove 406 once the blade 22 has been slid onto the blade holder 334. To disengage the blade 22 from the blade holder 334, a user presses a release button 408 of the retainer 170 in direction 410 which shifts the spring 400 generally in direction 412 and disengages the barb 404 from the groove 406.

Figure 19:
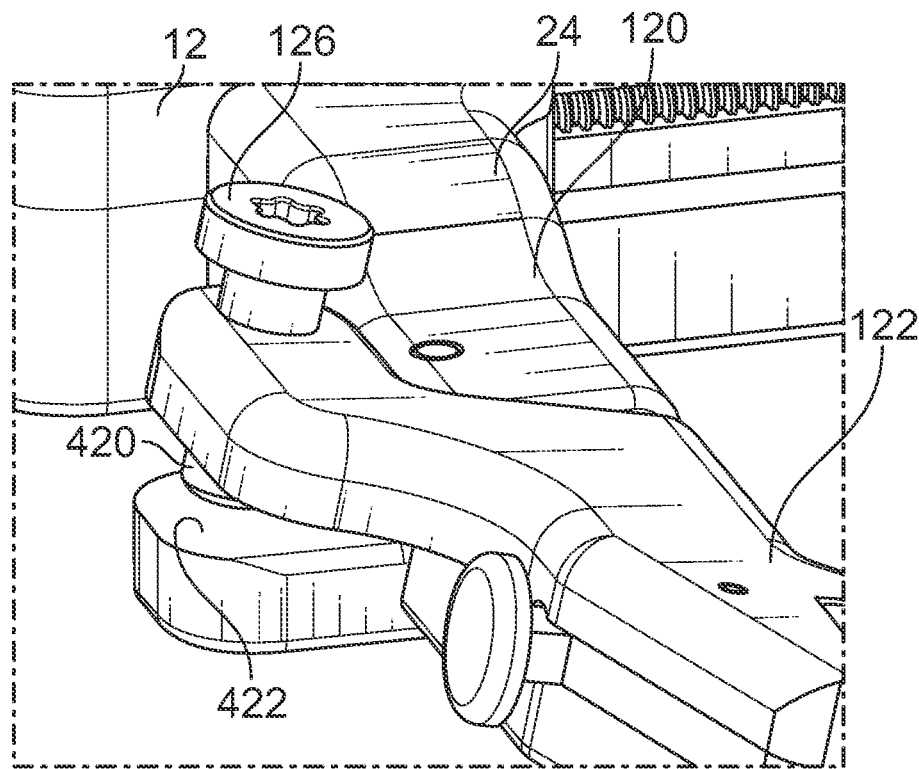
FIG. 19 is a perspective view of a portion of a lateral slider showing a fastener of the slider pivoting an arm of the slider.
Figure 20:
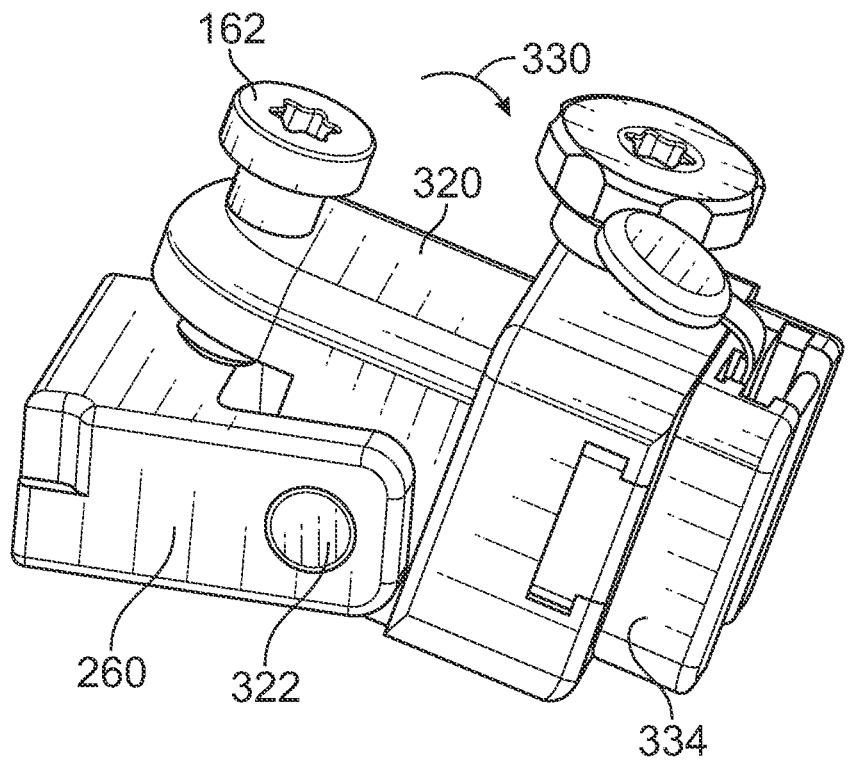
FIG. 20 is a view of a portion of the medial slider showing a fastener of the medial slider pivoting the blade support body relative to a slider body.

Regarding FIG. 19, a surgeon may toe out the blades 18, 20 connected to the sliders 22, 24 by turning a fastener 126 of the associated sliders 22, 24. The arm 122 may be pivotally connected to the slider body 120. The fastener 126 has an end portion 420 that contacts a surface 422 of the slider body 120 to pivot the arm 122 relative to the slider body 120.

With reference to FIGS. 21-30, a method of connecting a retractor 10 to a bone 500 is shown. The retractor 10 may be connected to the bone 500 to provide stability of the retractor 10 relative to the bone 500. Regarding FIG. 21, an adapter 502 is provided that includes an adapter body 504 for connecting to a bone screw 506 and a locking member, such as a set screw 508. The bone screw 506 has a head portion 510 with a partially spherical outer surface 512 and a rotary drive structure, such as a drive recess 514. The bone screw 506 further includes a shank portion 514 depending from the head portion 510.

The adapter body 504 includes a pocket 519 to receive at least a portion of the bone screw head portion 510. For example, the adapter body 504 includes side wall 520 extending about an interior 521 sized to receive the bone screw head portion 510. In one embodiment, the side wall 520 includes an opening 522 sized to receive the head portion 510. The opening 522 has a lateral portion 522A to permit the bone screw head portion 510 to be advanced laterally into the interior 521 and a lower portion 522B sized to permit the bone screw 506, such as a neck and/or shank portion 514 thereof, to extend therethrough while inhibiting the head portion 510 from advancing through the lower portion 522B. The side wall 520 has a collar portion 520A extending about the lower portion 522B of the opening 522. The collar portion 520A engages a lower side of the head portion 510 when the set screw 508 engages an upper side of the head portion 510.

Regarding FIG. 23, the interior 522 includes a surface 524 for contacting a lower portion of the partially spherical surface 512. The surfaces 512, 524 cooperate to form a portion of the ball-and-socket connection between the adapter body 504 and the bone screw 506. The set screw 508 has a clamping portion 530 with an annular portion 531 having a surface 532 configured to engage an upper portion of the partially spherical surface 512.

The adapter body 504 has a longitudinal axis 593 (see FIG. 24) that is coaxial with a central axis of the set screw 508. Regarding FIG. 21, the head portion 510 is advanced laterally in direction 536 into the interior 522 and the set screw 508 is tightened down using a set screwdriver 540. The turning of the set screwdriver 540 causes the bone screw head portion 510 to be clamped between the surfaces 532, 524 of the set screw 508 and the adapter body 504. In this manner, the complementary surfaces of 532, 524, 512 form a ball-and-socket connection 550 that permits relative pivoting of the adapter body 508 and the bone screw 506 prior to final locking of the set screw 568. However, when the set screw 508 is tightened down, the adapter body 504 is fixed relative to the bone screw 506.

With reference to FIG. 23, the set screwdriver 540 has an inner shaft 540A with a distal end portion configured to engage the rotary drive structure of the set screw 508. The set screwdriver 540 also has a retainer portion with an engaging configuration wherein the set screwdriver 540 secures the set screwdriver 540 to the adapter 502 and a release configuration wherein the set screwdriver 540 permits the set screwdriver 540 to be disconnected from the adapter 502. The retainer portion of the set screwdriver 540 includes an outer sleeve 540B having one or more protrusions 540C that are resiliently biased radially outward into a channel 508B below a lip 508A of the set screw 508. To shift the retainer from the engaging configuration to the release configuration, the protrusions 540 are shifted radially inward out of the channel 508B such that the drive structure of the inner shaft 540A may be withdrawn from the set screw 508.

Regarding FIG. 24, once the set screw 508 has been tightened down to temporarily hold the adapter body 504 relative to the bone screw 506, a blade connector portion, such as a U-shaped member 560 (see FIG. 21) and a U-shaped resilient member 560 connected thereto, is connected to a blade 562 (such as one of the blades 18, 20 discussed above). Regarding FIG. 21, the U-shaped member 560 includes a flange portion 564 that is slidably received in a channel 566 of the blade 562. The U-shaped member 560 has a lower end portion 568 that is seated against a lip 570 of the blade 562 at a distal end of a channel 562. The U-shaped member 560 has arms 560B with openings 560C and the resilient member 560A has detents 560D extending out of the openings 560C. The detents 560D engage recesses on the interior of the channel 566 and resist unintentional disengagement of the adapter 502 from the blade 562.

Figure 25:
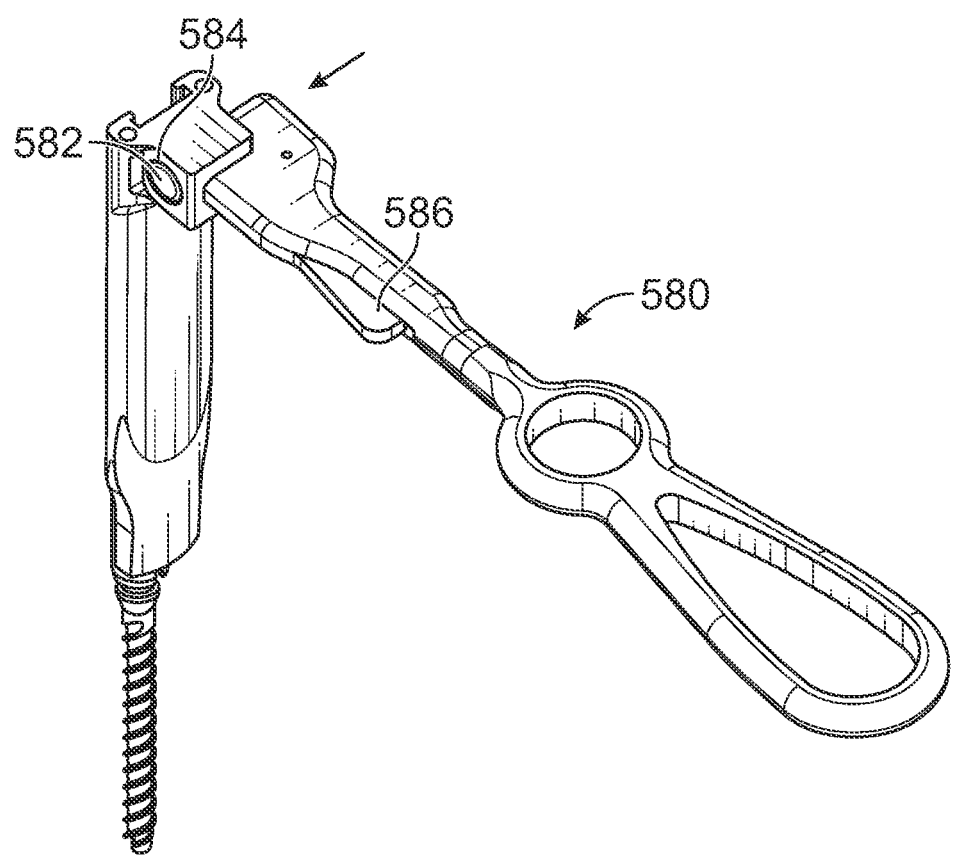

Regarding FIG. 25, a blade handle 580 may be connected to the blade 562. For example, the blade handle includes a boss 582 that extends through an opening 584 of the blade 562 and a tooth of the blade handle 580 is resiliently urged into an opening of the blade 562 to releasably connect the blade 562 to the blade handle 580. To disconnect the blade handle 580 from the blade 560, a user may press a release button 586 to disengage the blade 562 and slide the boss 582 out of the opening 584.

Figure 26:
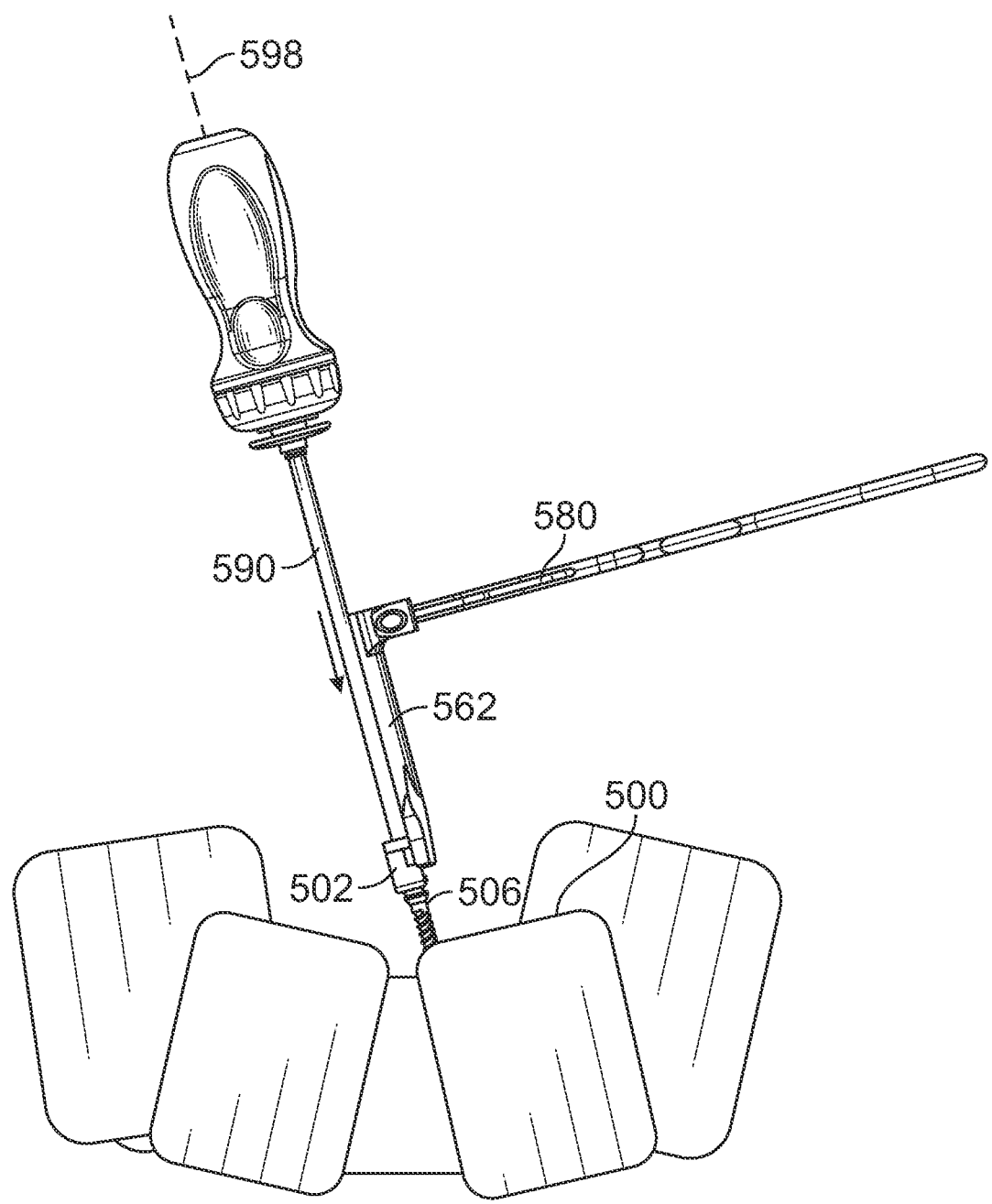

Regarding FIG. 26, a screwdriver 590 is advanced through an opening 592 (see FIG. 23) of the adapter 502 and engaged with a rotary drive structure 594 of the bone screw head portion 510. The driver 590, adapter 502, and bone screw 506 may be cannulated to permit the assembled screwdriver 590, adapter 502, and blade 562, and bone screw 506 to be slid down along a guide wire 598 toward the bone 500.

Figure 28:
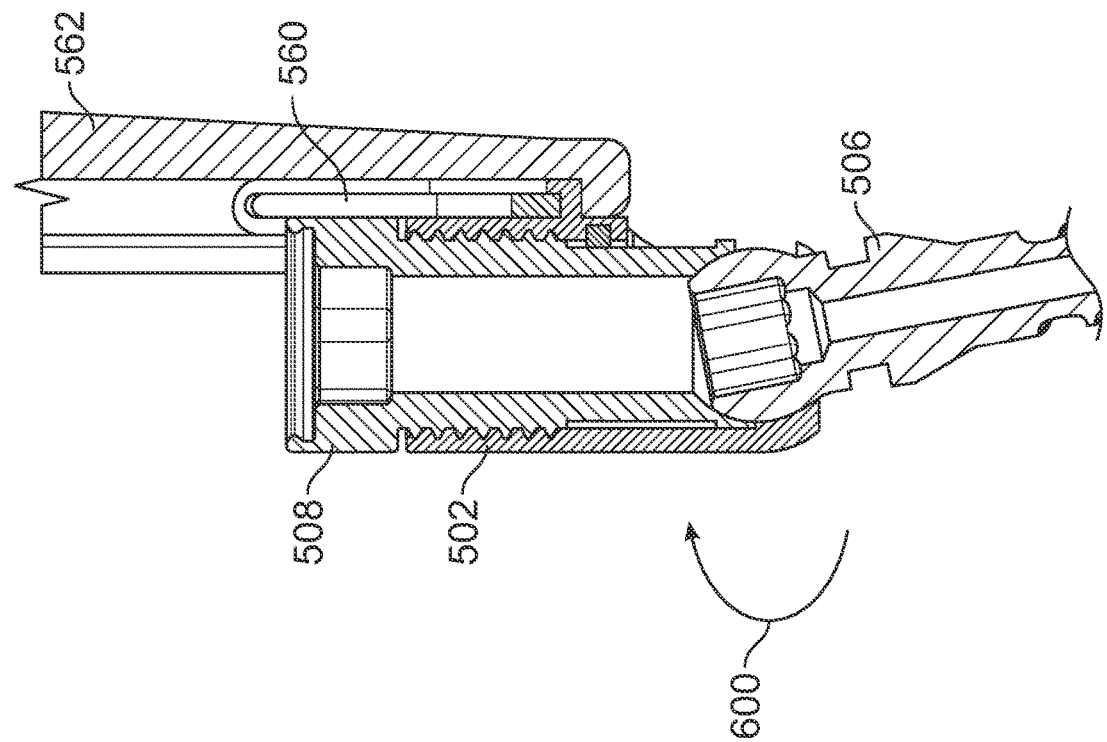
Figure 27:
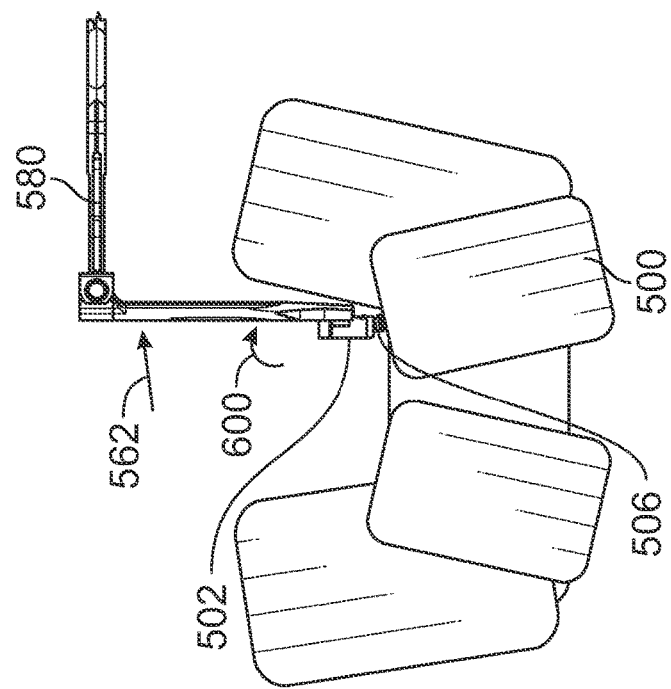
Figure 29:
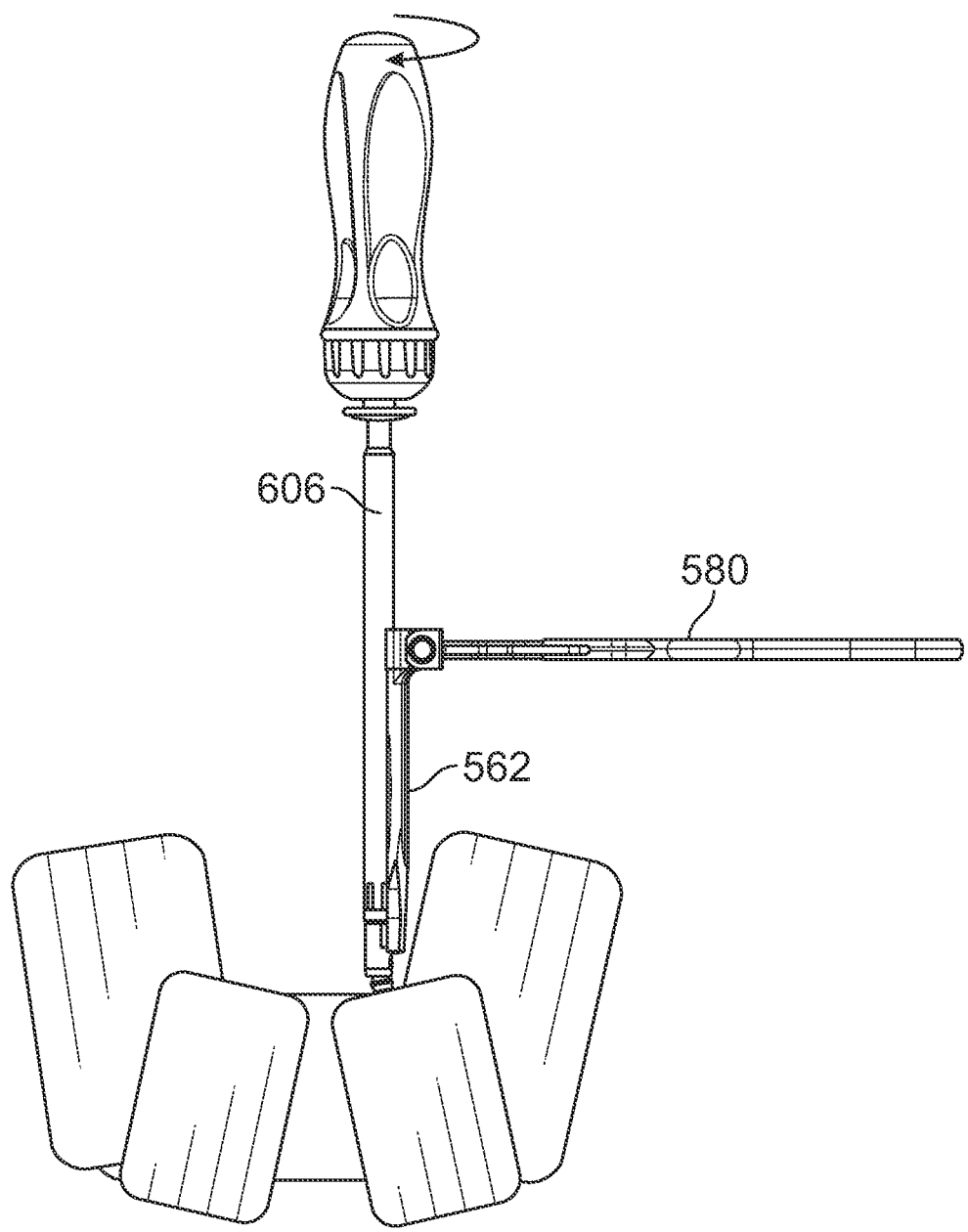

Regarding FIGS. 27 and 28, the screwdriver 590 has been used to drive the bone screw 506 into a bone 500 to the desired depth. Regarding FIG. 23, the set screwdriver 540 may have been used to partially tighten down the set screw 508 so that the adapter 502 may still be pivotal relative to the bone screw 506. The blade handle 580 may be pivoted in direction 600 (see FIG. 28) to pivot the blade 562 and adapter 502 in direction 600. As an alternative, the set screwdriver 540 may have fully tightened down the set screw 508 prior to the driving of the bone screw 506, and may be used subsequently to loosen the set screw 508 to permit pivoting of the adapter 502 relative to the bone screw 506. Once the adapter 502 is at the desired orientation relative to the bone screw 506, the set screw 508 may be fully tightened down with a set screw final tightener 606 as shown in FIG. 29. Once the set screw 508 has been fully tightened down to fix the adapter 502 to the bone screw 506, the set screw final tightener 606 may be removed and the blade handle 580 disconnected from the blade 562.

Figure 30:
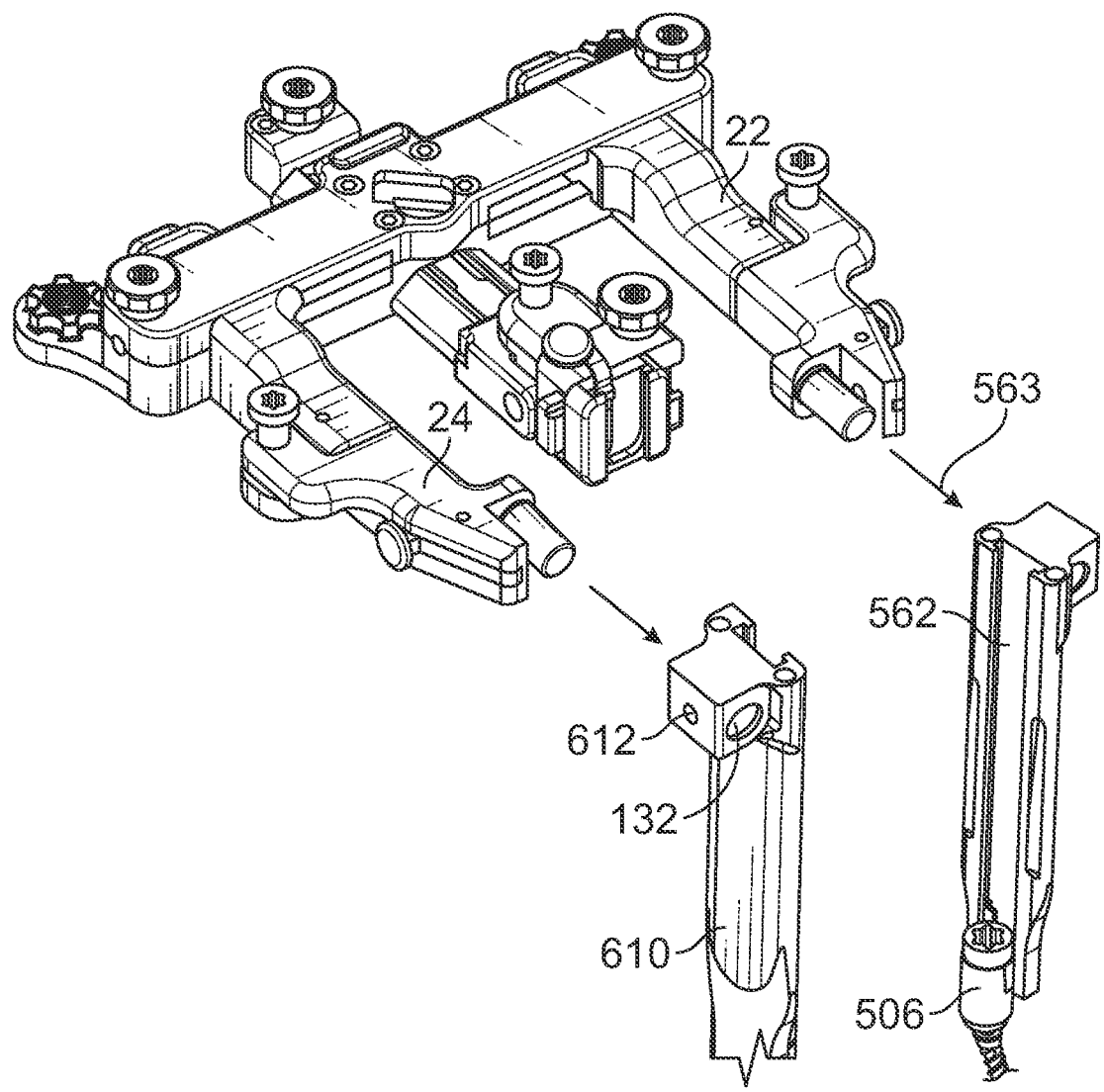
Figure 31:
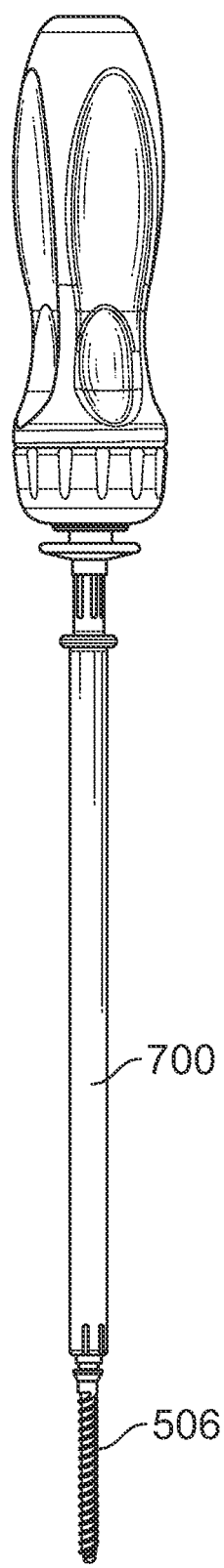
Figure 32:
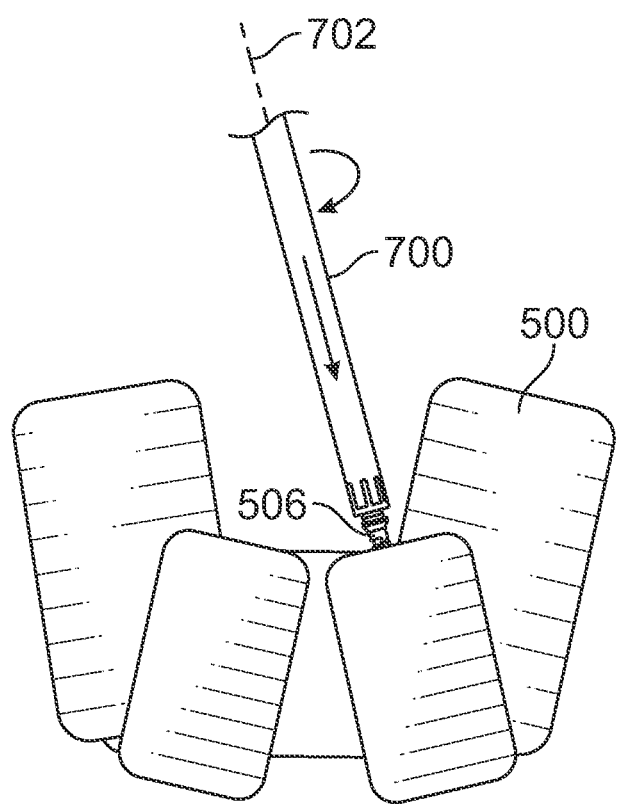

Regarding FIG. 30, the slider 22 of the retractor 10 may be connected to the blade 562 secured to the bone screw 506 by advancing the retractor 10 laterally relative to the blade 562 in direction 563. Another blade 610 may have been connected to bone or tissue. The bosses 130 of the sliders 22, 24 are advanced into the openings 132 of the blades 562, 610 and the teeth 140 of the latches 136 are resiliently snapped into openings 612 of the blades 562, 610 to connect the sliders 22, 24 to the blades 562, 610. In another approach, the sliders 22, 24 may be connected to the blades 562, 610 prior to final tightening of the set screws 508.

Regarding FIGS. 31-36, another method of connecting the retractor 10 to the bone 500 is provided. Regarding FIGS. 31 and 32, a driver 700 is first connected to the bone screw 506 to drive the bone screw 506 along a guide wire 702 into the bone 500. Regarding FIG. 33, the adapter 502 is then connected to the blade 562 via engagement between the U-shaped member 560 and the channel 566 of the blade 562. The blade holder 580 is connected to the blade 562 and a screwdriver 540 is connected to the set screw 508. Regarding FIG. 34, the assembled components are brought toward the bone screw 506 engaged with the bone screw 506. The adapter body 504 is shifted in direction 704 to position the interior 522 of the adapter body 504 onto the head portion 510 of the bone screw 506 to form the ball and socket connection 550 therebetween.

Figure 36:
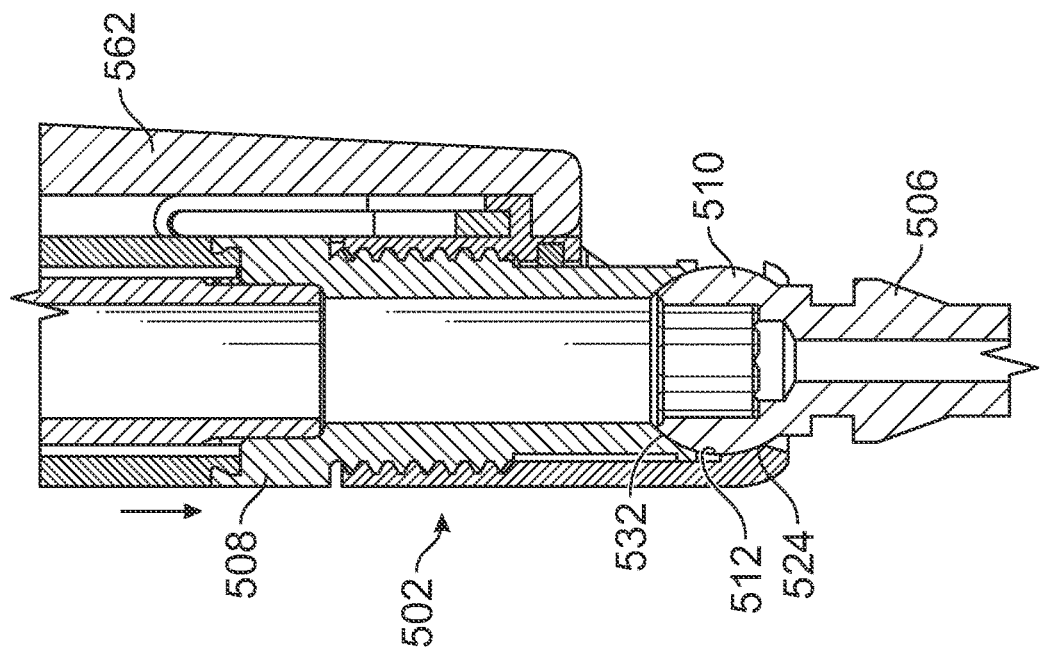
Figure 35:
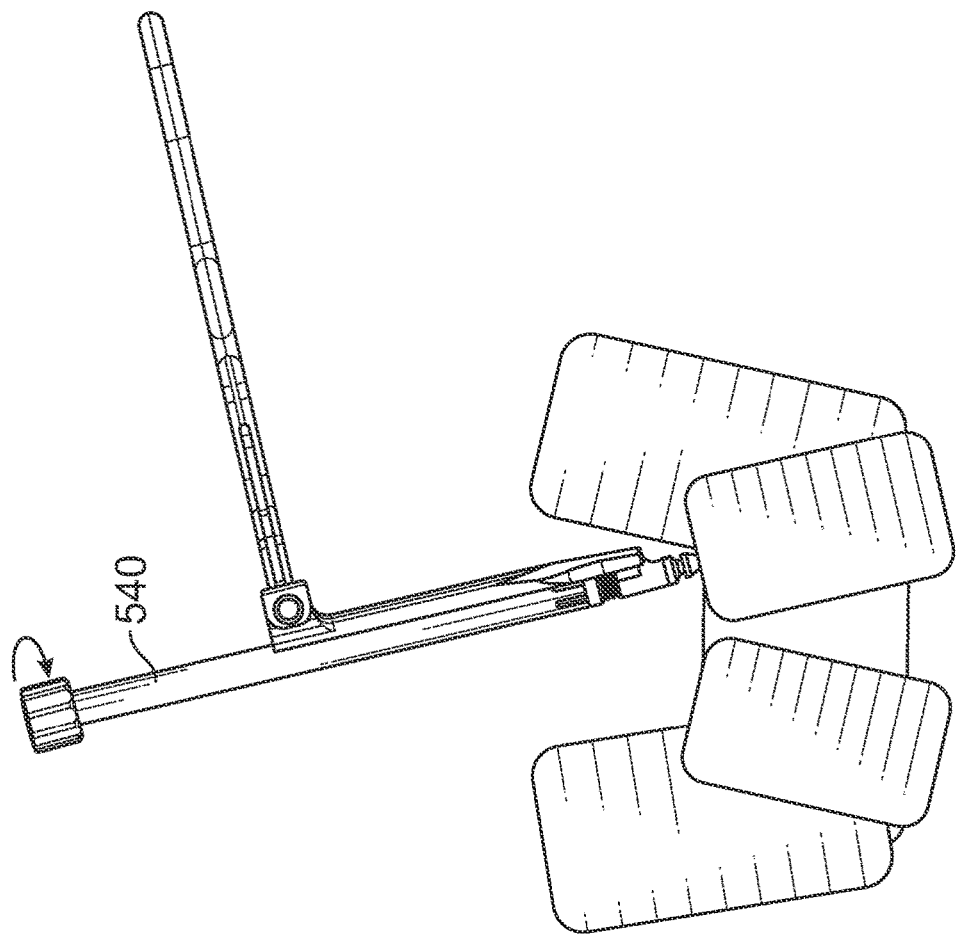

Regarding FIGS. 35 and 36, the set screwdriver 540 may be then turned to drive the set screw 508 against the head portion 510 and to tightly engage the surfaces 532, 512, 524 to form a final locking of the adapter 502 relative to the bone screw 506. With the adapter 502 fixed relative to the bone screw 506, the slider 22 may be connected to the blade 562. In an alternative approach, the slider 22 may be connected to the blade 562 prior to final tightening of the set screw 508.

Figure 37:
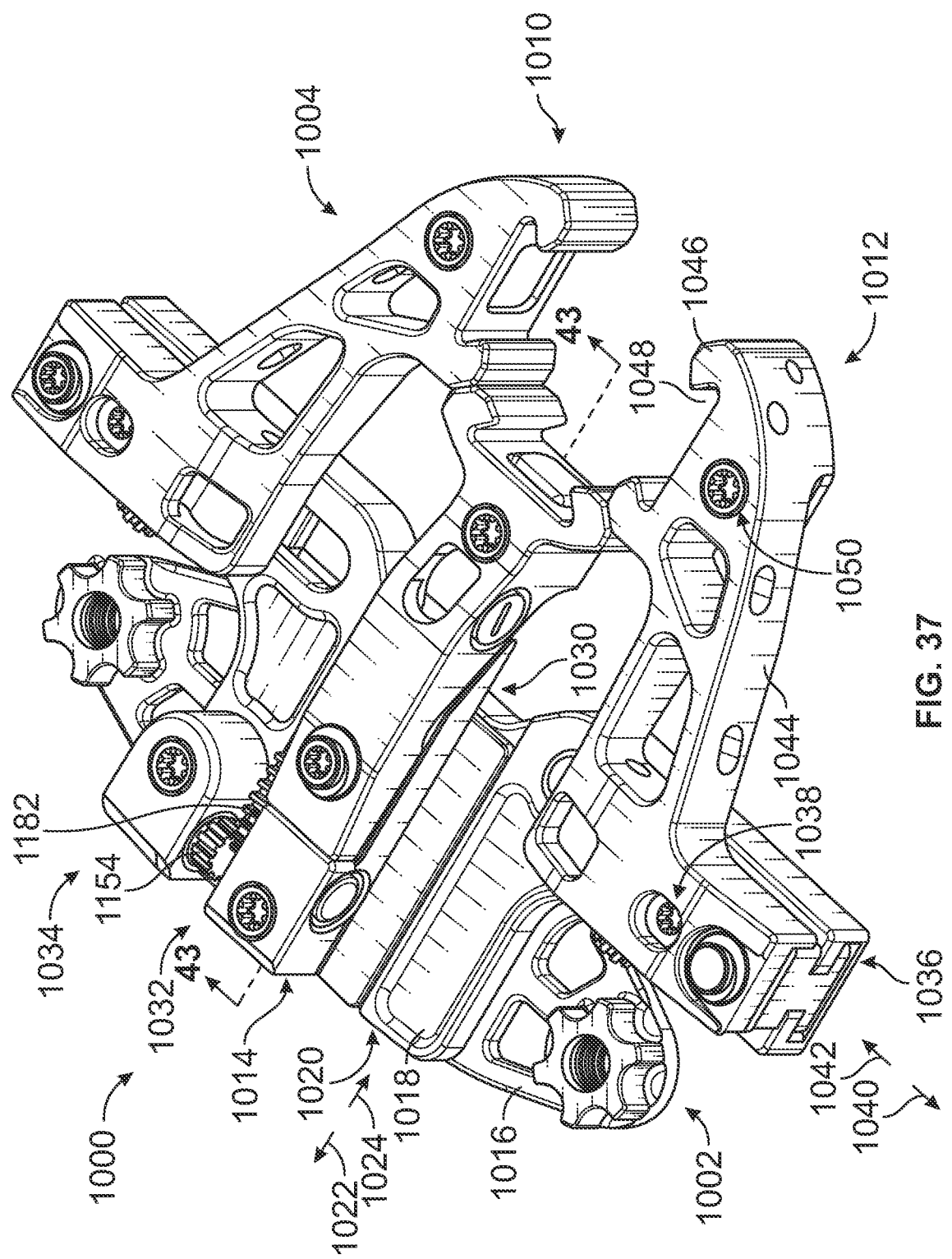
FIG. 37 is a perspective view of a retractor having sliders connected to a frame, the frame including a base frame and an intermediate frame that are movable relative to one another.

Regarding FIG. 37, a retractor 1000 is provided that may be used in a variety of surgical procedures including lateral access spinal surgery. The retractor 1000 is similar in many respects to the retractor 10 discussed above such that differences will be highlighted. The retractor 10 includes a frame 1002 and sliders 1004 for connecting blades 1006 (see FIG. 51) to the frame 1002. In one embodiment, the sliders 1004 include second and third sliders such as lateral sliders 1010, 1012 and a first slider such as a medial slider 1014. The frame 1002 includes a plurality of portions, such as a base frame 1016 and an intermediate frame 1018, that may move relative to one another. In one embodiment, the base frame 1016 and the intermediate frame 1018 have a slide connection 1020 therebetween that permits the intermediate frame 1018 to shift in directions 1022, 1024 relative to the base frame 1016. The base frame 1016 and the medial slider 1014 also include a slide connection 1030 therebetween that permits the medial slider 1014 to shift relative to the base frame 1016 in directions 1022, 1024. The medial slider 1014 includes a medial slider drive 1032 that may be operated to shift the medial slider 1014 in directions 1022, 1024 and the intermediate frame 1018 includes a frame drive 1034 that may be operated to shift the intermediate frame 1018 relative to the base frame 1016 in directions 1022, 1024. Each lateral slider 1010, 1012 includes a slide connection 1036 with the intermediate frame 1018 and a lateral slider drive 1038 that may be operated to shift the lateral slider 1012, 1014 in directions 1040, 1042. Each lateral slider 1010, 1012 also includes an arm 1044, a blade holder portion 1046 that may include a recess 1048 that receives the projection of one of the blades 1006, and a blade locking mechanism 1050 for securing the blade 1006 to the slider 1010, 1012.

Regarding FIGS. 38 and 39, the base frame 1016 includes an attachment portion 1059 that may include threads or other structures for securing the base frame 1016 to a support, such as an iron intern. The base frame 1016 includes a recess 1060 having a narrow portion 1062 and enlarged portion 1064. The enlarged portion 1064 receives a projection 1066 (see FIG. 42) of a body 1068 of the medial slider 1014. The base frame 1016 includes a pair of upper portions 1070, 1072 on opposite sides of the recess 1060. The upper portion 1070 includes flange portions 1074, 1076 extending in opposite directions and a rack 1077 having teeth 1078 upstanding from the upper portion 1070. The base frame 1016 further includes a wall 1080 that defines a part of a recess 1082 on an opposite side of the wall 1080 from recess 1060. The upper portion 1072 further includes flange portions 1084, 1086 extending in opposite directions and a wall 1088 that defines a part of a recess 1090. The recesses 1082, 1090 receive flange portions 1092, 1094 (see FIG. 40) of the intermediate frame 1018. The engaged flange portions 1074, 1086, 1092, 1094 and the walls 1080, 1088 may constrain the intermediate frame 1018 to linear movement relative to the base frame 1016.

Figure 40:
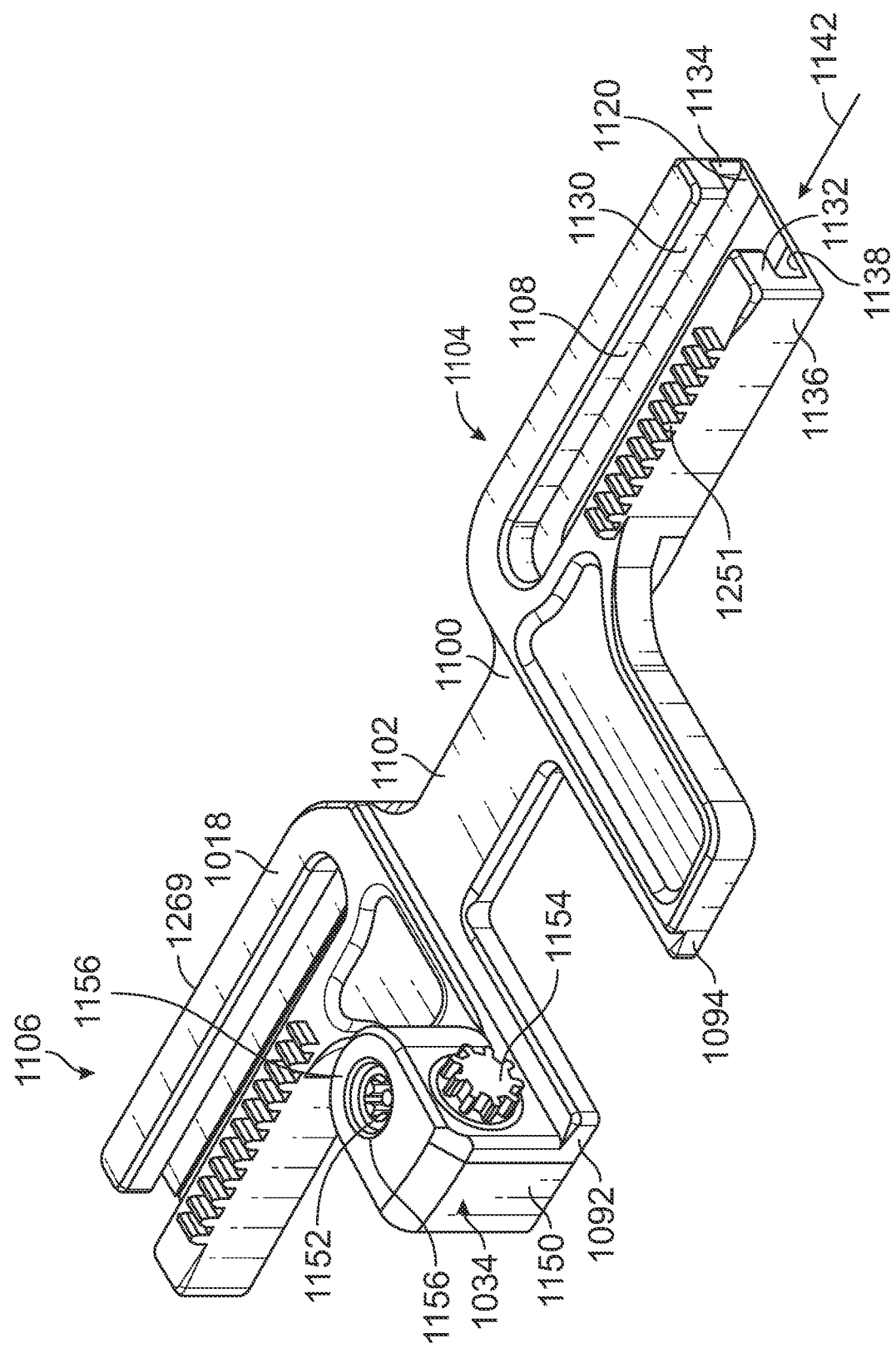
FIG. 40 is a perspective view of the intermediate frame of FIG. 37 showing a drive of the intermediate frame that engages teeth of the base frame to shift the intermediate frame relative to the base frame, the intermediate frame further including recesses that receive the lateral sliders.

Regarding FIG. 40, the intermediate frame 1018 includes a body 1100 having a transverse portion 1102 and slider support portions 1104, 1106 extending away from the transverse portion 1102. Each slider support portion 1104, 1106 includes a recess 1108 having an enlarged lower portion 1120 that receives a projection 1122 (see FIG. 44) of a body 1124 of a respective lateral slider 1010, 1012. Each slider support portion 1104, 1106 includes flange portions 1130, 1132, side walls 1134, 1136 and a floor 1138. The slider support portions 1104, 1106 each include an opening 1140 that permits the projection 1122 of one of the lateral sliders 1010, 1012 to be advanced in direction 1142 into the recess 1108 to connect the lateral slider 1010, 1012 to the slider support portion 1104, 1106.

Figure 41:
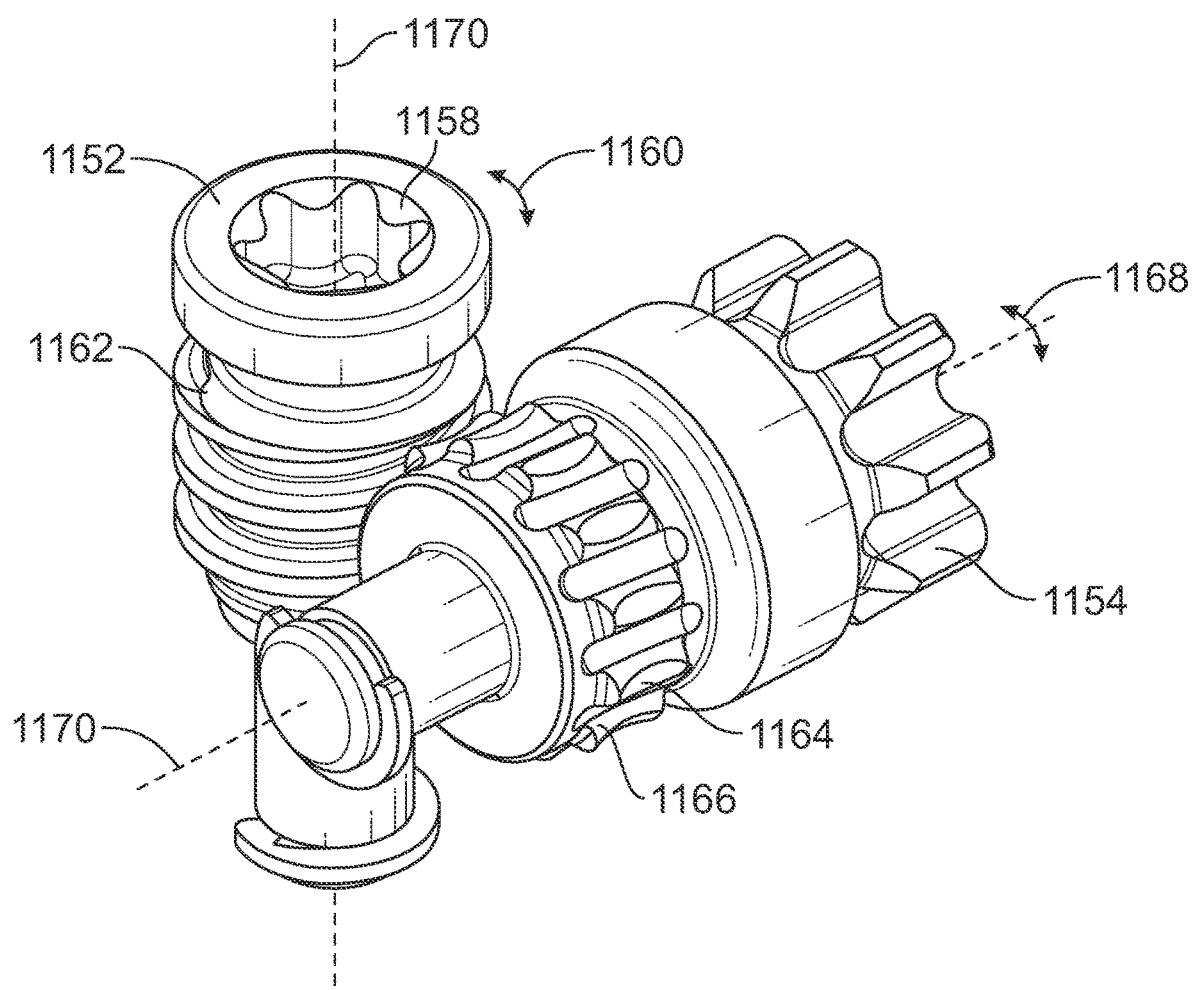
FIG. 41 is a perspective view of a worm screw and a pinion gear of the frame drive of FIG. 40.

Regarding FIGS. 40 and 41, the frame drive 1034 includes a housing 1150, a worm screw 1152, and a pinion gear 1154. The housing 1150 includes an opening 1156 that permits a user to insert a driver into a rotary drive structure 1158 of the worm screw 1152 and to turn the worm screw 1152 in directions 1160. The worm screw 1152 includes threads 1162 that are engaged with teeth 1164 of a worm gear 1166. The worm gear 1166 is connected to the pinion gear 1154 such that turning of the worm screw 1152 in directions 1160 causes associated turning of the pinion gear 1154 in directions 1168. In one embodiment, the worm gear 1166 and pinion gear 1154 are provided as a unitary one-piece rotatable member. The worm screw 1152 and the pinion gear 1154 are each rotated about respective axes 1170, 1172 with the axes 1170, 1172 extending perpendicularly to one another. The thread 1162 and teeth 1164 may be configured to be self-locking so that frictional engagement between the threads 1162 and teeth 1164 inhibits unintended turning of the pinion gear 1154. Regarding FIG. 40, the pinion gear 1154 engages teeth 1078 of the base frame 1116 to drive the intermediate frame 1018 relative to the base frame 1016 upon turning of the worm screw 1152.

Figure 42:
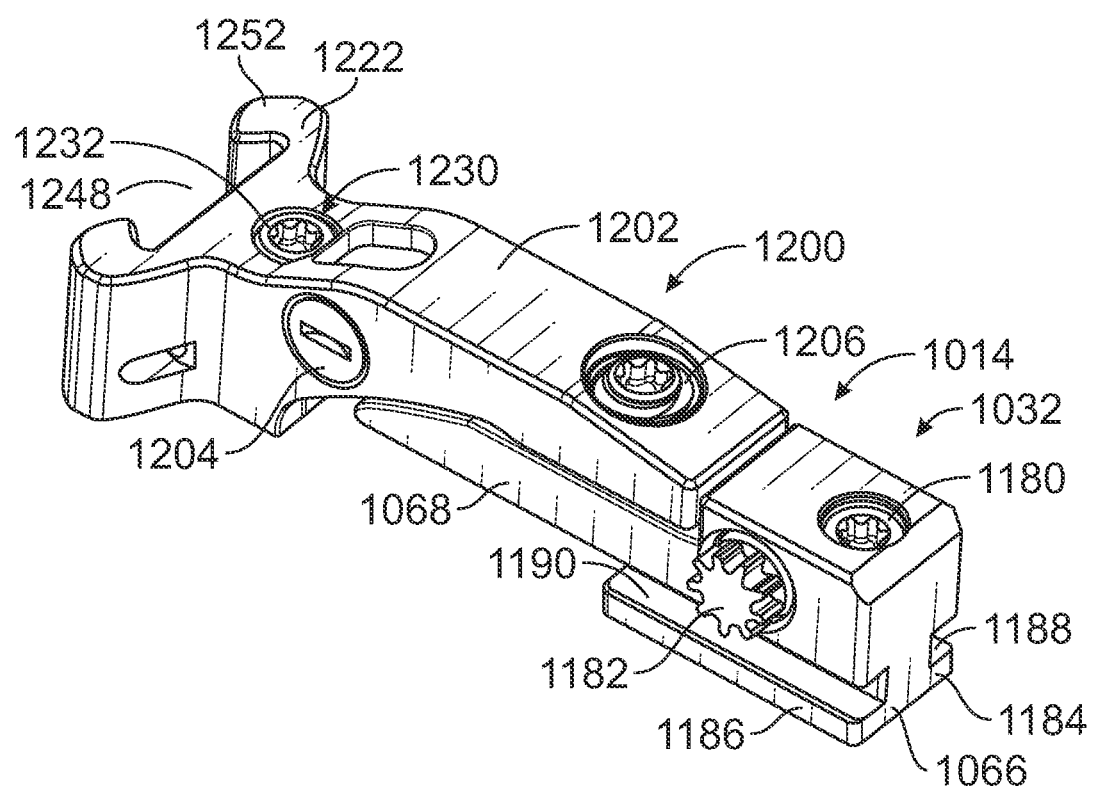
FIG. 42 is a perspective view of the medial slider of FIG. 37 showing a body of the slider with a projection that is received in the base frame central recess of FIG. 39 and an arm portion pivotally connected to the body for receiving a blade.

Regarding FIG. 42, the medial slider drive 1032 is similar to the frame drive 1034 discussed above and includes a worm screw 1180 that may be turned to cause rotation of a pinion gear 1182 operably coupled thereto. The projection 1066 of the body 1068 includes flange portions 1184, 1186 and channels 1188, 1190 that mate with the flange portions 1076, 1084 of the base frame 1016.

Figure 43:
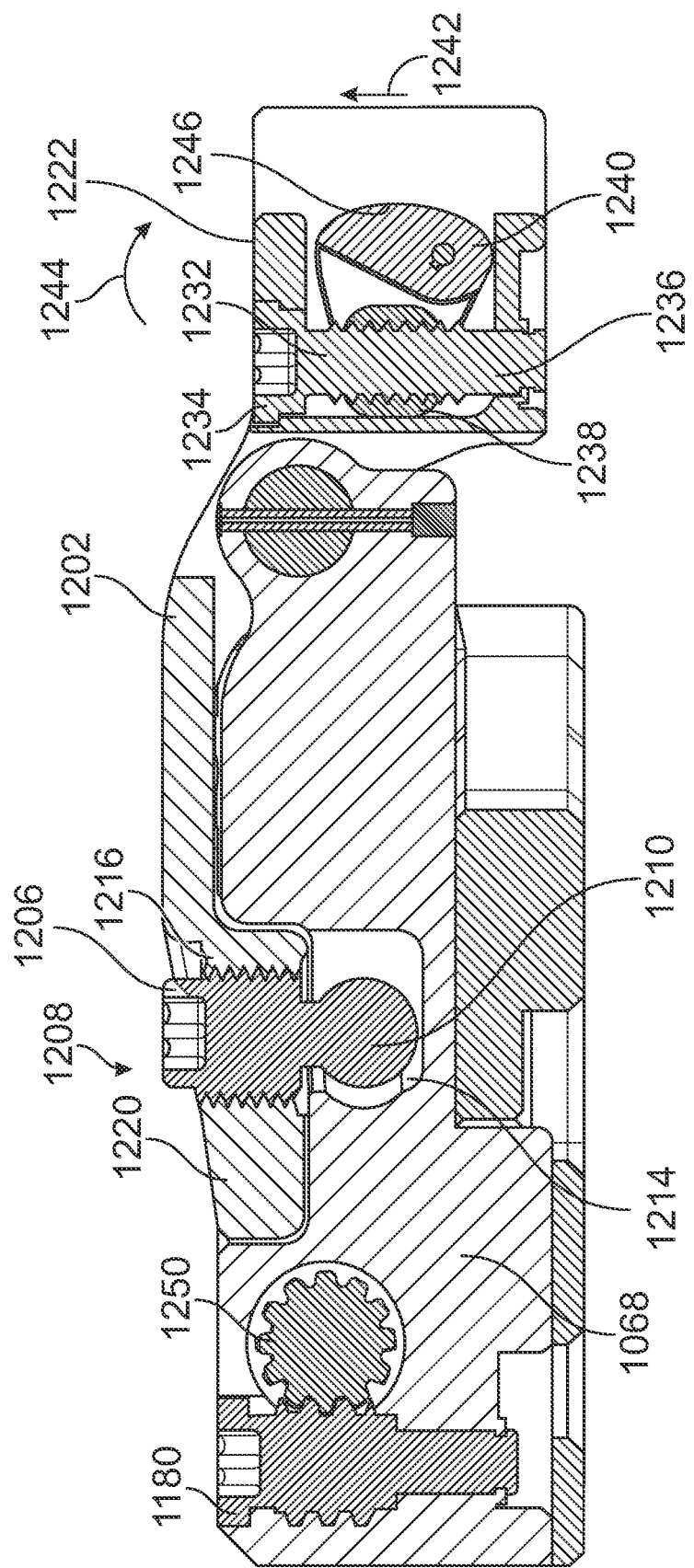
FIG. 43 is a cross-sectional view taken across line 43-43 in FIG. 37 showing a blade locking mechanism of the arm of the medial slider.

Regarding FIG. 42, the medial slider 1014 includes a blade pivot mechanism 1200 for pivoting an arm 1202 of the medial slider 1014 about a pivot axis 1204 relative to the body 1068. Regarding FIGS. 42 and 43, the blade pivot mechanism 1200 includes an actuator, such as a fastener 1206 having proximal head portion 1208 and a distal ball portion 1210 received in a pocket 1214 of the body 1068 of the medial slider 1014. The fastener 1206 also includes threads 1216 threadingly engaged with threads of the arm 1202. In this manner, turning of the fastener 1206 causes a lever portion 1220 of the arm 1202 to shift upward and pivot about the pivot connection 1206 which in turn causes a blade holder portion 1222 of the arm 1202 to pivot about the pivot connection 1204.

Regarding FIG. 42, the medial slider 1014 further includes a blade locking mechanism 1230 for releasably securing a blade to the blade holder portion 1222. In one embodiment, the blade locking mechanism 1230 includes a bolt 1232 having a head portion 1234 (see FIG. 43) with a rotary drive structure and a threaded shank portion 1236. The blade locking mechanism 1230 includes a nut 1238 threadingly engaged with the shank portion 1236 and connected to a pivotal locking member 1240. The turning of the bolt 1232 in a tightening direction shifts the nut 1238 upward in direction 1242 and pivots the locking member 1240 outward in direction 1244. The movement of a clamp surface 1246 of the locking member 1240 in direction 1244 into a recess 1248 (see FIG. 42) of the blade holder portion 1222 applies pressure against the blade 1006 received in the recess 1248. In this manner, the locking member 1240 tightly presses the blade mounting portion 1249 (see FIG. 51) against flange portions 1252 (see FIG. 42) of the blade holder portion 1222. In this manner, the blade 1006 is locked to the blade holder portion 1222 until the bolt 1232 is turned in a loosening direction.

Regarding FIG. 42, the pinion gear 1182 engages the teeth 1078 of the base frame 1016. In this manner, the pinion gear 1182 of the medial slider 1014 and the pinion gear 1154 of the intermediate frame 1018 both engage the teeth 1078 of the base frame 1016. Further, the pinion gears 1182, 1154 may move along the teeth 1078 independently of one another.

Figure 44:
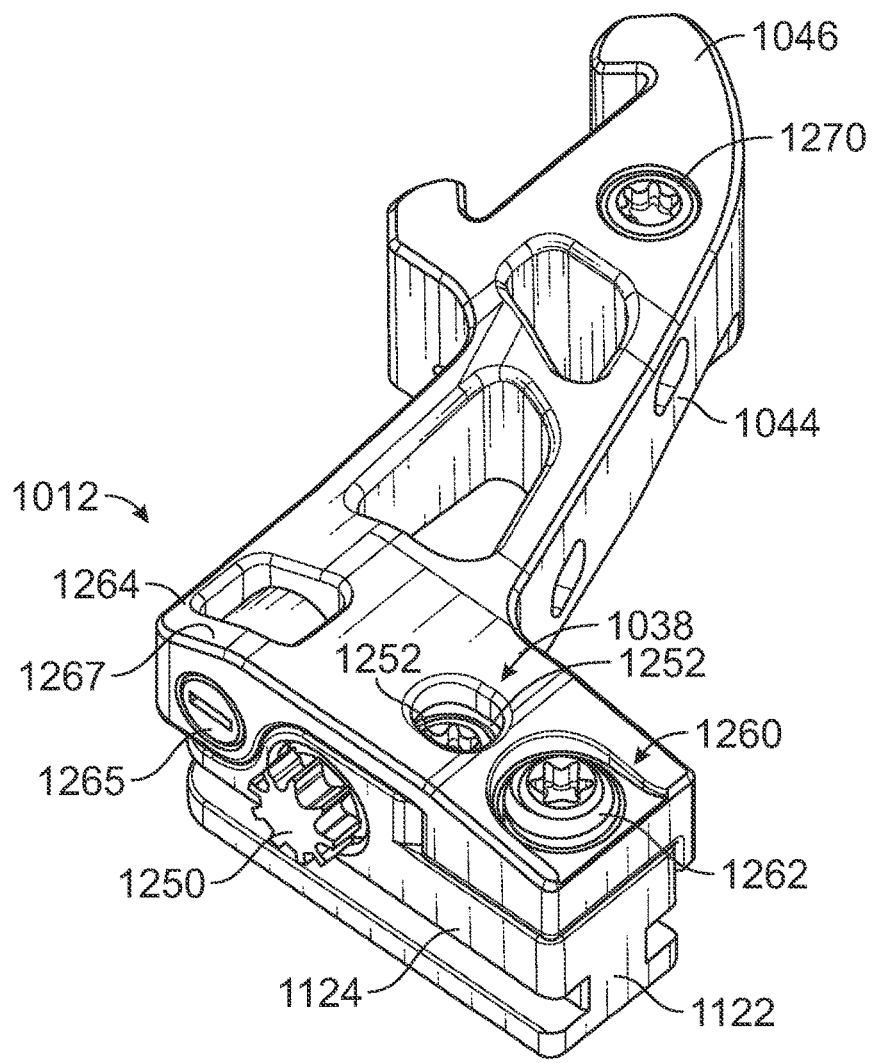
FIG. 44 is a perspective view of one of the lateral sliders of the retractor of FIG. 37 showing an arm of the slider pivotally connected to a body of the slider and including a lateral offset portion of the arm spaces a blade holder portion of the arm from the body of the slider.

Regarding FIG. 44, the lateral slider 1012 includes the lateral slider drive 1038 that is similar to the medial slider drive 1032 discussed above and includes a pinion gear 1250 that may be turned by a turning of a worm screw 1252 engaged with a worm gear 1253 coupled to the pinion gear 1250.

Figure 45:
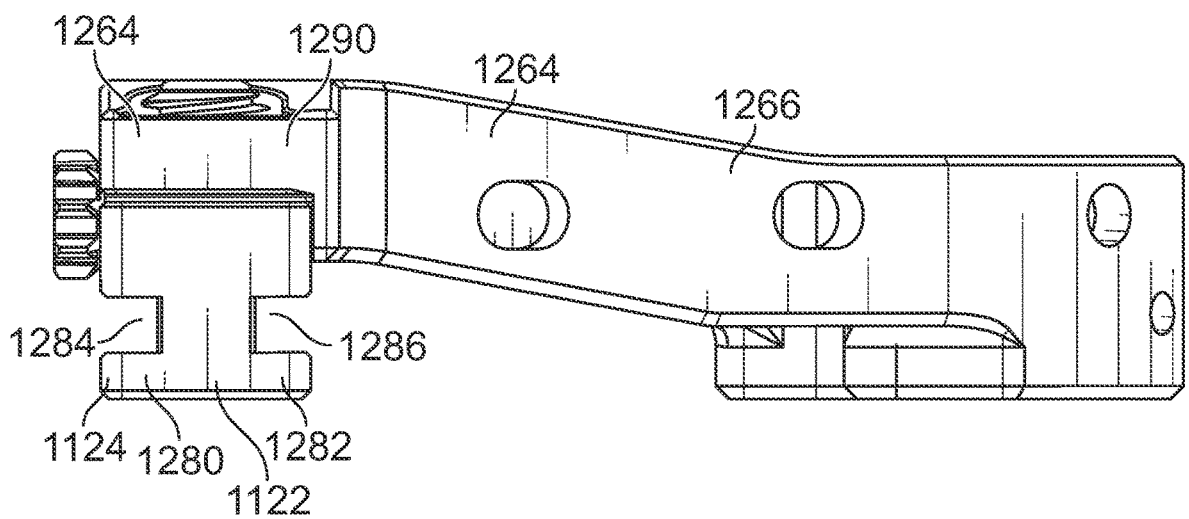
FIG. 45 is a side elevational view of the lateral slider of FIG. 44 showing the offset portion having a transverse extent.

Regarding FIGS. 44 and 45, the lateral slider 1012 further includes a blade pivot mechanism 1260 that is similar to the blade pivot mechanism 1200 discussed above and includes a fastener 1262 and may be rotated to pivot the arm 1044 of the lateral slider 1012 about a pivot connection 1265 relative to the body 1124. The arm 1264 further includes an offset portion 1266 and a blade holder portion 1046. The blade holder portion 1046 includes a blade locking mechanism 1270 that is similar to the blade locking mechanism 1230.

Regarding FIGS. 44 and 45, the projection 1122 includes flange portions 1280, 1282 extending in opposite directions. The body 1124 includes recesses 1284, 1286 that receive the flange portions 1130, 1132 of the intermediate frame 1118. Regarding FIG. 45, the offset portion 1266 includes an angled portion extending downward and away from a pivot portion 1290 of the arm 1264.

With reference to FIGS. 40 and 44, the lateral sliders 1010, 1012 have a compact configuration of the bodies 1124 and arms 1044 which positions the pivot connections 1265 onboard the intermediate frame 1118. The pivot connections 1265 and pivot portions 1267 of the arms 1044 are on and above the intermediate frame 1118. In other words, the pivot connections 1265 and pivot portions 1267 of the arms 1044 are within the footprint or periphery of the intermediate frame 1118. The arms 1044 are cantilevered from the intermediate frame 1118 and extend laterally from the intermediate frame 1118 such that the arms 1044 extend from the pivot connections 1265 above and away from a side 1269 of the intermediate frame 118 adjacent a surgical site. The compact configuration of the retractor 1000 in the direction of movement of the medial slider 1014 limits imaging obstruction by the retractor 100 during oblique lateral interbody fusion (OLIF) procedures.

Figure 46:
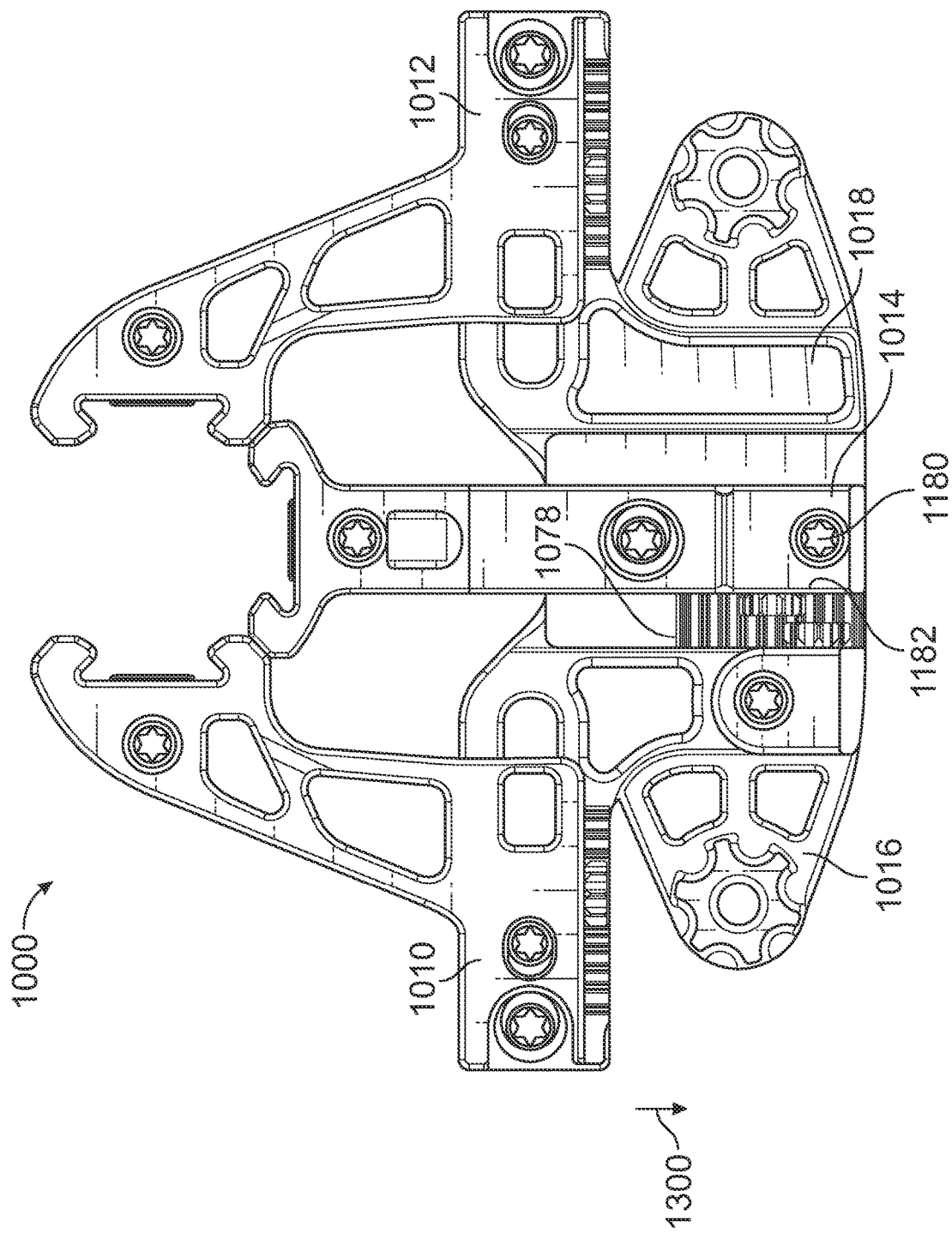
FIGS. 46-50 show the retractor of FIG. 37 in various operational configurations.
Figure 47:
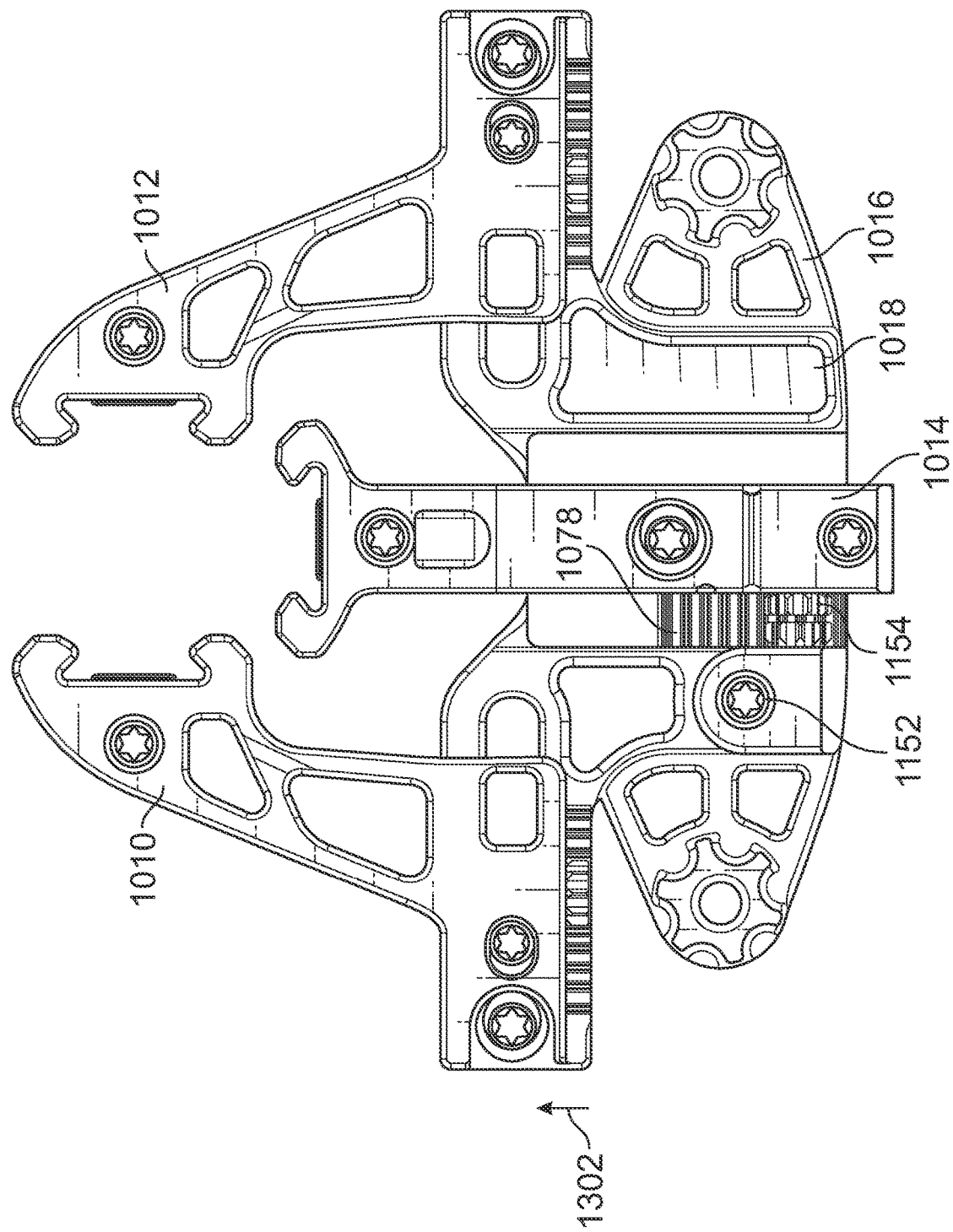

Regarding FIG. 46, the retractor 1000 is shown with the sliders 1010, 1012, 1014, the base frame 1016, and the intermediate frame 1018 in an initial configuration. Regarding FIGS. 46 and 47, the worm screw 1180 may be turned to retract the medial slider 1014 in direction 1300 to a retracted position as shown in FIG. 47. The turning of the worm screw 1180 causes the pinion gear 1182 to turn and drive the pinion gear 1182 along the teeth 1078 of the base frame 1016, which urges the medial slider 1014 in direction 1300.

Regarding FIG. 47, the worm screw 1152 of the intermediate frame 1018 may be turned to rotate the pinion gear 1154 and drive the pinion gear 1154 along the teeth 1078 of the base frame 1016. The driving of the pinion gear 1154 along the teeth 1078 drives the intermediate frame 1018, including the lateral sliders 1010, 1012 carried thereon, in direction 1302 relative to the base frame 1016.

Figure 48:
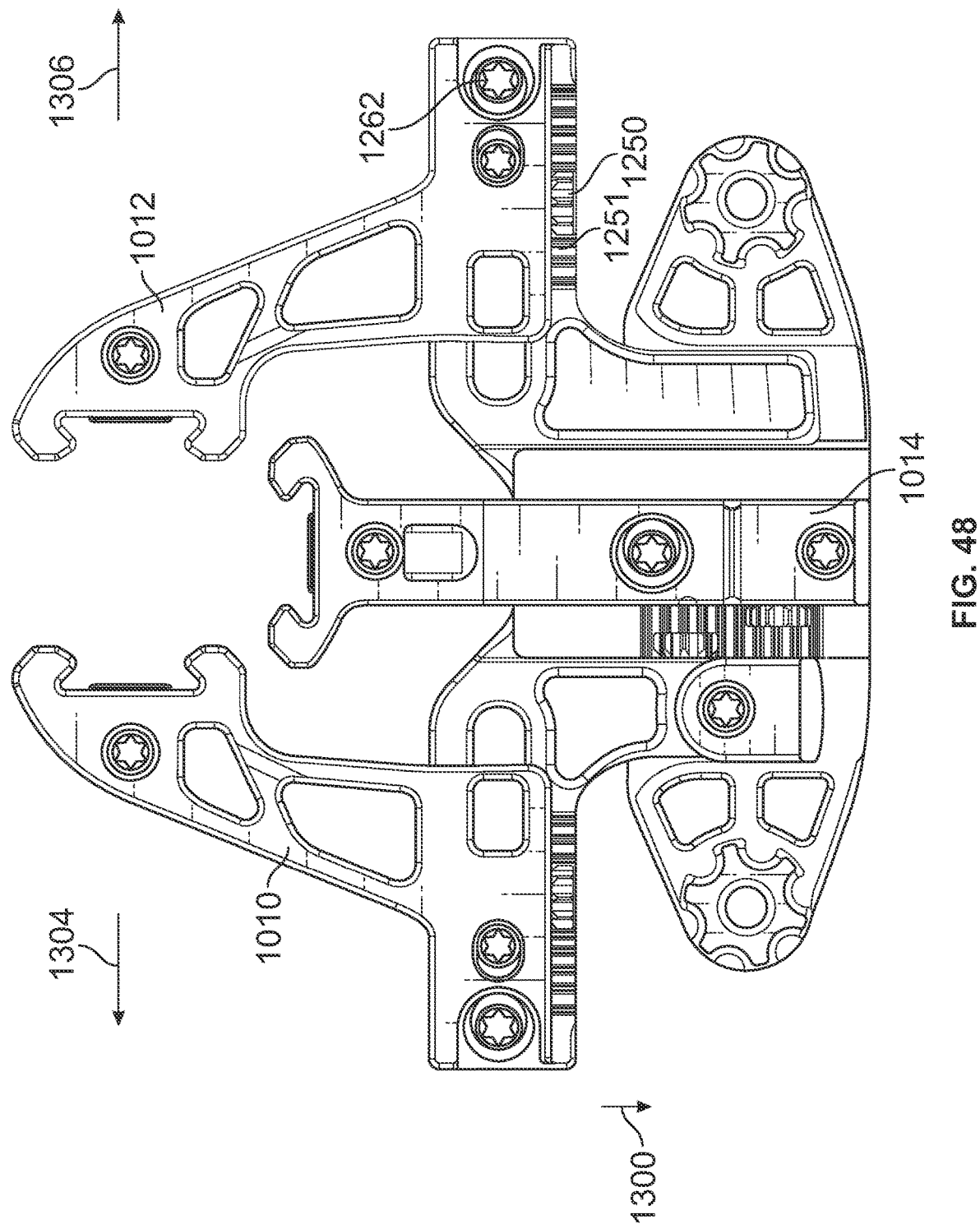

Regarding FIG. 48, the lateral sliders 1010, 1012 may be retracted in directions 1304, 1306 by turning the respective worm gear 1262 which causes the pinion gears 1250 to rotate and drive the pinion gear 1250 along the teeth 1251 of the intermediate frame 1018.

Figure 49:
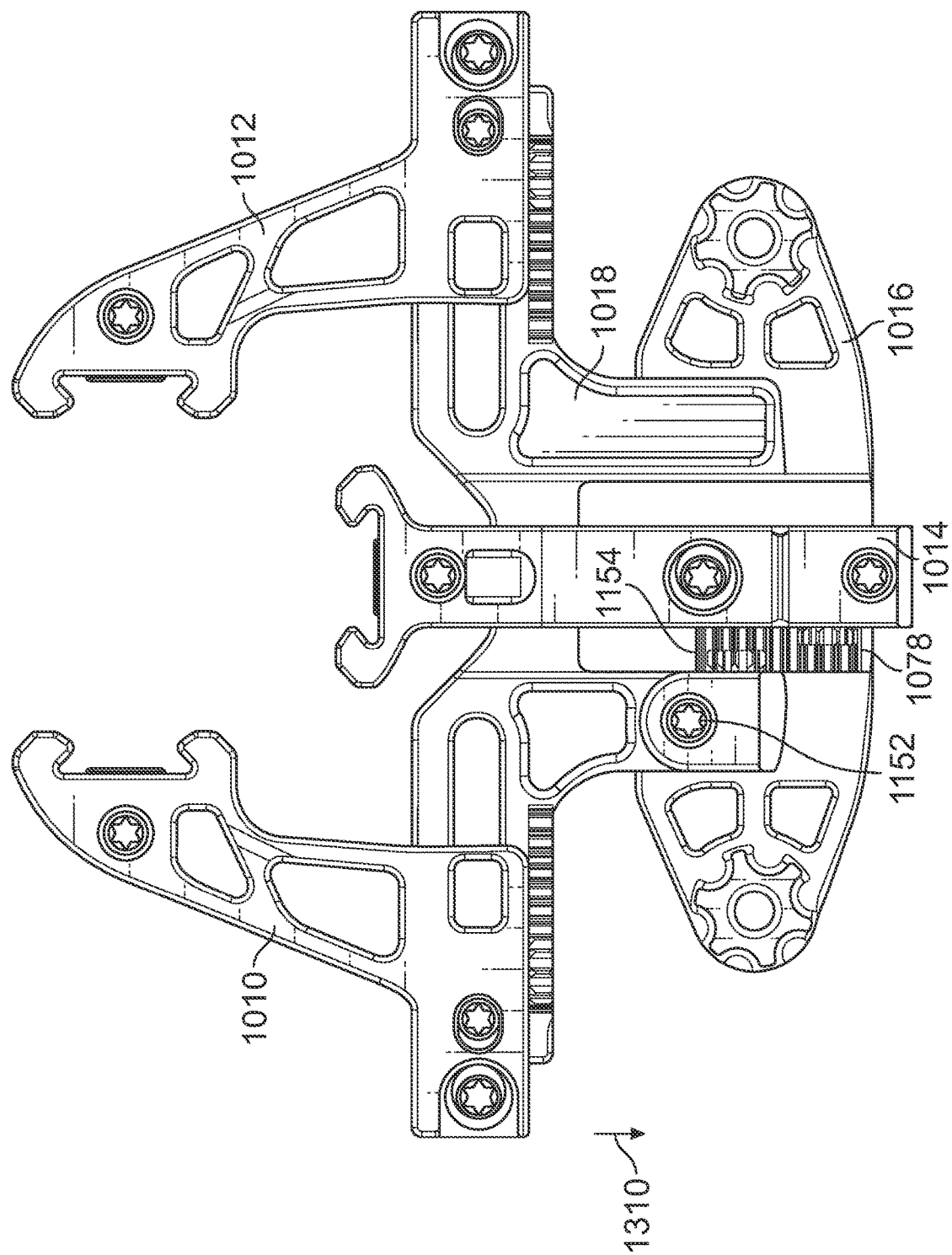
Figure 50:
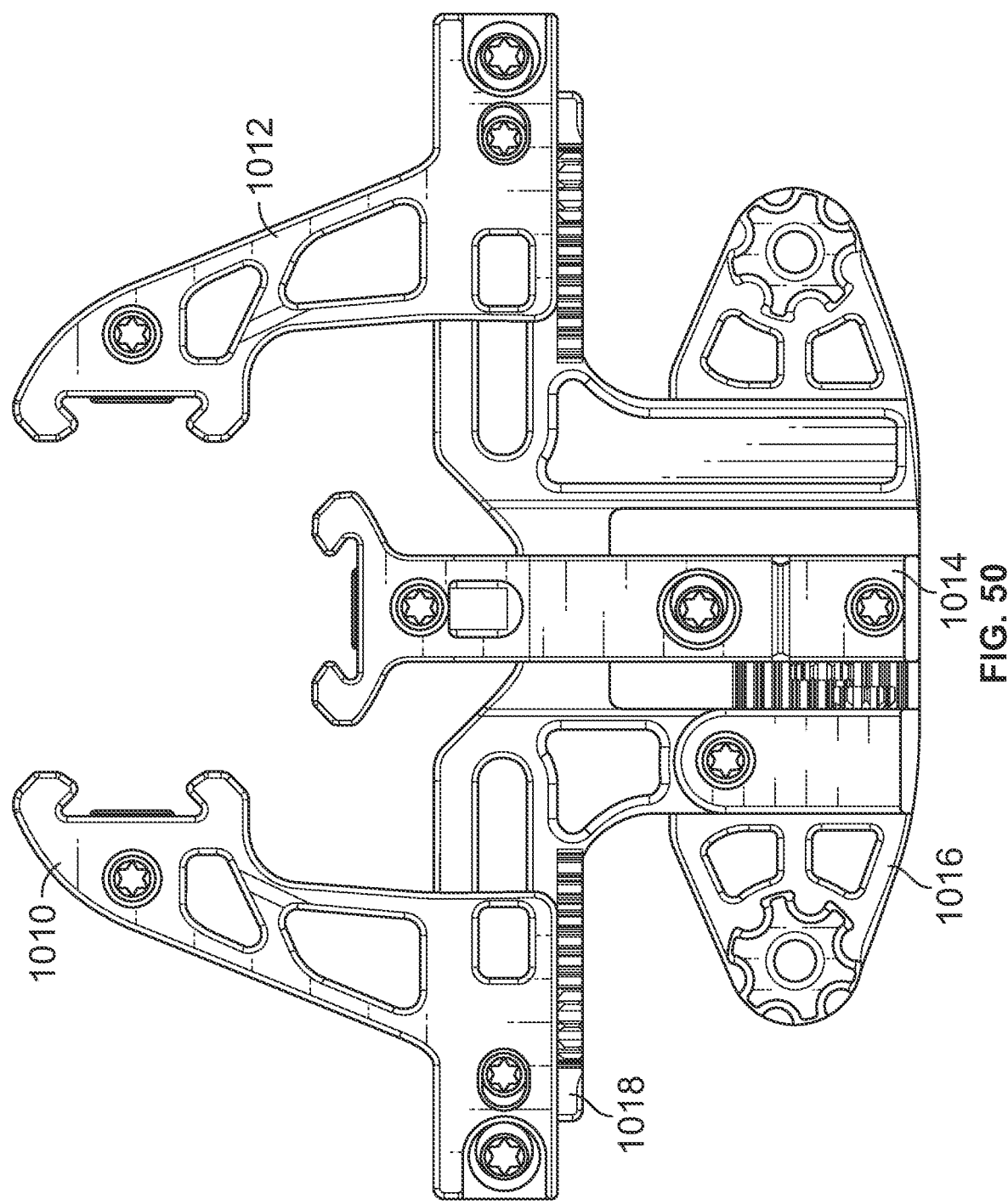

Regarding FIGS. 49 and 50, the intermediate frame 1018 may be shifted back in direction 1310 relative to the base frame 1016 by turning the worm screw 1152 in an opposite direction used to shift the intermediate frame 1018 in direction 1302. The turning of the worm screw 1112 causes rotation and driving of the pinion gear 1154 along the teeth 1078 of the base frame 1016.

Figure 51:
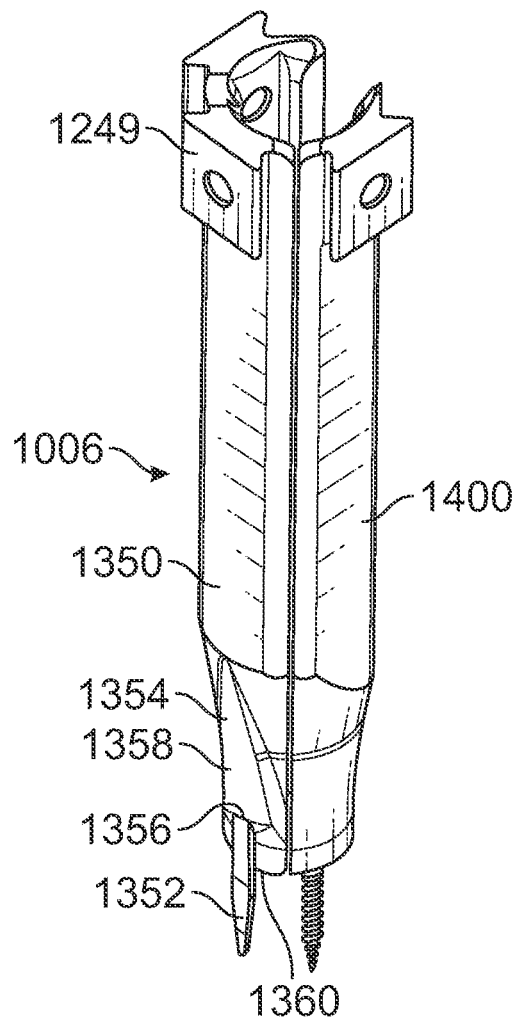
FIG. 51 is a perspective view of retractor blades that may be used with the retractor of FIG. 37.

Regarding FIG. 51, the blades 1006 include a blade 1350 having an anchor 1352 for engaging tissue of a patient such as an inter-vertebral disc. The blade 1350 has a body 1354 with a through opening 1356 in outer surface 1358 of the body 1354 that permits the anchor 1352 to extend outward from the opening 1356. In this manner, an anchor 1352 may extend distally beyond a distal end 1360 of the body 1354 without affecting an inner diameter of the blade 1350.

Figure 52:
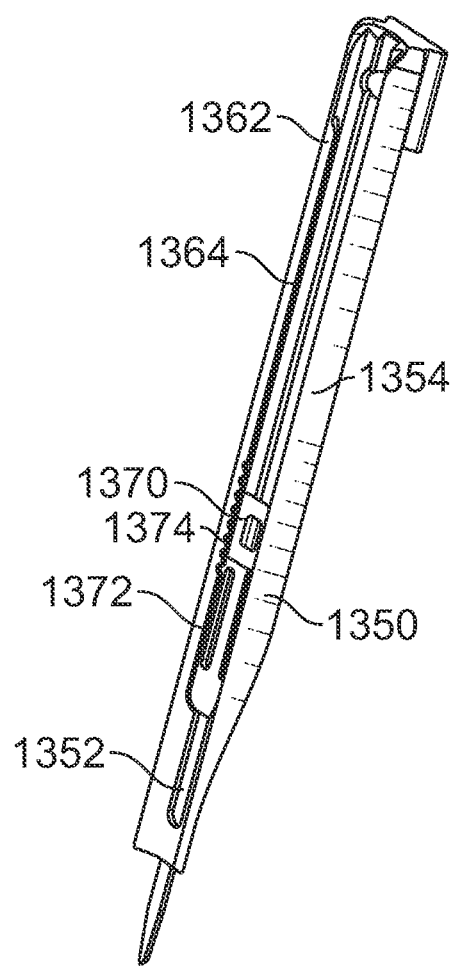
FIG. 52 is a perspective view of one of the blades of FIG. 51 showing an interior anchor that may be advanced outward from a distal end of the blade body.
Figure 53:
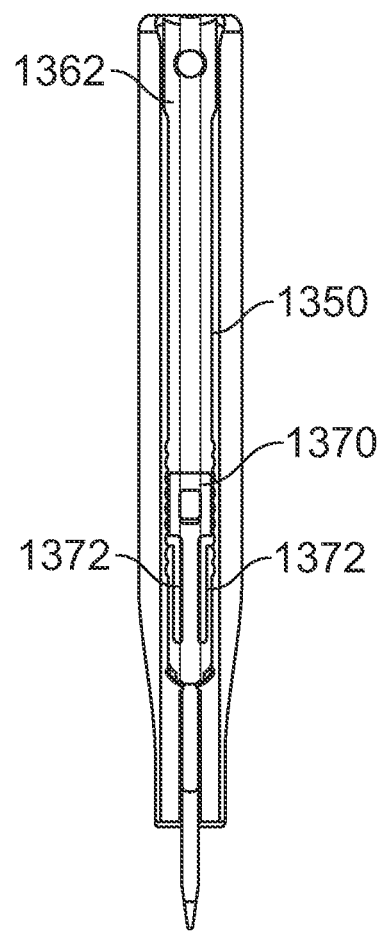
FIG. 53 is an elevational view of the blade of FIG. 52 showing the anchor received in an inner channel of the blade.
Figure 54:
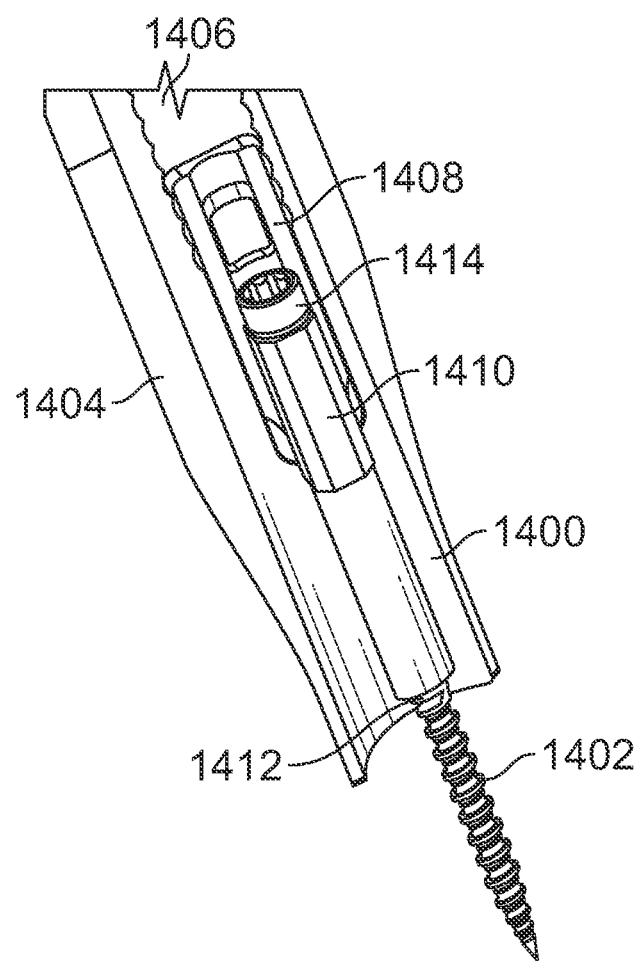
FIG. 54 is a perspective view of another one of the blades of FIG. 51 showing a threaded anchor extending from a distal end of a body of the blade.

Regarding FIG. 52, the blade body 1354 has a channel 1362 with opposing flange portions 1364 that permit the anchor 1352 to be slidably received in the channel 1362. Regarding FIGS. 52 and 53, the anchor 1352 includes a gripping portion, such as a loop 1370, that permits the anchor to be shifted along the channel 1362 as desired. The anchor 1352 further includes resilient arms 1372 that are resiliently biased apart and engage notches 1374 formed in the flange portions 1364 of the blade body 1354. The engagement between the arms 1372 and the notches 1374 operates as a detent that retains the anchor 1352 at a desired axial position along the blade 1350. Regarding FIGS. 51 and 54, the blades 1006 also include a blade 1400 having an anchor, such as a threaded anchor 1402, that may be driven into bone to secure the blade 1400 relative to the bone. The blade 1400 includes a body 1404 with a channel 1406 that slidably receives a mount 1408. The mount 1408 includes a collar portion 1410 that retains a shank 1412 of the threaded anchor 1402. The threaded anchor 1402 further includes a head 1414 that may have a rotary drive structure configured to be engaged with a driver to drive the threaded anchor 1402 into bone.

Figure 55:
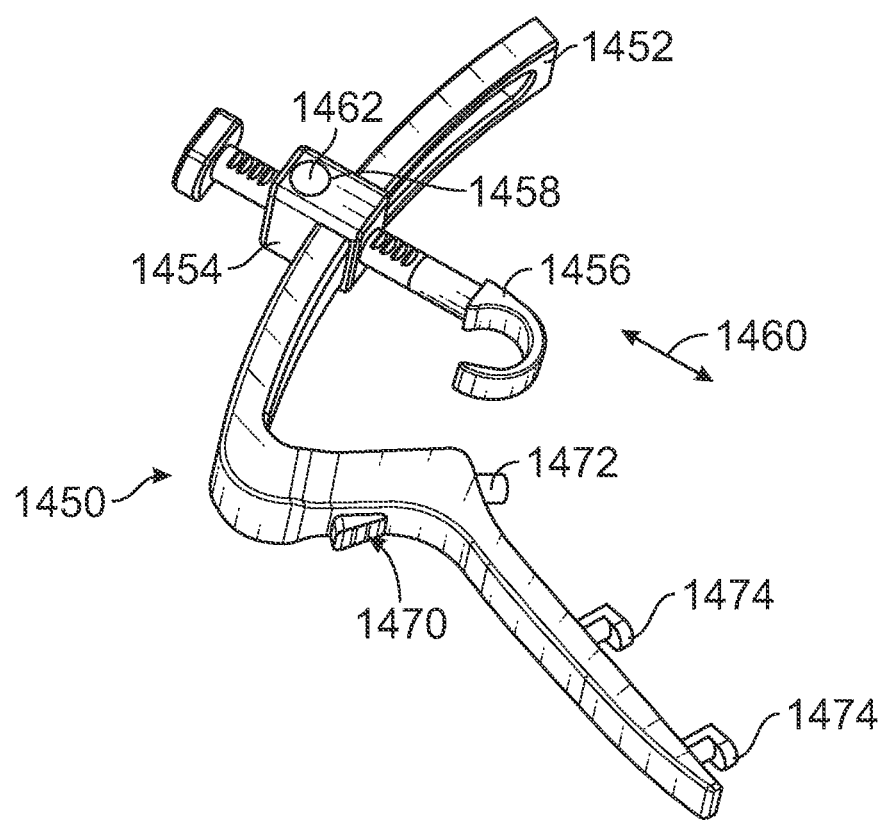
FIG. 55 is a perspective view of a supplementary blade arm.
Figure 56:
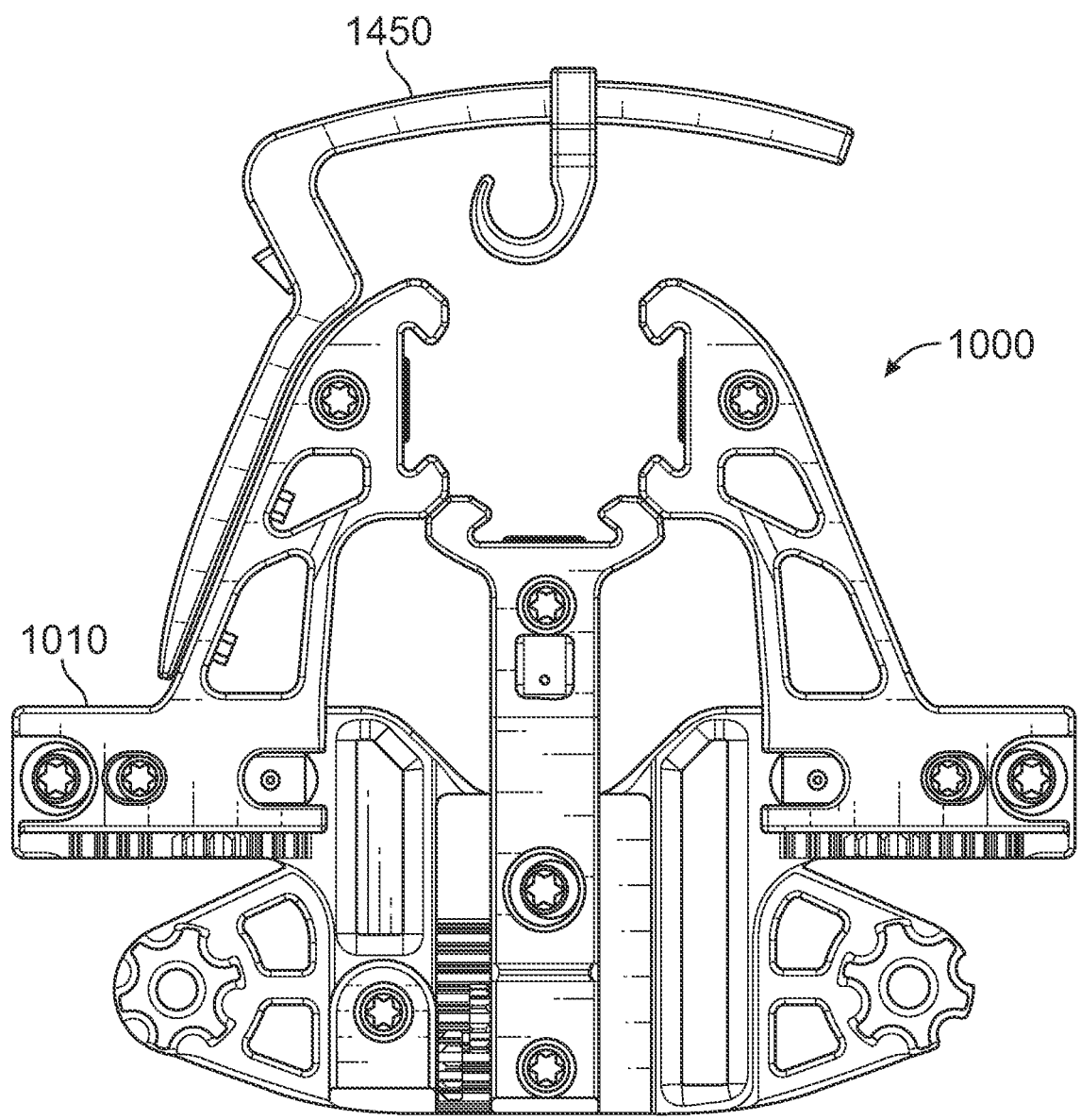
FIG. 56 is a plan view of the supplementary blade arm of FIG. 55 connected to the retractor of FIG. 37.

Regarding FIG. 55, in one embodiment, a supplementary blade arm 1450 may be provided that may include a body 1452 to which is slidably connected to a hook assembly 1454. The hook assembly 1454 may be shifted along the body 1452 includes a hook 1456 and a ratchet mechanism 1458 that permits the hook to be shifted in directions 1460 to the desired position and the release button 1462 for releasing the ratchet mechanism 1458 and permitting sliding of the hook 1456. The supplementary blade arm 1450 may also include a detent mechanism 1470 having a projection 1472 that engages a recess of the lateral slider 1010. The supplementary blade arm 1450 may also include one or more mating portions 1474, such as L-shaped members, that engage corresponding structures of the lateral slider 1010. Regarding FIG. 56, the supplementary blade arm 1450 may be connected to the lateral slider 1010 and may provide another attachment point for hooks, blades, or other surgical tools.

Uses of singular terms such as "a," "an," are intended to cover both the singular and the plural, unless otherwise indicated herein or clearly contradicted by context. The terms "comprising," "having," "including," and "containing" are to be construed as open-ended terms. It is intended that the phrase "at least one of" as used herein be interpreted in the disjunctive sense. For example, the phrase "at least one of A and B" is intended to encompass A, B, or both A and B.

While there have been illustrated and described particular embodiments of the present invention, it will be appreciated that numerous changes and modifications will occur to those skilled in the art, and it is intended for the present invention to cover all those changes and modifications which fall within the scope of the appended claims.

What is claimed is:

1. A surgical retractor comprising:
    sliders configured to have tissue engaging members connected thereto;
    slider drives including operating members, the operating members rotatable to cause the slider drives to shift the sliders relative to one another;
    a coupler having a coupling configuration wherein the coupler connects the slider drives and rotation of one of the operating members causes movement of the sliders, the coupler having a decoupling configuration wherein the coupler disconnects the slider drives and rotation of the one operating member causes movement of fewer sliders than the sliders that are moved with the coupler in the coupling configuration; and
    an actuator connected to the coupler and movable between a dependent slider movement position and an independent slider movement position to shift the coupler between the coupling configuration and the decoupling configuration.

2. The surgical retractor of claim 1 wherein rotation of any of the operating members causes movement of the sliders with the actuator in the dependent slider movement position and the coupler in the coupling configuration.

3. The surgical retractor of claim 1 wherein the slider drives include shafts;
    wherein the operating members are coupled to the shafts so that turning of the operating members causes turning of the shafts; and
    wherein the coupler connects the shafts with the coupler in the coupling configuration and the coupler disconnects the shafts with the coupler in the decoupling configuration.

4. The surgical retractor of claim 3 wherein the coupler and one of the shafts include members that are engaged with the coupler in the coupling configuration and are disengaged with the coupler in the decoupling configuration.

5. The surgical retractor of claim 3 wherein the coupler includes a sleeve member having an opening to receive the shafts; and
    wherein moving the actuator between the dependent slider movement position and the independent slider movement position shifts the sleeve member along the shafts.

6. The surgical retractor of claim 1 further comprising a frame and slide connections between the sliders and the frame; and
    wherein the slider drives include threaded shafts and threaded nuts engaged with the threaded shafts, the operating members and sliders operably coupled to the threaded shafts and threaded nuts so that rotation of the operating members causes relative movement of the threaded shafts and threaded nuts and shifting of the sliders relative to the frame.

7. The surgical retractor of claim 6 wherein the sliders support the threaded nuts, the threaded nuts being shiftable between engaged and disengaged positions to disengage the threaded nuts from the threaded shafts and permit the sliders to be shifted relative to the frame without turning of the operating members.

8. The surgical retractor of claim 1 in combination with the tissue engaging members, the tissue engaging members each having a distal end, a proximal end, and a longitudinal length extending therebetween;
    wherein the tissue engaging members and the sliders include lateral openings and lateral bosses configured to permit the sliders to be shifted laterally relative to the tissue engaging members to advance the lateral bosses into the lateral openings and connect the sliders to the tissue engaging members; and
    locks of the sliders configured to releasably secure the sliders and the tissue engaging members.

9. The surgical retractor of claim 1 wherein the sliders each comprise:
    a body;
    an arm having an interface to receive one of the tissue engaging members;
    a pivot connection connecting the body and the arm; and
    a rotatable pivot member operable to pivot arm relative to the body and angle the one tissue engaging member connected to the arm.

10. The surgical retractor of claim 1 further comprising:
    a frame;
    slide connections between the sliders and the frame;
    a medial slider intermediate the sliders along the frame and configured to have a medial tissue-engaging member connected thereto; and
    a medial slider drive operable to shift the medial slider between extended and retracted positions.

11. The surgical retractor of claim 1 wherein, with the actuator in the dependent configuration and the coupler in the coupling configuration, rotating the operating member causes the sliders to move simultaneously.

12. A retractor system comprising:
    a retractor;
    a tissue engaging member assembly having a proximal end portion to connect to the retractor and a distal end portion;
    a bone screw having a head portion and a threaded shank portion for engaging a bone, the head portion having a rotary drive structure;
    an adapter of the tissue engaging member assembly configured for being secured to the bone screw, the adapter comprising:
        a body having an interior to receive the head portion of the bone screw, the body having a body thread and a central longitudinal axis;
        an opening of the body sized to permit the body and the bone screw head to be shifted laterally relative to one another to advance the bone screw head portion through the opening of the body and into the interior of the body; and
        a locking member having a locking member thread configured to engage the body thread and a locking member rotary drive structure to receive a driver for turning the locking member, the locking member rotatable by the driver in a first direction to shift the locking member along the central longitudinal axis of the body via engagement of the body thread and the locking member thread from an unlocked position wherein the locking member permits the locking member and body to pivot relative to the bone screw to a locked position wherein the locking member clamps the bone screw head between the locking member and the body to fix the locking member and body against pivoting relative to the bone screw.

13. The retractor system of claim 12 wherein the locking member has a lower portion positioned to permit the bone screw head portion to be advanced through the opening of the body with the locking member in the unlocked position, the lower portion obstructing the opening of the body with the locking member in the locked position to inhibit removal of the bone screw head portion from the interior of the body.

14. The retractor system of claim 12 wherein the locking member rotary drive structure includes an upper rotary drive structure and the locking member includes a lower clamping portion to engage the bone screw head portion;
wherein the clamping portion of the body extends intermediate the bone screw head portion and the opening of the body with the locking member in the locked position to inhibit removal of the bone screw head portion from the interior of the body.

15. The retractor system of claim 12 wherein the locking member includes a through opening to permit a tool to extend therein and engage the rotary drive structure of the bone screw.

16. The retractor system of claim 12
wherein the body includes a collar portion that extends about a lower portion of the bone screw head portion with the head portion received in the body opening;
wherein the locking member includes a clamping portion configured to engage an upper portion of the head portion; and
wherein the head portion of the bone anchor is clamped between the collar portion of the body and the clamping portion of the locking member with the locking member in the locked position.

17. The retractor system of claim 12 wherein the tissue engaging member assembly includes a tissue engaging member and a releasable connection between the body of the adapter and the tissue engaging member.

18. The retractor system of claim 12 wherein the tissue engaging member assembly includes a tissue engaging member having a channel; and
the body of the adapter includes a blade connector portion configured to form a slide connection with the channel of the tissue engaging member.

19. The surgical retractor of claim 12 wherein the locking member is rotatable by the driver in a second direction opposite the first direction to shift the locking member along the central longitudinal axis of the body from the locked position to the unlocked position.

20. A surgical retractor comprising:
a base frame having a portion to be secured to a support structure;
a first slider to receive a first tissue engaging member;
a first slider drive operable to shift the first slider between extended and retracted positions relative to the base frame;
an intermediate frame;
a frame slide connection between the base frame and intermediate frame;
second and third sliders on opposite sides of the first slider to receive second and third tissue engaging members, the second and third sliders including bodies, arms, and pivot connections between the bodies and the arms;
wherein the pivot connections between the bodies and the arms are onboard the intermediate frame;
slide connections between the bodies of the second and third slider and the intermediate frame;
second and third slider drives operable to shift the second and third sliders longitudinally between extended and retracted positions relative to the intermediate frame;
the arms of the second and third sliders extending laterally outward from the intermediate frame to position the second and third tissue engaging members laterally offset and spaced from the intermediate frame; and
an intermediate frame drive operable to shift the intermediate frame and the second and third sliders connected thereto relative to the base frame to facilitate positioning of the second and third sliders independent of the first slider.

21. The surgical retractor of claim 20 wherein the arms include pivot portions pivotally connected to the bodies, the bodies being intermediate the pivot portions of the arms and the intermediate frame; and
wherein the arms include tissue engaging member-receiving portions and offset portions extending laterally from the pivot portions to the tissue engaging member-receiving portions.

22. The surgical retractor of claim 20 wherein the second and third sliders include rotatable pivot members operably coupled to the arms and the bodies, the rotatable pivot members being rotatable to cause pivoting of the arms relative to the bodies; and
wherein the rotatable pivot members are onboard the intermediate frame.

23. The surgical retractor of claim 20 wherein the base frame includes a rack;
wherein the first slider drive includes a first pinion gear engaged with the rack and rotatable to shift the first slider relative to the base frame; and
wherein the frame drive includes a second pinion gear engaged with the rack and rotatable to shift the intermediate frame and second and third sliders connected thereto relative to the base frame.

24. The surgical retractor of claim 20 wherein the intermediate frame includes racks; and
wherein the second and third sliders include rotatable drive members engaged with the racks and rotatable to shift the second and third sliders longitudinally between the retracted and extended positions.

25. The surgical retractor of claim 20 wherein the base frame includes a pair of walls and a recess therebetween that receives the first slider; and
wherein the frame slide connection includes engaged projections and recesses of the intermediate frame and the base frame on opposite sides of the walls from the first slider.

26. The surgical retractor of claim 20 wherein the intermediate frame drive comprises:
a worm screw;
a worm gear engaged with the worm screw, the worm gear associated with a rotatable drive member; and
wherein the worm screw is rotatable to rotate the worm gear and the rotatable drive member and cause shifting of the intermediate frame relative to the base frame.

27. The surgical retractor of claim 20 wherein the intermediate frame drive includes a rack of one of the base frame and the intermediate frame and a pinion gear rotatably supported on the other the base frame and the intermediate frame.

28. The surgical retractor of claim 27 wherein the intermediate frame drive includes a worm gear connected to the pinion gear and a worm screw having a rotary drive structure to receive a tool to turn the worm screw and cause turning of the worm gear and pinion gear.

29. The surgical retractor of claim 20 wherein the base frame has a unitary, one-piece construction; and
   wherein the intermediate frame has a unitary, one-piece construction.

30. The surgical retractor of claim 20 in combination with a supplementary blade arm, the supplementary blade arm and one of the second and third sliders having a mating projection and recess to connect the supplementary blade arm and the one of the second and third sliders; and
   wherein the supplementary blade arm includes a detent mechanism to releasably secure the supplementary blade arm and the one of the second and third sliders.

* * * * *